US009925184B2

(12) United States Patent
Zisman

(10) Patent No.: US 9,925,184 B2
(45) Date of Patent: Mar. 27, 2018

(54) SPRAY-DRY FORMULATIONS

(71) Applicants: Pulmokine, Inc., Rensselaer, NY (US); GILEAD SCIENCES, INC., Foster City, CA (US)

(72) Inventor: Lawrence S Zisman, Rensselaer, NY (US)

(73) Assignees: Pulmokine, Inc., Rensselaer, NY (US); Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/028,347

(22) PCT Filed: Oct. 10, 2014

(86) PCT No.: PCT/US2014/060039
§ 371 (c)(1),
(2) Date: Apr. 8, 2016

(87) PCT Pub. No.: WO2015/054574
PCT Pub. Date: Apr. 16, 2015

(65) Prior Publication Data
US 2016/0235742 A1    Aug. 18, 2016

Related U.S. Application Data

(60) Provisional application No. 61/889,887, filed on Oct. 11, 2013.

(51) Int. Cl.
A61K 31/497    (2006.01)
A61K 31/4965   (2006.01)
A61K 31/506    (2006.01)
A61K 9/00      (2006.01)
A61K 9/16      (2006.01)

(52) U.S. Cl.
CPC ......... *A61K 31/497* (2013.01); *A61K 9/0075* (2013.01); *A61K 9/1617* (2013.01); *A61K 31/4965* (2013.01); *A61K 31/506* (2013.01)

(58) Field of Classification Search
CPC ... A61K 31/497; A61K 9/0075; A61K 9/1617
USPC .............................................. 1/1
See application file for complete search history.

(56) References Cited

U.S. PATENT DOCUMENTS

| | | | |
|---|---|---|---|
| 4,570,630 A | 2/1986 | Elliott et al. | |
| 5,093,340 A | 3/1992 | Mohrs et al. | |
| 5,648,369 A | 7/1997 | Kadaba | |
| 6,329,386 B1 | 12/2001 | Mollison | |
| 6,635,641 B2 | 10/2003 | Bender et al. | |
| 7,122,550 B2 | 10/2006 | Burns et al. | |
| 7,259,179 B2 | 8/2007 | Burns et al. | |
| 7,511,047 B2 | 3/2009 | Burns et al. | |
| 7,598,272 B2 | 10/2009 | Burns et al. | |
| 8,084,456 B2 | 12/2011 | Burns et al. | |
| 8,257,741 B2 | 9/2012 | Curatolo et al. | |
| 8,263,128 B2 | 9/2012 | Curatolo et al. | |
| 8,268,850 B2 | 9/2012 | Li et al. | |
| 8,288,540 B2 | 10/2012 | Chianelli et al. | |
| 8,293,757 B2 | 10/2012 | Molteni et al. | |
| 8,338,417 B2 | 12/2012 | Li et al. | |
| 8,378,108 B2 | 2/2013 | Corkey et al. | |
| 8,410,173 B2 | 4/2013 | Zisman | |
| 8,461,161 B2 | 6/2013 | Burns et al. | |
| 8,569,283 B2 | 10/2013 | Molteni et al. | |
| 8,889,700 B2 | 11/2014 | Von Nussbaum et al. | |
| 9,029,386 B2 | 5/2015 | Burns et al. | |
| 9,199,981 B2 | 12/2015 | Yeh et al. | |
| 2002/0120011 A1 | 8/2002 | Sikorski et al. | |
| 2004/0018243 A1 | 1/2004 | Basu et al. | |
| 2006/0154936 A1 | 7/2006 | Lasky | |
| 2007/0099935 A1 | 5/2007 | Burns et al. | |
| 2007/0161635 A1 | 7/2007 | Burns et al. | |
| 2008/0268460 A1 | 10/2008 | Loganzo et al. | |
| 2009/0197922 A1 | 8/2009 | Maitland et al. | |
| 2010/0130447 A1 | 5/2010 | Burns et al. | |
| 2011/0117159 A1 | 5/2011 | Zisman | |
| 2011/0190313 A1 | 8/2011 | Pascoe et al. | |
| 2013/0137660 A1 | 5/2013 | Burns et al. | |
| 2014/0038988 A1 | 2/2014 | Von et al. | |
| 2015/0044288 A1 | 2/2015 | Surber | |
| 2015/0352111 A1 | 12/2015 | Zisman | |
| 2015/0353527 A1 | 12/2015 | Zisman | |

FOREIGN PATENT DOCUMENTS

| | | | |
|---|---|---|---|
| EP | 1522314 A1 | 4/2005 | |
| EP | 1948176 B1 | 1/2011 | |
| GB | 2011892 A | 7/1979 | |
| JP | S5461189 A | 5/1979 | |

(Continued)

OTHER PUBLICATIONS

Burns, et al., Discovery of 2-(α-methylbenzylamino) pyrazines as potent Type II inhibitors of FMS. Bioorganic & Medicinal Chemistry letters. 19(2009):1206-1209.
European search report and opinion dated Jun. 15, 2016 for EP Application No. 14737648.
Office action dated Aug. 24, 2016 for U.S. Appl. No. 14/760,139.
European Search Report and Written Opinion dated Oct. 12, 2016 for EP Application No. 14737772.5.
International search report dated Jan. 9, 2008 for PCT/AU2007/001761.
Purandare, et al. Identification of chemokine receptor CCR4 antagonist. Bioorg Med Chem Lett. May 16, 2005;15(10):2669-72. DOI:10.1016/j.bmcl.2005.02.084.

(Continued)

*Primary Examiner* — Yanzhi Zhang
(74) *Attorney, Agent, or Firm* — Wilson Sonsini Goodrich & Rosati

(57) ABSTRACT

Disclosed herein are compounds, compositions, and methods for preventing and treating proliferative diseases associated with aberrant receptor tyrosine kinase (RTK) activity. The therapeutic indications described herein more specifically relate to the non-selective inhibition of RTKs associated with vascular and pulmonary disorders.

21 Claims, 29 Drawing Sheets

(56) References Cited

FOREIGN PATENT DOCUMENTS

| | | |
|---|---|---|
| JP | H09268169 A | 10/1997 |
| JP | 2005538975 A | 12/2005 |
| JP | 2006111553 A | 4/2006 |
| WO | WO-9708135 A1 | 3/1997 |
| WO | WO-0128993 A2 | 4/2001 |
| WO | WO-0129025 A2 | 4/2001 |
| WO | WO-0153274 A1 | 7/2001 |
| WO | WO-0162251 A1 | 8/2001 |
| WO | WO-0162252 A1 | 8/2001 |
| WO | WO-02060492 A1 | 8/2002 |
| WO | WO-03000666 A1 | 1/2003 |
| WO | WO-03099706 A1 | 12/2003 |
| WO | WO-03099796 A1 | 12/2003 |
| WO | WO-03099811 A1 | 12/2003 |
| WO | WO-2004004720 A1 | 1/2004 |
| WO | WO-2004006858 A2 | 1/2004 |
| WO | WO-2004052868 A1 | 6/2004 |
| WO | WO-2005002673 A1 | 1/2005 |
| WO | WO-2005011594 A2 | 2/2005 |
| WO | WO-2005013982 A1 | 2/2005 |
| WO | WO-2005047244 A2 | 5/2005 |
| WO | WO-2005054199 A1 | 6/2005 |
| WO | WO-2005066156 A1 | 7/2005 |
| WO | WO-2007124382 A2 | 11/2007 |
| WO | WO-2008058341 A1 | 5/2008 |
| WO | WO-2010102065 A1 | 9/2010 |
| WO | WO-2010102066 A1 | 9/2010 |
| WO | WO-2010132827 A1 | 11/2010 |
| WO | WO-2012031129 A2 | 3/2012 |
| WO | WO-2012040502 A1 | 3/2012 |
| WO | WO-2012106575 A1 | 8/2012 |
| WO | WO-2012159103 A1 | 11/2012 |
| WO | WO-2014110198 A2 | 7/2014 |
| WO | WO-2014110200 A1 | 7/2014 |
| WO | WO-2015179369 A1 | 11/2015 |

OTHER PUBLICATIONS

Remington: The Science and Practice of Pharmacy, 21st Ed. Lippincott Williams & Wilkins (2005).

Abe, et al. Formation of plexiform lesions in experimental severe pulmonary arterial hypertension. Circulation. Jun. 29, 2010;121(25):2747-54. doi: 10.1161/CIRCULATIONAHA.109.927681. Epub Jun. 14, 2010.

Barf, et al. Irreversible protein kinase inhibitors: balancing the benefits and risks. J Med Chem. Jul. 26, 2012;55(14):6243-62. doi: 10.1021/jm3003203. Epub Jun. 8, 2012.

Chen, et al. A cell-based immunocytochemical assay for monitoring kinase signaling pathways and drug efficacy. Anal Biochem. Mar. 1, 2005;338(1):136-42.

Ciuclan, et al. Imatinib attenuates hypoxia-induced pulmonary arterial hypertension pathology via reduction in 5-hydroxytryptamine through inhibition of tryptophan hydroxylase 1 expression. Am J Respir Crit Care Med. Jan. 1, 2013;187(1):78-89. doi: 10.1164/rccm.201206-1028OC. Epub Oct. 18, 2012.

Claesson-Welsh, et al. cDNA cloning and expression of a human platelet-derived growth factor (PDGF) receptor specific for B-chain-containing PDGF molecules. Mol Cell Biol. Aug. 1988;8(8):3476-86.

Cool, et al. Pathogenesis and evolution of plexiform lesions in pulmonary hypertension associated with scleroderma and human immunodeficiency virus infection. Hum Pathol. Apr. 1997;28(4):434-42.

Dahal, et al. Hypoxic pulmonary hypertension in mice with constitutively active platelet-derived growth factor receptor-β Pulm Circ. Apr.-Jun. 2011;1(2):259-68. doi: 10.4103/2045-8932.83448.

Deininger, et al. The development of imatinib as a therapeutic agent for chronic myeloid leukemia. Blood. Apr. 1, 2005;105(7):2640-53. Epub Dec. 23, 2004.

Diller, et al. Kinases, homology models, and high throughput docking. J Med Chem. Oct. 23, 2003;46(22):4638-47.

Discafani, et al. Irreversible inhibition of epidermal growth factor receptor tyrosine kinase with in vivo activity by N-[4-[(3-bromophenyl)amino]-6-quinazolinyl]-2-butynamide (CL-387,785). Biochem Pharmacol. Apr. 15, 1999;57(8):917-25.

Fan, et al. Nanofluidic proteomic assay for serial analysis of oncoprotein activation in clinical specimens. Nat Med. May 2009;15(5):566-71. doi: 10.1038/nm.1903. Epub Apr. 12, 2009.

Fisher, et al. Clinical differences between idiopathic and scleroderma-related pulmonary hypertension. Arthritis Rheum. Sep. 2006;54(9):3043-50.

Fry, et al. Specific, irreversible inactivation of the epidermal growth factor receptor and erbB2, by a new class of tyrosine kinase inhibitor. Proc Natl Acad Sci U S A. Sep. 29, 1998;95(20):12022-7.

Ghofrani, et al. Imatinib for the treatment of pulmonary arterial hypertension. N Engl J Med. Sep. 29, 2005;353(13):1412-3.

Ghofrani, et al. Imatinib in pulmonary arterial hypertension patients with inadequate response to established therapy. Am J Respir Crit Care Med. Nov. 1, 2010;182(9):1171-7. doi: 10.1164/rccm.201001-01230C. Epub Jun. 25, 2010.

Ghofrani, et al. Riociguat for pulmonary hypertension. N Engl J Med. Dec. 5, 2013;369(23):2268. doi: 10.1056/NEJMc1312903.

Greene, et al. Protective Groups in Organic Synthesis. John Wiley & Sons, New York, NY, (3rd Edition, 1999).

Grimminger, et al. PDGF receptor and its antagonists: role in treatment of PAH. Adv Exp Med Biol. 2010;661:435-46. doi: 10.1007/978-1-60761-500-2_28.

Gronwald, et al. Cloning and expression of a cDNA coding for the human platelet-derived growth factor receptor: evidence for more than one receptor class. Proc Natl Acad Sci U S A. May 1988;85(10):3435-9.

Hartwig. Transition metal catalyzed synthesis of arylamines and aryl ethers from aryl halides and triflates: Scope and mechanism. Angew. Chem. Int. Ed. Aug. 17, 1998; 37(15):2046-2067.

Hoeper, et al. Imatinib mesylate as add-on therapy for pulmonary arterial hypertension: results of the randomized IMPRES study. Circulation. Mar. 12, 2013;127(10):1128-38. doi: 10.1161/CIRCULATIONAHA.112.000765. Epub Feb. 12, 2013.

Homma, et al. Involvement of RhoA/Rho kinase signaling in protection against monocrotaline-induced pulmonary hypertension in pneumonectomized rats by dehydroepiandrosterone. Am J Physiol Lung Cell Mol Physiol. 2008; 295:L71-8. DOI: 10.1152/ajplung.90251.200.

International search report and written opinion dated Jan. 9, 2015 for PCT/US2014/060039.

International search report and written opinion dated Jun. 20, 2014 for PCT/US2014/010778.

International search report and written opinion dated Nov. 20, 2014 for PCT/US2014/010773.

Jasmin, et al. Short-term administration of a cell-permeable caveolin-1 peptide prevents the development of monocrotaline-induced pulmonary hypertension and right ventricular hypertrophy. Circulation. Aug. 29, 2006;114(9):912-20.

Kanno, et al. Angiotensin-converting enzyme inhibitor preserves p21 and endothelial nitric oxide synthase expression in monocrotaline-induced pulmonary arterial hypertension in rats. Circulation. Aug. 21, 2001;104(8):945-50.

Kumada, et al. Phosphine-nickel complex catalyzed crosscoupling of grignard reagents with aryl and alkenyl halides: 1,2-dibutylbenezne.Organic Syntheses, Coll. vol. 6, p. 407 (1988); vol. 58, p. 127 (1978). DOI:10.15227/orgsyn.058.0127.

Kusano. Treatment for pulmonary hypertension including lung transplantation. Gen Thorac Cardiovasc Surg. Aug. 2011;59(8):538-46. doi: 10.1007/s11748-010-0747-z. Epub Aug. 18, 2011.

La Rosee, et al. Activity of the Bcr-Abl kinase inhibitor PD180970 against clinically relevant Bcr-Abl isoforms that cause resistance to imatinib mesylate (Gleevec, STI571). Cancer Res. Dec. 15, 2002;62(24):7149-53.

Laskowski, et al. PROCHECK: a program to check the sterochemical quality of protein structures. Journal of Applied Crystallography 1993;26:283-91.

(56) References Cited

OTHER PUBLICATIONS

Launay, et al. Survival in systemic sclerosis-associated pulmonary arterial hypertension in the modern management era. Ann Rheum Dis. Dec. 2013;72(12):1940-6. doi: 10.1136/annrheumdis-2012-202489. Epub Nov. 24, 2012.
Lee, et al. Monoclonal endothelial cell proliferation is present in primary but not secondary pulmonary hypertension. J Clin Invest. Mar. 1, 1998;101(5):927-34.
Leproult, et al. Cysteine mapping in conformationally distinct kinase nucleotide binding sites: application to the design of selective covalent inhibitors. J Med Chem. Mar. 10, 2011;54(5):1347-55. doi: 10.1021/jm101396q. Epub Feb. 15, 2011.
Lymboussaki, et al. Vascular endothelial growth factors and their receptors in embryos, adults and intumors. Academic Dissertation, University of Helsinki, Molecular/Cancer Biology Laboratory and Department of Pathology, Haartman Institute, (1999). 108 pages.
March. Advanced Organic Chemistry: Reactions, Mechanisms and Structure. 4th Ed. pp. 352-357, John Wiley & Sons, NY (1992).
Martinho, et al. Expression, mutation and copy number analysis of platelet-derived growth factor receptor A (PDGFRA) and its ligand PDGFA in gliomas. Br J Cancer. Sep. 15, 2009;101(6):973-82. doi: 10.1038/sj.bjc.6605225. Epub Aug. 25, 2009.
Masri, et al. Hyperproliferative apoptosis-resistant endothelial cells in idiopathic pulmonary arterial hypertension. Am J Physiol Lung Cell Mol Physiol. Sep. 2007;293(3):L548-54. Epub May 25, 2007.
Matsui, et al. Isolation of a novel receptor cDNA establishes the existence of two PDGF receptor genes. Science. Feb. 10, 1989;243(4892):800-4.
Maurya, et al. Structural models of vanadate-dependent haloperoxidases, their reactivity, immobilization on polymer support and catalytic activities. Journal of Chemical Sciences 123.2 (2011): 215-228.
McLaughlin. Classification and epidemiology of pulmonary hypertension. Cardiol Clin. Aug. 2004;22(3):327-41, v.
McLaughlin, et al. Pulmonary arterial hypertension. Curr Probl Cardiol. Dec. 2011;36(12):461-517. doi: 10.1016/j.cpcardiol.2011.08.002.
Medarametla, et al. PK10453, a nonselective platelet-derived growth factor receptor inhibitor, prevents the progression of pulmonary arterial hypertension. Pulm Circ. Mar. 2014;4(1):82-102. doi: 10.1086/674881.
Miyaura, et al. Palladium-Catalyzed Cross-Coupling Reactions of Organoboron Compounds. Chem. Rev.. 1995; 95(7):2457-2483.
Montani, et al. Pulmonary arterial hypertension. Orphanet J Rare Dis. Jul. 6, 2013;8:97. doi: 10.1186/1750-1172-8-97.
Montani, et al. Targeted therapies in pulmonary arterial hypertension. Pharmacol Ther. Feb. 2014;141(2):172-91. doi: 10.1016/j.pharmthera.2013.10.002. Epub Oct. 14, 2013.
Moren, et al. Aerosols in medicine : principles, diagnosis, and therapy. Amsterdam; New York: Elsevier, xx, 429 (1993).
Mustonen, et al. Endothelial receptor tyrosine kinases involved in angiogenesis. J Cell Biol. May 1995;129(4):895-8.
Negishi. A genealogy of Pd-catalyzed cross-coupling. Journal of organometallic chemistry 653.1 (2002): 34-40.
Oballa, et al. A generally applicable method for assessing the electrophilicity and reactivity of diverse nitrile-containing compounds. Bioorg Med Chem Lett. Feb. 15, 2007;17(4):998-1002. Epub Nov. 17, 2006.
Ogawa, et al. Inhibition of mTOR attenuates store-operated Ca2+ entry in cells from endarterectomized tissues of patients with chronic thromboembolic pulmonary hypertension. Am J Physiol Lung Cell Mol Physiol. Oct. 2009;297(4):L666-76. doi: 10.1152/ajplung.90548.2008. Epub Jul. 24, 2009.
Ogawa, et al. PDGF enhances store-operated Ca2+ entry by upregulating STIM1/Orai1 via activation of Akt/mTOR in human pulmonary arterial smooth muscle cells. Am J Physiol Cell Physiol. Jan. 15, 2012;302(2):C405-11. doi: 10.1152/ajpcell.00337.2011. Epub Oct. 26, 2011.
Paniaqua, et al. Imatinib for the treatment of rheumatic diseases. Nat Clin Pract Rheumatol. Apr. 2007;3(4):190-1.
Panzhinskiy, et al. Hypoxia induces unique proliferative response in adventitial fibroblasts by activating PDGFβ receptor-JNK1 signalling. Cardiovasc Res. Aug. 1, 2012;95(3):356-65. doi: 10.1093/cvr/cvs194. Epub Jun. 26, 2012.
Pao, et al. Acquired resistance of lung adenocarcinomas to gefitinib or erlotinib is associated with a second mutation in the EGFR kinase domain. PLoS Med. Mar. 2005;2(3):e73. Epub Feb. 22, 2005.
Perros, et al. Platelet-derived growth factor expression and function in idiopathic pulmonary arterial hypertension. Am J Respir Crit Care Med. Jul. 1, 2008;178(1):81-8. doi: 10.1164/rccm.200707-1037OC. Epub Apr. 17, 2008.
Phalen, et al. Inhalation exposure methodology. Environ Health Perspect. Jun. 1984;56:23-34.
Pinchuk, et al. Marine derived hamacanthins as lead for the development of novel PDGFRβ protein kinase inhibitors. Mar Drugs. Aug. 26, 2013;11(9):3209-23. doi: 10.3390/md11093209.
Pulido, et al. Macitentan and morbidity and mortality in pulmonary arterial hypertension. N Engl J Med. Aug. 29, 2013;369(9):809-18. doi: 10.1056/NEJMoa1213917.
Pulido, et al. Macitentan and pulmonary arterial hypertension. N Engl J Med. Jan. 2, 2014;370(1):82-3. doi: 10.1056/NEJMc1313112.
Rubin, et al. A paradigm shift in pulmonary arterial hypertension management. Eur Respir Rev. Dec. 2013;22(130):423-6. doi: 10.1183/09059180.00006913.
Sakagami, et al. In vivo, in vitro and ex vivo models to assess pulmonary absorption and disposition of inhaled therapeutics for systemic delivery. Adv Drug Deliv Rev. Oct. 31, 2006;58(9-10):1030-60. Epub Aug. 15, 2006.
Sakao, et al. Reversible or irreversible remodeling in pulmonary arterial hypertension. Am J Respir Cell Mol Biol. Dec. 2010;43(6):629-34. doi: 10.1165/rcmb.2009-0389TR. Epub Dec. 11, 2009.
Schermuly, et al. Reversal of experimental pulmonary hypertension by PDGF inhibition. J Clin Invest. Oct. 2005;115(10):2811-21.
Seferian, et al. Therapies for pulmonary arterial hypertension: where are we today, where do we go tomorrow? Eur Respir Rev. Sep. 1, 2013;22(129):217-26. doi: 10.1183/09059180.00001713.
Shah, et al. Overriding imatinib resistance with a novel ABL kinase inhibitor. Science. Jul. 16, 2004;305(5682):399-401.
Simonneau, et al. Updated clinical classification of pulmonary hypertension. J Am Coll Cardiol. Dec. 24, 2013;62(25 Suppl):D34-41. doi: 10.1016/j.jacc.2013.10.029.
Sitbon, et al. Upfront triple combination therapy in pulmonary arterial hypertension: a pilot study. Eur Respir J. Jun. 2014;43(6):1691-7. doi: 10.1183/09031936.00116313. Epub Mar. 13, 2014.
Smolich, et al. The antiangiogenic protein kinase inhibitors SU5416 and SU6668 inhibit the SCF receptor (c-kit) in a human myeloid leukemia cell line and in acute myeloid leukemia blasts. Blood. Mar. 1, 2001;97(5):1413-21.
Souza, et al. Long term imatinib treatment in pulmonary arterial hypertension. Thorax. Aug. 2006;61(8):736.
Stille. The Palladium-Catalyzed Cross-Coupling Reactions of Organotin Reagents with Organic Electrophiles [New Synthetic Methods (58)]. Angew. Chem. Int. Ed. Jun. 1986; 25(6):508-524.
Takatsuki, et al. Clinical safety, pharmacokinetics, and efficacy of ambrisentan therapy in children with pulmonary arterial hypertension. Pediatr Pulmonol. Jan. 2013;48(1):27-34. doi: 10.1002/ppul.22555. Epub Apr. 17, 2012.
Thompson, et al. Clustal W: improving the sensitivity of progressive multiple sequence alignment through sequence weighting, position-specific gap penalties and weight matrix choice. Nucleic Acids Res. Nov. 11, 1994;22(22):4673-80.
Tuder, et al. Plexiform lesion in severe pulmonary hypertension: association with glomeruloid lesion. Am J Pathol. Jul. 2001;159(1):382-3.
Ukrainets, et al. 2-Carbethoxymethyl-4H-3, 1-Benzoxazin-4-One. 3.* Condensation of o-Phenylenediamine. Khimiya Geterotsiklicheskikh Soedinii, 2, 239-241(1992).

(56) References Cited

OTHER PUBLICATIONS

Ukrainets, et al. 4-Hydroxy-2-Quinolones. 16.* Condensation of NR-Substituted Amides of 2-Carboxy-Malonanilic Acid Withoff-Phenylenediamine. translated from Khimiya Geterotsiklicheskikh Soedinii 8 (1993): 1105-1108.

Ukrainets, et al. 4-Hydroxy-2-quinolones. 32. Synthesis and antithyroid activity of thio analogs of 1H-2-oxo-3-(2-Benzimidazolyl)-4-hydroxyquinoline. Chemistry of Heterocyclic Compounds 33.5 (1997): 600-604.

Ukrainets, et al. 4-Hydroxy-2-Quinolones. 7.* Synthesis and Biological Properties of 1-R-3-(2-Benzimidazolyl)-4-Hydroxy-2-Quinolones. Khimiya Geterotsiklicheskikh Soedinii, 1, 105-108 (1993).

Ukrainets, et al. Effective synthesis of 3-(Benzimidazol-2-yl)-4-hydroxy-2-oxo-1, 2-dihydroquinolines. Tetrahedron letters 36.42 (1995): 7747-7748.

Ullrich, et al. Signal transduction by receptors with tyrosine kinase activity. Cell. Apr. 20, 1990;61(2):203-12.

Van Der Geer, et al. Receptor protein-tyrosine kinases and their signal transduction pathways. Annu Rev Cell Biol. 1994;10:251-337.

White, et al. Plexiform-like lesions and increased tissue factor expression in a rat model of severe pulmonary arterial hypertension. Am J Physiol Lung Cell Mol Physiol. Sep. 2007;293(3):L583-90. Epub Jun. 22, 2007.

Wu, et al. Comprehensive dissection of PDGF-PDGFR signaling pathways in PDGFR genetically defined cells. PLoS One. 2008;3(11):e3794. doi: 10.1371/journal.pone.0003794. Epub Nov. 24, 2008.

Yamamoto, et al. Activating mutation of D835 within the activation loop of FLT3 in human hematologic malignancies Blood. Apr. 15, 2001;97(8):2434-9.

Yang, et al. Prevalence of pulmonary arterial hypertension in patients with connective tissue diseases: a systematic review of the literature. Clin Rheumatol. Oct. 2013;32(10):1519-31. doi: 10.1007/s10067-013-2307-2. Epub Jun. 20, 2013.

Yeager, et al. Progenitor cells in pulmonary vascular remodeling. Pulm Circ. Jan.-Mar. 2011;1(1):3-16. doi: 10.4103/2045-8932.78095.

Yi, et al. Distribution of obstructive intimal lesions and their cellular phenotypes in chronic pulmonary hypertension. A morphometric and immunohistochemical study. Am J Respir Crit Care Med. Oct. 2000;162(4 Pt 1):1577-86.

Choy, G. et al., Safety, tolerability, and pharmacokinetics of amuvatinib from three phase 1 clinical studies in healthy volunteers, Cancer chemotherapy and pharmacology springer, Berlin, DE, 70(1); Feb. 15, 2012: 183-190, XP035077226, ISSN:1432-0843, DOI:10.1007/S00280-012-1821-2, Abstract, p. 184, paragraph investigational agent: amuvatinib.

Duret, C. et al., New respirable and fast dissolving itraconazole dry powder composition for the treatment of invasive pulmonary aspergillosis. Pharmaceutical research, Kluwer Academic publishers-plenum publishers, nl. 29(10); May 30, 2012: 2845-2859, XP03511465, ISSN:1573-904X, DOI:10.1007/S11095-012-0779-4. Abstract. p. 2847, Paragraph materials and ethods.

European Search Report dated Mar. 31, 2017 EP Application No. 14852309.5.

Notice of Allowance dated May 1, 2017 for U.S. Appl. No. 14/760,139.

Office Action dated Apr. 10, 2017 for U.S. Appl. No. 14/760,165.

A.

Figure showing lower IC50 of PK10467 compared to imatinib
And even lower IC50 PK10571 vs. 10467 and imatinib for inhibition of PDGFBB stimulated
Phosphorylation of AKT in fetal human lung fibroblasts.

B.

Figure: comparison of PK10453 and PK10571 with regard to PDGFBB stimulated phosphorylation Of AKT in fetal human lung fibroblasts. PK10571 has a lower IC50 for inhibition of PDGF BB stimulated phosphorylation of AKT

C.

Figure comparing PK10468 and PK10569 to imatinib; PK10468 and PK10569 are more potent inhibitors Of PDGF BB stimulated AKT phosphorylation in fetal human lung fibroblasts.

D.

The structures of PK10467, PK10468, PK10569, PK10453, and PK10571 are shown above, and are used as examples of non-selective and potent PDGF alpha receptor and PDGF beta receptor inhibitors.

Vehicle | Active

SPRAY-DRY FORMULATIONS

CROSS-REFERENCE TO RELATED APPLICATIONS

This application claims priority to U.S. Provisional Application No. 61/889,887 filed Oct. 11, 2013, the entire contents of which are hereby incorporated by reference in its entirety.

STATEMENT OF GOVERNMENT-SPONSORED RESEARCH

This invention was made with United States government support under Grant Number 1R43HL102946-01 and 2R44HL102946-02 awarded by the National Institute of Health. The United States government has certain rights in the invention.

FIELD OF THE INVENTION

The present disclosure relates generally to the treatment and prevention of disease associated with protein kinase activity. In particular, the present technology relates to therapeutic formulations of protein kinase inhibitors and methods for the treatment or prevention of pulmonary and vascular conditions, cancer, and other disorders.

BACKGROUND OF THE INVENTION

The following discussion of the background is merely provided to aid the reader in understanding the invention and does not necessarily describe or constitute prior art.

Receptor tyrosine kinases (RTKs) are transmembrane polypeptides that regulate the regeneration, remodeling, development and differentiation of cells and tissues. See, e.g., Mustonen et al., *J. Cell Biology* 129, 895-898 (1995); van der Geer et al. *Ann Rev. Cell Biol.* 10, 251-337 (1994). In addition to activating RTKs, polypeptide ligand growth factors and cytokines are capable of inducing conformation changes in RTK external domains which results in receptor dimerization. Lymboussaki, *Dissertation, Univ. of Helsinki, Mol./Cancer Bio Lab and Dept. of Pathology, Haartman Institute* (1999); Ullrich et al., *Cell* 61, 203-212 (1990). Cognate RTK receptor-ligand binding, moreover, imparts receptor trans-phosphorylation at specific tyrosine residues and subsequent activation of the kinase catalytic domains, thereby enabling substrate phosphorylation and activation of associated signaling cascades. Id.

Aberrant RTK activity, however, is associated with a variety of disease conditions and systemic delivery of certain RTK inhibitors have shown efficacy for specific disease conditions. In vivo assays to this end, including the murine monocrotaline (MCT) model system, have been employed for ascertaining whether putative RTK inhibitors would function as therapeutic agents. Concerning preclinical drug candidate efficacy, however, the MCT model has been criticized inasmuch as such a system fails to substantiate certain human disease phenotypes, e.g., the development of neointimal and/or plexiform lesions that are symptomatically comorbid with such diseases. Hence, this model is an imperfect system, which may confound the etiological and pathological indications of human disease. Thus, new or complementary model systems are necessary for accurate and efficient drug development.

In concert with the development and administration of first generation RTK inhibitors, e.g., imatinib, RTKs have evolved inhibitor resistance by acquiring certain mutations. See, e.g., Shah et al., *Science,* 305, 395-402 (2004). For example, in diseased patients refractory to certain kinase inhibitors, e.g., imatinib, it has been shown that the hydrophobic pocket "gatekeeper residue" frequently possesses mutations. See Pao et al., *PLos Med.* 2(3):e73 (2005). Such mutations have been identified with respect to ABL, i.e., at the T315 residue, and at analogous positions in KIT, PDGFRα, EGFR, and other kinases. Id. Hence, new RTK inhibitors with superior efficacy—developed in model systems that phenotypically resemble human disease pathology—are required for preventing and treating diseases possessing aberrant RTK activity.

SUMMARY OF THE INVENTION

In one aspect, the present disclosure provides a method of non-selective kinase receptor inhibition for treating pulmonary disorders in a subject, including: administering to the subject a therapeutically effective amount of a compound of Structure 1, a tautomer, enantiomer, isomer or stereoisomer of the compound, a pharmaceutically acceptable salt of the compound, tautomer, enantiomer, isomer or stereoisomer of the compound, or any mixtures thereof, where Structure 1 has the formula:

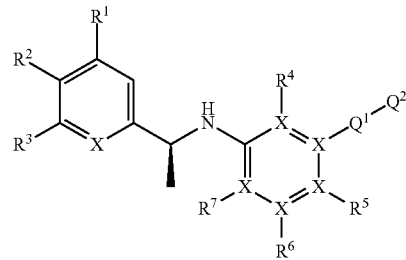

Structure 1

And where X is independently selected from C, N, O, S or —CN;

$R^1$, $R^2$, and $R^3$ may be the same or different and are independently selected from the group consisting of H, C, N, O, S, Cl, Br, F, I, —CN, —NO$_2$, —OH, —CH$_3$, —CF$_3$, —C—N—C— groups, —C—N—C(=O)— groups, —C(=O)R$^8$ groups, —N—C(=O)R$^8$ groups, —C—N—C(=O)R$^8$ groups, substituted and unsubstituted R$^8$ groups, substituted and unsubstituted R$^8$ groups substituted with one or more of R$^9$, R$^{10}$, and R$^{11}$, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups;

$R^4$, $R^5$, $R^6$, and $R^7$, may be the same or different and are independently selected from the group consisting of H, Cl, Br, F, I, —CN, —NO$_2$, —OH, —CH$_3$, —CF$_3$, —NH$_2$, —C≡N, —C═N groups, —C—N—C— groups, —C—N—C(═O)— groups, —C—N—C(═O)—C—F, —C—N—C(═O)—C═C, substituted and unsubstituted alkyl groups, substituted and unsubstituted aryl groups, substituted and unsubstituted heterocyclyl groups, alkoxy groups, aryloxy groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl) amino groups, —C(═O)H, —C(═O)-alkyl groups, —C(═O)-aryl groups, —C(═O)O-alkyl groups, —C(═O)O-aryl groups, —C(═O)NH$_2$, —C(═O)NH(alkyl) groups, —C(═O)NH(aryl) groups, —C(═O)N(alkyl)$_2$ groups, —C(═O)-aryl groups, —C(═O)NH$_2$, —C(═O)NH(alkyl) groups, —C(═O)NH(aryl) groups, —C(═O)N(alkyl)$_2$ groups, C(═O)N(aryl)$_2$ groups, —C(═O)N(alkyl)(aryl) groups, —C(═O)O-alkyl groups, —C(═O)O-aryl groups, —C(═O)-heterocyclyl groups, —C(═O)—O-heterocyclyl groups, —C(═O)NH(heterocyclyl) groups, —C(═O)—N(heterocyclyl)$_2$ groups, —C(═O)—N(alkyl)(heterocyclyl) groups, —C(═O)—N(aryl)(heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups, substituted and unsubstituted diheterocyclylaminoalkyl, substituted and unsubstituted (heterocyclyl)(alkyl)aminoalkyl, substituted and unsubstituted (heterocyclyl) (aryl)aminoalkyl, substituted and unsubstituted alkoxyalkyl groups, substituted and unsubstituted hydroxyalkyl groups, substituted and unsubstituted aryloxyalkyl groups, and substituted and unsubstituted heterocyclyloxyalkyl groups; -(alkyl)(aryl)aminoalkyl groups, —C(═O)-heterocyclyl groups, —C(═O)—O-heterocyclyl groups, —C(═O)NH(heterocyclyl) groups, —C(═O)—N (heterocyclyl)$_2$ groups, —C(═O)—N(alkyl)(heterocyclyl) groups, —C(═O)—N(aryl)(heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted and unsubstituted alkyl groups, substituted and unsubstituted aryl groups, substituted and unsubstituted alkoxy groups, substituted and unsubstituted aryloxy groups, substituted and unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups;

$R^8$ is selected from the group consisting of $R^1$, $R^2$, $R^3$, $R^4$, $R^5$, $R^6$, $R^7$, H, absent, —C═C, substituted and unsubstituted heterocyclyl groups, substituted and unsubstituted aryl groups, substituted and unsubstituted heterocyclyl($R^9$) groups, substituted and unsubstituted heterocyclyl($R^{10}$) groups, substituted and unsubstituted heterocyclyl($R^{11}$) groups, substituted and unsubstituted)heterocyclyl($R^9$)($R^{10}$) groups, substituted and unsubstituted)heterocyclyl($R^9$)($R^{11}$) groups, substituted and unsubstituted)heterocyclyl($R^9$)($R^{10}$) groups, substituted and unsubstituted heterocyclyl($R^9$)($R^{10}$)($R^{11}$) groups, substituted and unsubstituted —C(═O)-heterocyclyl($R^9$) groups, substituted and unsubstituted —C(═O)-heterocyclyl($R^{10}$) groups, substituted and unsubstituted —C(═O)-heterocyclyl($R^{11}$) groups, substituted and unsubstituted —C(═O)-heterocyclyl($R^9$)($R^{10}$) groups, substituted and unsubstituted —C(═O)-heterocyclyl ($R^9$)($R^{10}$) groups, substituted and unsubstituted)-C(═O)-heterocyclyl ($R^{10}$)($R^{11}$) groups, substituted and unsubstituted —C(═O)-heterocyclyl($R^9$)($R^{10}$)($R^{11}$) groups, substituted and unsubstituted aryl($R^9$) groups, substituted and unsubstituted aryl ($R^{10}$) groups, substituted and unsubstituted aryl ($R^{11}$) groups, substituted and unsubstituted aryl)($R^9$)($R^{10}$) groups, substituted and unsubstituted aryl ($R^9$)($R^{11}$) groups, substituted and unsubstituted)aryl($R^{10}$)($R^{11}$) groups, substituted and unsubstituted aryl ($R^9$)($R^{10}$)($R^{11}$) groups, substituted and unsubstituted —C(═O)-aryl($R^9$) groups, substituted and unsubstituted)-C(═O)-aryl($R^{10}$) groups, substituted and unsubstituted —C(═O)-aryl($R^{11}$) groups, substituted and unsubstituted —C(═O)-aryl($R^9$)($R^{10}$) groups, groups, substituted and unsubstituted —C(═O)-aryl($R^9$)($R^{11}$) substituted and unsubstituted C(═O)-aryl($R^{10}$)($R^{11}$) groups, and substituted/unsubstituted —C(═O)-aryl($R^9$)($R^{10}$)($R^{11}$) groups;

$R^9$, $R^{10}$, and $R^{11}$ may be the same or different and are independently selected from the group consisting of absent, H, Cl, Br, F, I, —CN, —NO$_2$, —OH, —CH$_3$, —CF$_3$, —NH$_2$, —C(═O)—, —C—N—$R^{12}$, —C≡N, —C—N—C groups, —C—N—C(═O)— groups, —C—N—C(═O)—C—F, —C—N—C(═O)—C═C, —C═N groups, substituted and unsubstituted alkyl groups, substituted and unsubstituted aryl groups, substituted and unsubstituted heterocyclyl groups, alkoxy groups, aryloxy groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, and substituted and unsubstituted dialkylamino groups, substituted and unsubstituted aminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl)amino groups, —C(═O)H, —C(═O)-alkyl groups, —C(═O)-aryl groups, —C(═O)O-alkyl groups, —C(═O)O-aryl groups, —C(═O)NH$_2$, —C(═O)NR(alkyl) groups, —C(═O)NH(aryl) groups, —C(═O)N(alkyl)$_2$ groups, —C(═O)-aryl groups, —C(═O)NH$_2$, —C(═O)NH(alkyl) groups, —C(═O)NH (aryl) groups, —C(═O)N(alkyl)$_2$ groups, —C(═O)N (aryl)$_2$ groups, —C(═O)N(alkyl)(aryl) groups, —C(═O)O-alkyl groups, —C(═O)O-aryl groups, —C(═O)-heterocyclyl groups, —C(═O)—O-heterocyclyl groups, —C(═O)NH(heterocyclyl) groups, —C(═O)—N(heterocyclyl)$_2$ groups, —C(═O)—N(alkyl)(heterocyclyl) groups, —C(═O)—N (aryl)(heterocyclyl) groups, substituted and unsubstituted heterocyclylaminoalkyl groups, substituted and unsubstituted cyano groups, substituted and unsubstituted pyrimidinyl groups, substituted and unsubstituted cyano(aryl) groups, substituted and unsubstituted cyano (heterocyclyl) groups, and substituted and unsubstituted cyano-pyrimidinyl groups;

$R^{12}$ is selected from the group consisting of absent, H, Cl, Br, F, I, —CN, —NO$_2$, —OH, —CH$_3$, —CF$_3$, —NH$_2$, —C(=O)—, —C—N—R$^{12}$, —C≡N, —C—N—C groups, —C—N—C(=O)— groups, —C—N—C(=O)—C—F, —C—N—C(=O)—C=C, —C=N groups, —C(=O)— groups, —C(=O)—C— groups, —C(=O)—C=C, —S(=O)$_2$— groups, —S(=O)$_2$—C— groups, —S(=O)$_2$—C=C— groups, —S(=O)$_2$—C=C—CH$_3$, alkoxy groups, aryloxy groups, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups;

$Q^1$ is selected from the group consisting of a direct bond, H, C, Cl, Br, F, I, —CN, —NO$_2$, —OH, —CH$_3$, —CF$_3$, —NH$_2$, —C(=O)—, —C—N—R$^{12}$, —C≡N, —C—N—C groups, —C—N—C(=O)— groups, —C—N—C(=O)—C—F, —C—N—C(=O)—C=C, —C=N groups, —C(=O)— groups, —C(=O)—C— groups, —C(=O)—C=C, —CF$_3$, —C≡N, —C—N—C— groups, —C—N—C(=O)— groups, —C—N—C(=O)—C—F, —C—N—C(=O)—C=C, —OH, alkoxy groups, aryloxy groups, substituted and unsubstituted alkyl groups, substituted and unsubstituted aryl groups, substituted and unsubstituted heterocyclyl groups, alkoxy groups, aryloxy groups, methoxy groups, dimethoxy groups, methoxy phenol, methoxy phenol groups, dimethoxy phenol, dimethoxy phenol groups, dimethoxy benzene, dimethoxy benzene groups, methoxymethyl benzyl groups, substituted and unsubstituted aralkyl groups, —NH$_2$, substituted and unsubstituted heterocyclylalkyl groups, substituted/unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, and substituted and unsubstituted dialkylamino groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups;

$Q^2$ is selected from the groups consisting of absent, H, $Q^1$, $Q^1(Q^3)$, —OH, alkoxy groups, aryloxy groups; and $Q^3$ is selected from the group consisting of absent, a direct bond, H, C, Cl, Br, F, I, —CN, —NO$_2$, —CH$_3$, —CF$_3$, —NH$_2$, —C(=O)—, —C—N—R$^{12}$, —C≡N, —C—N—C groups, —C—N—C(=O)— groups, —C—N—C(=O)—C—F, —C—N—C(=O)—C=C, —C=N groups, —C(=O)— groups, —C(=O)—C— groups, —C(=O)—C=C, —CF$_3$, —C≡N, —C—N—C— groups, —C—N—C(=O)— groups, —C—N—C(=O)—C—F, —C—N—C(=O)—C=C, —OH, alkoxy groups, alkoxy groups, aryloxy groups, methoxy groups, dimethoxy groups, methoxy phenol, methoxy phenol groups, dimethoxy phenol, dimethoxy phenol groups, dimethoxy benzene, dimethoxy benzene groups, substituted and unsubstituted alkyl groups, substituted and unsubstituted aryl groups, and substituted and unsubstituted heterocyclyl groups. The contents of the foregoing paragraph are hereinafter referred to as "QXR".

In illustrative embodiments, the structure of $R^8$ has the following formula:

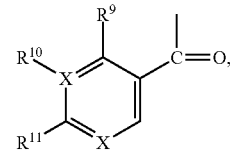

where X is independently selected from C, N, O, S, and —CN;

$R^9$, $R^{10}$, and $R^{11}$ may be the same or different and are independently selected from the group consisting of H, C, N, O, S, Cl, Br, F, I, —CN, —NO$_2$, —OH, —CH$_3$, —CF$_3$, —NH$_2$, —C(=O)—, —C—N—R$^{12}$, —C≡N, —C—N—C(=O)—C—F, —C—N—C(=O)—C=C, substituted and unsubstituted alkyl groups, substituted and unsubstituted aryl groups, substituted and unsubstituted heterocyclyl groups, —OH, alkoxy groups, aryloxy groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, and substituted and unsubstituted dialkylamino groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups; and $R^{12}$ is selected from the group consisting of —C(=O)— groups, —C(=O)—C— groups, —C(=O)—C=C, —S(=O)$_2$— groups, —S(=O)$_2$—C— groups, —S(=O)$_2$—C=C— groups, —S(=O)$_2$—C=C—CH$_3$, —OH, alkoxy groups, aryloxy groups, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted diallglaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups. The contents of the foregoing paragraph are hereinafter referred to as "QXR2".

In illustrative embodiments, the structure of R8 is selected from Group A as shown.

Group A structures

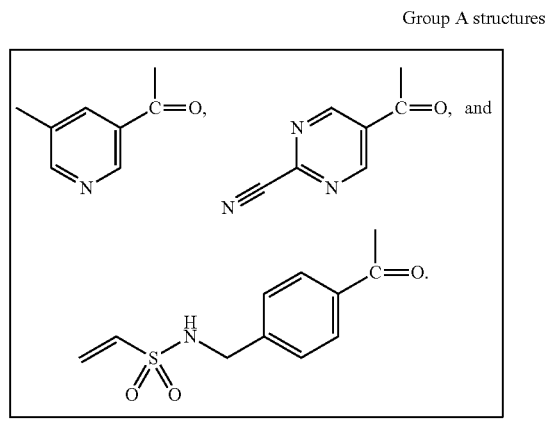

In illustrative embodiments, the structure of Q1 or Q2 is selected from Group B as shown below, —CH3, —OH, —O—CH3, —C—N—C(=O)—C=C, and —C—N—C(=O)—C—F.

Group B structures

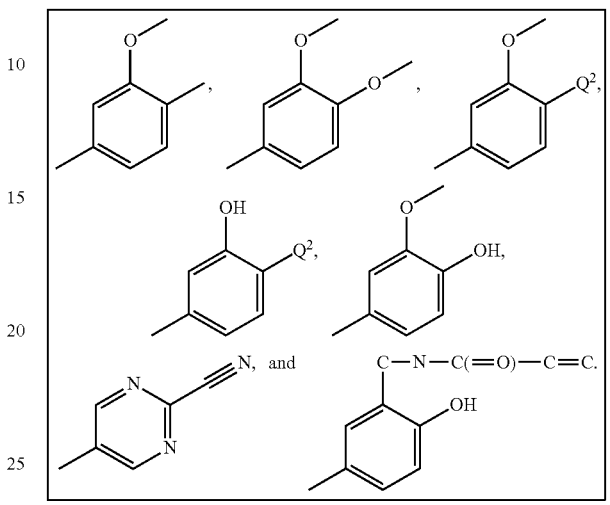

In some embodiments, the compound of Structure 1 is a compound of Structure 2, 2a, 3, 4 or 5, as shown below in Group C.

Group C structures

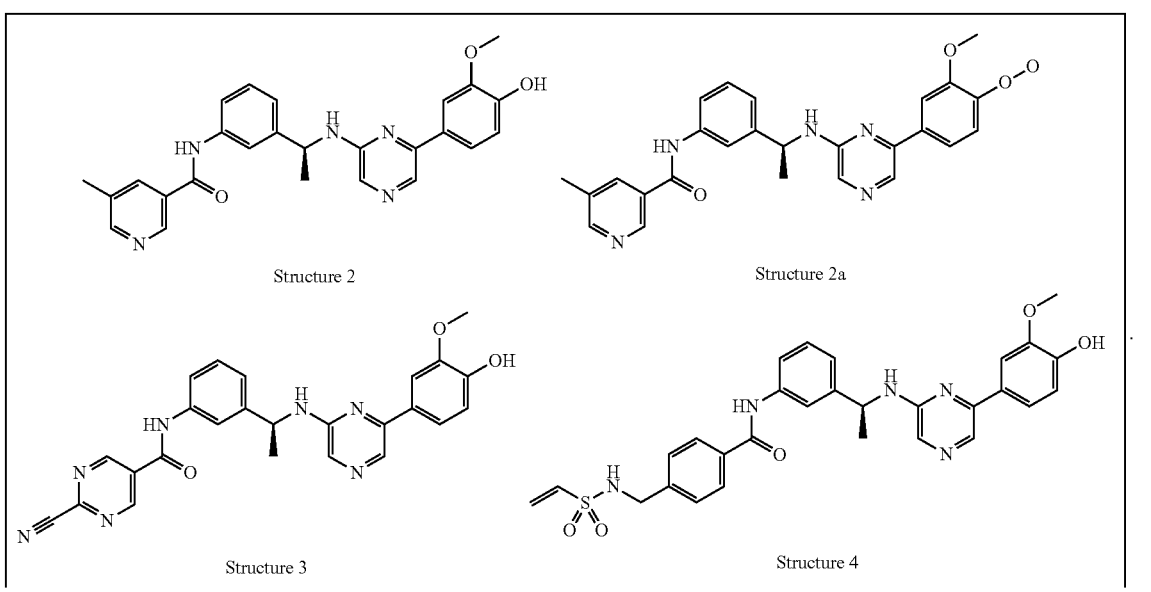

-continued

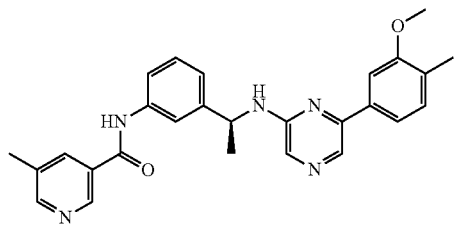

Structure 5

In illustrative embodiments, the compound of Structure 1, 2, 2a, 3, 4 or 5 is administered orally, intravenously, subcutaneously, transdermally, intraperitoneally, or by inhalation. In illustrative embodiments, the kinase receptor is a receptor tyrosine kinase (RTK), and wherein the RTK is platelet derived growth factor receptor (PDGFR). In illustrative embodiments, the PDGFR is platelet derived growth factor receptor-alpha (PDGFR-α) or platelet derived growth factor receptor-beta (PDGFR-β) or both. In illustrative embodiments, the PDGFR is a homodimer or heterodimer selected from PDGFR-αα, PDGFR-ββ and PDGFR-αβ, or any combination thereof. In illustrative embodiments, the inhibition of the PDGFR is effective in treating the pulmonary disorder, where the pulmonary disorder is pulmonary arterial hypertension (PAH), PAH associated with plexiform and/or neointimal lesions, PAH associated with pulmonary fibrosis and/or progressive vaso-degeneration, abnormal fibroblast and/or myofibroblast proliferation, or pulmonary vascular disorders associated with abnormal endothelial cell proliferation, or any combination thereof.

In illustrative embodiments, the inhibition is a combined inhibition of both the PDGFR-α and the PDGFR-β. In illustrative embodiments, the inhibition prevents activation of both the PDGFR-α and the PDGFR-β by modulating cognate substrate interactions. In illustrative embodiments, the cognate substrate is selected from PDGFAA, PDGFBB and PDGFAB, or any combination thereof. In illustrative embodiments, the pulmonary disorder is selected from pulmonary arterial hypertension (PAH), PAH associated with plexiform and/or neointimal lesions, PAH associated with pulmonary fibrosis and/or progressive vasodegeneration, abnormal fibroblast and/or myofibroblast proliferation, and pulmonary vascular disorders associated with abnormal endothelial cell proliferation.

In illustrative embodiments, the PAH selected from primary PAH, idiopathic PAH, heritable PAH, refractory PAH, BMPR2, ALK1, endoglin associated with hereditary hemorrhagic telangiectasia, endoglin not associated with hereditary hemorrhagic telangiectasia, drug-induced PAH, and toxin-induced PAH, PAH associated with systemic sclerosis, mixed connective tissue disease, HIV, hepatitis, and/or portal hypertension.

In illustrative embodiments, the PAH is secondary to pulmonary hypertension, congenital heart disease, hypoxia, chronic hemolytic anemia, newborn persistent pulmonary hypertension, pulmonary veno-occlusive disease (PVOD), pulmonary capillary hemangiomatosis (PCH), left heart disease pulmonary hypertension, systolic dysfunction, diastolic dysfunction, valvular disease, lung disease, interstitial lung disease, pulmonary fibrosis, schistosomiasis, chronic obstructive pulmonary disease (COPD), sleep-disordered breathing, alveolar hypoventilation disorders, chronic exposure to high altitude, developmental abnormalities, chronic thromboembolic pulmonary hypertension (CTEPH), pulmonary hypertension with unclear multifactorial mechanisms, hematologic disorders, myeloproliferative disorders, splenectomy, systemic disorders, sarcoidosis, pulmonary Langerhans cell histiocytosis, lymphangioleimoyomatosis, neurofibromatosis, vasculitis, metabolic disorders, glycogen storage disease, Gaucher disease, thyroid disorders, tumoral obstruction, fibrosing mediastinitis, and/or chronic renal failure on dialysis.

In illustrative embodiments, the pulmonary disorder is associated with abnormal: right ventricular systolic pressure (RVSP); pulmonary pressure; cardiac output; right ventricular (RV) hypertrophy; and/or pulmonary arterial (PA) hypertrophy. In illustrative embodiments, the compound of Structure 1 possesses an $IC_{50}$ of less than 300 nM for the kinase receptor. In illustrative embodiments, the kinase receptor is platelet derived growth factor receptor-alpha (PDGFR-α) or platelet derived growth factor receptor-beta (PDGFR-β) or both, and where the pulmonary disorder is pulmonary arterial hypertension. In illustrative embodiments, the inhibition occurs through a non-covalent interaction. In illustrative embodiments, the inhibition occurs through a covalent interaction.

In one aspect, the present disclosure provides a method of treating pulmonary arterial hypertension (PAH) in a subject, including: modulating the phosphorylation-state of one or more downstream targets of platelet derived growth factor receptor-alpha (PDGFR-α) or platelet derived growth factor receptor-beta (PDGFR-β) or both, where the downstream target is any substrate phosphorylated as a result of the PDGFR-α and/or the PDGFR-β activation, by administering to the subject a compound of Structure 1, a tautomer, enantiomer, isomer or stereoisomer of the compound, a pharmaceutically acceptable salt of the compound, tautomer, enantiomer, isomer or stereoisomer of the compound, or any mixtures thereof, where the downstream target is selected from the group consisting of AKT, PDGFR, STAT3, ERK1 and ERK2, or any other downstream target of the PDGFR-α and/or the PDGFR-β, and where the compound of Structure 1 has the following formula:

Structure 1

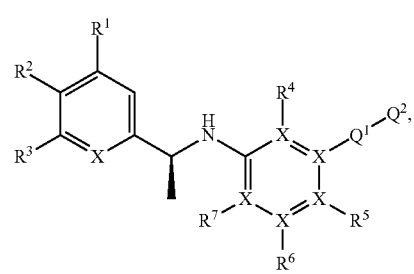

where X is independently selected from C, N, O, S or —CN;

$R^1$, $R^2$, and $R^3$ may be the same or different and are independently selected from the group consisting of H, C, N, O, S, Cl, Br, F, I, —CN, —NO₂, —OH, —CH₃, —CF₃, —C—N—C— groups, —C—N—C(=O)— groups, —C(=O)R⁸ groups, —N—C(=O)R⁸ groups, —C—N—C(=O)R⁸ groups, substituted and unsubstituted R⁸ groups, substituted and unsubstituted R⁸ groups substituted with one or more of $R^9$, $R^{10}$, and $R^{11}$, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups;

$R^4$, $R^5$, $R^6$, and $R^7$, may be the same or different and are independently selected from the group consisting of H, Cl, Br, F, I, —CN, —NO₂, —OH, —CH₃, —CF₃, —NH₂, —C≡N, —C=N groups, —C—N—C— groups, —C—N—C(=O)— groups, —C—N—C(=O)—C—F, —C—N—C(=O)—C=C, substituted and unsubstituted alkyl groups, substituted and unsubstituted aryl groups, substituted and unsubstituted heterocyclyl groups, alkoxy groups, aryloxy groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl) amino groups, —C(=O)H, —C(=O)-alkyl groups, —C(=O)-aryl groups, —C(=O)O-alkyl groups, —C(=O)O-aryl groups, —C(=O)NH₂, —C(=O)NH(alkyl) groups, —C(=O)NH(aryl) groups, —C(=O)N(alkyl)₂ groups, —C(=O)-aryl groups, —C(=O)NH₂, —C(=O)NH(alkyl) groups, —C(=O)NH(aryl) groups, —C(=O)N(alkyl)₂ groups. —C(=O)N(aryl)₂ groups, —C(=O)N(alkyl)(aryl) groups, —C(=O)O-alkyl groups, —C(=O)O-aryl groups, —C(=O)-heterocyclyl groups, —C(=O)—O-heterocyclyl groups, —C(=O)NH(heterocyclyl) groups, —C(=O)—N(heterocyclyl)₂ groups, —C(=O)—N(alkyl)(heterocyclyl) groups, —C(=O)—N(aryl) (heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups, substituted and unsubstituted diheterocyclylaminoalkyl, substituted and unsubstituted (heterocyclyl)(alkyl)aminoalkyl, substituted and unsubstituted (heterocyclyl) (aryl)aminoalkyl, substituted and unsubstituted alkoxyalkyl groups, substituted and unsubstituted hydroxyalkyl groups, substituted and unsubstituted aryloxyalkyl groups, and substituted and unsubstituted heterocyclyloxyalkyl groups; -(alkyl)(aryl)aminoalkyl groups, —C(=O)-heterocyclyl groups, —C(=O)—O-heterocyclyl groups, —C(=O)NH(heterocyclyl) groups, —C(=O)—N (heterocyclyl)₂ groups, —C(=O)—N(alkyl) (heterocyclyl) groups, —C(=O)—N(aryl) (heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups, —NH(alkyl) groups, —NH(aryl) groups, —N(alkyl)₂ groups, —N(aryl)₂ groups, —N(alkyl)(aryl) groups, —NH (heterocyclyl) groups, —N(heterocyclyl)(alkyl) groups, —N(heterocyclyl)(aryl) groups, —N(heterocyclyl)₂ groups, substituted and unsubstituted alkyl groups, substituted and unsubstituted aryl groups, substituted and unsubstituted alkoxy groups, substituted and unsubstituted aryloxy groups, substituted and unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups;

where the structure of $R^8$ has the following formula:

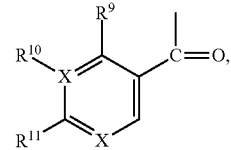

and where X is independently selected from C, N, O, S, or —CN;

$R^9$, $R^{10}$, and $R^{11}$ may be the same or different and are independently selected from the group consisting of H, C, N, O, S, Cl, Br, F, I, —CN, —NO₂, —OH, —CH₃, —CF₃, —NH₂, —C(=O)—, —C—N—R¹², —C≡N, —C—N—C(=O)—C—F, —C—N—C(=O)—C=C, substituted and unsubstituted alkyl groups, substituted and unsubstituted aryl groups, substituted and unsubstituted heterocyclyl groups, —OH, alkoxy groups, aryloxy groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl) aminoalkyl groups, substituted and unsubstituted alkylamino groups, substituted and unsubstituted arylamino groups, and substituted and unsubstituted dialkylamino groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups;

$R^{12}$ is selected from the group consisting of —C(=O)— groups, —C(=O)—C— groups, —C(=O)—C=C, —S(=O)₂— groups, —S(=O)₂—C— groups, —S(=O)₂—C=C— groups, —S(=O)₂—C=C—CH₃, —OH, alkoxy groups, aryloxy groups, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups; and where the structure of $Q^1$ or $Q^2$ is selected from the group consisting of —CH$_3$, —OH, —O—CH$_3$, —C—N—C (=O)—C=C, —C—N—C(=O)—C—F,

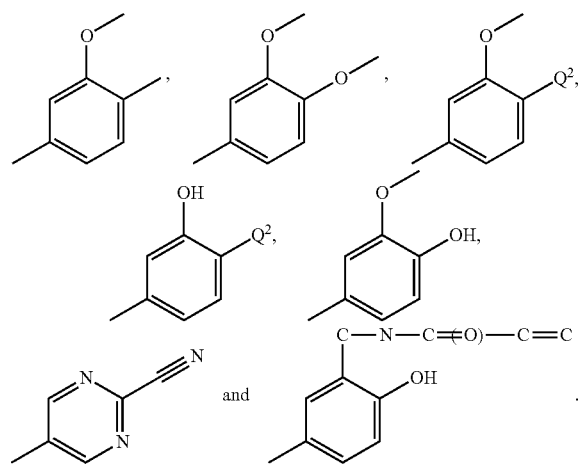

The entire contents of the foregoing paragraph are hereinafter referred to as "QXR3"

In illustrative embodiments, the structure of R8 is selected from the Group A structures noted above in the Summary. In illustrative embodiments, the modulation is a decrease of phosphorylated STAT3 to total STAT3, diphosphorylated ERK1 to total ERK1, diphosphorylated ERK2 to total ERK2, monophosphorylated ERK1 to total ERK1, phosphorylated PDGFR to total PDGFR, or phosphorylated AKT to total AKT, or any combination thereof, in the subject compared to the PSR in the subject before the administering. In illustrative embodiments, the compound of Structure 1 interacts with AKT at residues Thr308 and/or Ser473, or where the compound of Structure 1 interacts with one or more of the PDGFR-α, PDGFR-β, PDGFR-αα, PDGFR-ββ, and/or the PDGFR-αβ amino acids selected from LYS627, VAL607, GLU644, MET648, HIS816, LEU809, ASP836, CYS814, ILE834, CYS835, PHE937, LYS634, VAL614, GLU651, MET655, HIS824, LEU817, ASP844, CYS822, ILE842, VAL658, ILE647, HIS816, ARG836, LYS634, GLU651, ALA632, HIS824, MET655, ARG825, CYS843, THR874, ARG817, VAL815, LEU651, LEU809, ILE657, THR681, ILE654, ARG825, ASP826, LEU658, LEU825, PHE837, LEU658, HIS824, CYS814, ILE654, ASP844, ILE842, and/or CYS843, or any combination thereof.

In some embodiments, the compound of Structure 1 is a compound selected from the Group C structures noted above in the Summary. In illustrative embodiments, the inhibition occurs through a non-covalent interaction. In illustrative embodiments, the inhibition occurs through a covalent interaction. In illustrative embodiments, compound of Structure 1, a tautomer, enantiomer, isomer or stereoisomer of the compound, a pharmaceutically acceptable salt of the compound, tautomer, enantiomer, isomer or stereoisomer of the compound, or any mixtures thereof, for treating one or more diseases associated with hyperproliferation, neoplasia, hypoplasia, hyperplasia, dysplasia, metaplasia, prosoplasia, desmoplasia, angiogenesis, inflammation, immunological state, metabolism, pulmonary function, and cardiovascular function by non-selectively inhibiting a receptor tyrosine kinase (RTK) selected from AKT, c-Kit, and/or PDGFR, where Structure 1 is as follows:

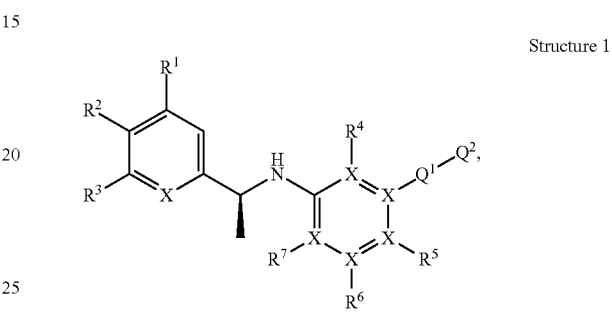

Structure 1 where X, $R^1$, $R^2$, $R^3$, $R^4$, $R^5$, $R^6$, $R^7$ (and c, $R^9$, $R^{10}$, $R^{11}$ and $R^{12}$, as contained therein), $Q^1$ and $Q^2$ (and $Q^3$ as contained therein) are selected from "XRQ3" as noted above.

In illustrative embodiments, the structure of $R^8$ is selected from the Group A structures noted above on the Summary. In some embodiments, the compound is a structure selected from the Group C structures noted above in the Summary.

In illustrative embodiments, the compound of Structure 1 is administered orally, intravenously, subcutaneously, transdermally, intraperitoneally, or by inhalation. In illustrative embodiments, the disease is selected from the group consisting of cancer, metastatic cancer, HIV, hepatitis, PAH, primary PAH, idiopathic PAH, heritable PAH, refractory PAH, BMPR2, ALK1, endoglin associated with hereditary hemorrhagic telangiectasia, endoglin not associated with hereditary hemorrhagic telangiectasia, drug-induced PAH, and toxin-induced PAH, PAH associated with systemic sclerosis, and mixed connective tissue disease, pulmonary hypertension, congenital heart disease, hypoxia, chronic hemolytic anemia, newborn persistent pulmonary hypertension, pulmonary veno-occlusive disease (PVOD), pulmonary capillary hemangiomatosis (PCH), left heart disease pulmonary hypertension, systolic dysfunction, diastolic dysfunction, valvular disease, lung disease, interstitial lung disease, pulmonary fibrosis, schistosomiasis, COPD, sleep-disordered breathing, alveolar hypoventilation disorders, chronic exposure to high altitude, developmental abnormalities, chronic thromboembolic pulmonary hypertension (CTEPH), pulmonary hypertension with unclear multifactorial mechanisms, hematologic disorders, myeloproliferative disorders, splenectomy, systemic disorders, sarcoidosis, pulmonary Langerhans cell histiocytosis, lymphangioleimoyomatosis, neurofibromatosis, metabolic disorders, glycogen storage disease, Gaucher disease, thyroid disorders, tumor obstruction, fibrosing mediastinitis, and chronic renal failure on dialysis.

In illustrative embodiments, the salt is a chloride, hydrochloride, sulfate, phosphate, mesylate, bismesylate, tosylate, lactate, tartrate, malate, bis-acetate, citrate, or bishydrochloride salt. In illustrative embodiments, the inhibition occurs through a non-covalent interaction. In some embodiments, the inhibition occurs through a covalent interaction. In some embodiments, compound of Structure 1 possesses an $IC_{50}$ of less than 300 nM for the kinase receptor. In illustrative embodiments, the treatment methods result in one or more of improved exercise capacity, improved functional class, less shortness of breath, decreased hospitalization, decreased need for lung transplantation, decreased need for atrial septostomy, and increased longevity or overall survival. In some embodiments, the improved exercise capacity is an increased 6 minute walk distance. In suitable embodiments, improved functional class is an improvement from class IV to class III, II or I, or an improvement from class III to class II or I, or an improvement form class II to class I.

In some embodiments, a spray dry powder formulation of PK10571 (free base or salt form) with excipient leucine suitable for inhalation such that an effective dose is delivered for the treatment of a disease is disclosed. A spray dry powder formulation of PK10571 (free base or salt form) with excipients trehalose and leucine suitable for inhalation, in certain embodiments, is described such that an effective dose is delivered for the treatment of a disease. A non-selective PDGF receptor kinase inhibitor (approximately equally potent against both the PDGFR alpha receptor and PDGFR beta receptor) is described in some embodiments as a formulated spray dry powder with leucine or leucine/trehalose suitable for inhalation such that an effective dose is delivered for the treatment of a disease, where the disease is WHO group 1 pulmonary arterial hypertension; the disease is WHO group 3 PAH (PAH associated with intestinal lung disease or pulmonary fibrosis).

In one aspect, the present invention is a composition comprising an excipient and a non-selective receptor tyrosine kinase (RTK) inhibitor compound of Structure 1, a tautomer, enantiomer, isomer or stereoisomer of the compound, a pharmaceutically acceptable salt of the compound, tautomer, enantiomer, isomer or stereoisomer of the compound, or any mixtures thereof, wherein the composition is a dry powder, and wherein Structure 1 has the following formula:

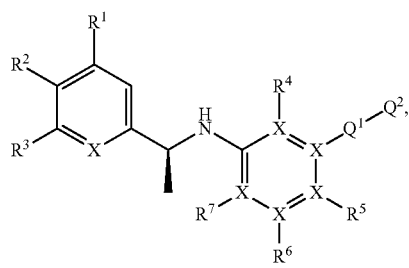

Structure 1 wherein X is independently selected from C, N, O, S or —CN;

$R^1$, $R^2$, and $R^3$ may be the same or different and are independently selected from the group consisting of H, C, N, O, S, Cl, Br, F, I, —CN, —NO$_2$, —OH, —CH$_3$, —CF$_3$, —C—N—C— groups, —C—N—C(=O)— groups, —C(=O)R$^8$ groups, —N—C(=O)R$^8$ groups, —C—N—C(=O)R$^8$ groups, N—C(=O)—N—R$^8$, substituted and unsubstituted R$^8$ groups, substituted and unsubstituted urea groups, substituted and unsubstituted R$^8$ groups substituted with one or more of R$^9$, R$^{10}$, and R$^{11}$, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups; $R^4$, $R^5$, $R^6$, and $R^7$, may be the same or different and are independently selected from the group consisting of H, Cl, Br, F, I, —CN, —NO$_2$, —OH, —CH$_3$, —CF$_3$, —NH$_2$, —C≡N, —C=N groups, —C—N—C— groups, —C—N—C(=O)— groups, —C—N—C(=O)—C—F, —C—N—C(=O)—C=C, substituted and unsubstituted alkyl groups, substituted and unsubstituted aryl groups, substituted and unsubstituted heterocyclyl groups, alkoxy groups, aryloxy groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups, substituted and unsubstituted diheterocyclylaminoalkyl, substituted and unsubstituted (heterocyclyl)(alkyl)aminoalkyl, substituted and unsubstituted (heterocyclyl)(aryl)aminoalkyl, substituted and unsubstituted alkoxyalkyl groups, substituted and unsubstituted hydroxyalkyl groups, substituted and unsubstituted aryloxyalkyl groups, and substituted and unsubstituted heterocyclyloxyalkyl groups; -(alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl) (heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups, —NH(alkyl) groups, —NH(aryl) groups, —N(alkyl)₂ groups, —N(aryl)₂ groups, —N(alkyl)(aryl) groups, —NH(heterocyclyl) groups, —N(heterocyclyl)(alkyl) groups, —N(heterocyclyl)(aryl) groups, —N(heterocyclyl)₂ groups, substituted and unsubstituted alkyl groups, substituted and unsubstituted aryl groups, substituted and unsubstituted alkoxy groups, substituted and unsubstituted aryloxy groups, substituted and unsubstituted heterocyclyl groups, —NHOH, —N(alkyl)OH groups, —N(aryl)0H groups, —N(alkyl)O-alkyl groups, —N(aryl)O-alkyl groups, —N(alkyl)O-aryl groups, and —N(aryl)O-aryl groups; wherein the structure of $R^8$ has the following formula:

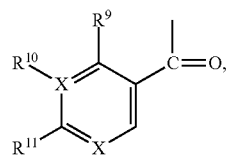

and wherein X is independently selected from C, N, O, S, or —CN;

$R^9$, $R^{10}$, and $R^{11}$ may be the same or different and are independently selected from the group consisting of H, C, N, O, S, Cl, Br, F, I, —CN, —NO₂, —OH, —CH₃, —CF₃, —NH₂, —C(═O)—, —C—N—$R^{12}$, —C≡N, —C—N—C(═O)—C—F, —C—N—C(═O)—C═C, substituted and unsubstituted alkyl groups, substituted and unsubstituted aryl groups, substituted and unsubstituted heterocyclyl groups, —OH, alkoxy groups, aryloxy groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, and substituted and unsubstituted dialkylamino groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups; $R^{12}$ is selected from the group consisting of —C(═O)— groups, —C(═O)—C— groups, —C(═O)—C═C, —S(═O)₂— groups, —S(═O)₂—C— groups, —S(═O)₂—C═C— groups, —S(═O)₂—C═C—CH₃, —OH, alkoxy groups, aryloxy groups, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups; and wherein the structure of $Q^1$ or $Q^2$ is selected from the group consisting of Group B structures, —CH₃, —OH, —O—CH₃, —C—N—C(═O)—C═C, and —C—N—C(═O)—C—F, and Cl (chloride).

In some embodiments, the dry powder is a spray-dried powder. In illustrative embodiments, the compound listed in Chart A/FIG. 1. In illustrative embodiments, the receptor tyrosine kinase is selected from the group consisting of AKT, c-Kit, and platelet derived growth factor receptor (PDGFR). In illustrative embodiments, the receptor tyrosine kinase is PDGFR. In illustrative embodiments, the PDGFR is platelet derived growth factor receptor-alpha (PDGFR-α) or platelet derived growth factor receptor-beta (PDGFR-β) or both. In illustrative embodiments, the PDGFR is a homodimer or heterodimer selected from the group consisting of PDGFR-αα, PDGFR-ββ and PDGFR-αβ, or any combination thereof. In illustrative embodiments, the excipient comprises a hydrophobic amino acid. In illustrative embodiments, the hydrophobic amino acid is selected from the group consisting of: tryptophan, tyrosine, leucine, trileucine, isoleucine, and phenylalanine.

In illustrative embodiments, the hydrophobic amino acid is leucine. In illustrative embodiments, the hydrophobic amino acid is L-leucine. In illustrative embodiments, the hydrophobic amino acid is present in an amount ranging from 20-60% or more, and/or 10-95% by weight of the composition. In illustrative embodiments, the excipient comprises a carbohydrate bulking agent. In illustrative embodiments, the carbohydrate bulking agent is selected from the group consisting of: lactose, mannitol, trehalose, raffinose, or a maltodextrin. In illustrative embodiments, the carbohydrate bulking agent is trehalose. In illustrative embodiments, the excipient comprises a hydrophobic amino acid and a carbohydrate bulking agent. In illustrative embodiments, the excipient comprises leucine and trehalose. In illustrative embodiments, the dry powder comprises particles having a mass median aerodynamic diameter of less than or equal to about 5 μm. In illustrative embodiments, at least 50% of the particles have a mass median aerodynamic diameter of less than about 5 μm.

In illustrative embodiments, at least 50% of the particles have a mass median aerodynamic diameter of less that about 3 μm. In illustrative embodiments, at least 50% of the particles have a mass median aerodynamic diameter of less that about 3 μm. In illustrative embodiments, the dry powder has a moisture content below about 5% by water weight. In illustrative embodiments, the dry powder is substantially amorphous. In illustrative embodiments, the dry powder has a glass transition temperature of greater than 50 degrees Celsius. In illustrative embodiments, the dry powder has a glass transition temperature of greater than 90 degrees Celsius. In illustrative embodiments, the pH of reconstituted powder is greater than 3. In illustrative embodiments, the median TMAX value in arterial or venous plasma is 1-60 minutes. In illustrative embodiments, the AUC value range is 100000-400000 ng/ml*min. In illustrative embodiments, the mean maximum blood plasma concentration of the compound ($C_{MAX}$) is within the range of about 100-3000 ng/ml.

In illustrative embodiments, the terminal half-life of the compound when delivered by inhalation ranges from 100-300 minutes. In illustrative embodiments, the emitted dose is 40% or more.

In illustrative embodiments, the bioavailability via inhalation is about 10% or more. In illustrative embodiments, the salt is a chloride, hydrochloride, sulfate, phosphate, mesylate, bismesylate, tosylate, lactate, tartrate, malate, his-acetate, citrate, or bishydrochloride salt. In illustrative embodiments, the composition is formulated as a free base. In illustrative embodiments, the compound of Structure 1 possesses an IC50 of less than 300 nM for the kinase receptor. In illustrative embodiments, the excipient is a phospholipid. In illustrative embodiments, the excipient 1,2-Distearoyl-sn-glycero-3-phosphocholine (DSPC). In illustrative embodiments, the excipient is DSPC in combination with a amount of calcium chloride to attain an acceptable glass transition temperature. In illustrative embodiments, at least 50% of the particles have a mass median aerodynamic diameter of less that about 3 µm. In illustrative embodiments, the dry powder is delivered by a dry powder inhaler.

In one aspect, the present invention is a method of treating a disease comprising: (a) selecting a subject in need of treatment; and (b) administering a therapeutically effective amount of a dry powder formulation of spray-dried particles prepared from a feedstock comprising a hydrophobic excipient selected from the group consisting of lactose, mannitol, trehalose, raffinose, maltodextrin, tryptophan, tyrosine, leucine, trileucine, isoleucine, phenylalanine, and DSPC, or any combination thereof, wherein the particles comprise a non-selective receptor tyrosine kinase (RTK) inhibitor compound of Structure 1, a tautomer, enantiomer, isomer or stereoisomer of the compound, a pharmaceutically acceptable salt of the compound, tautomer, enantiomer, isomer or stereoisomer of the compound, or any mixtures thereof, wherein Structure 1 has the following formula:

Structure 1 wherein X is independently selected from C, N, O, S or —CN;

$R^1$, $R^2$, and $R^3$ may be the same or different and are independently selected from the group consisting of H, C, N, O, S, Cl, Br, F, I, —CN, —NO$_2$, —OH, —CH$_3$, —CF$_3$, —C—N—C— groups, —C—N—C(=O)— groups, —C(=O)R$^8$ groups, —N—C(=O)R$^8$ groups, —C—N—C(=O)R$^8$, N—C(=O)—N—R$^8$ groups, substituted and unsubstituted R$^8$ groups, substituted and unsubstituted R$^8$ groups substituted with one or more of R$^9$, R$^{10}$, and R$^{11}$, substituted and unsubstituted amidinyl groups, substituted and unsubstituted urea groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups; $R^4$, $R^5$, $R^6$, and $R^7$, may be the same or different and are independently selected from the group consisting of H, Cl, Br, F, I, —CN, —NO$_2$, —OH, —CH$_3$, —CF$_3$, —NH$_2$, —C=N groups, —C—N—C— groups, —C—N—C (=O)— groups, —C—N—C(=O)—C—F, —C—N—C (=O)—C=C, substituted and unsubstituted alkyl groups, substituted and unsubstituted aryl groups, substituted and unsubstituted heterocyclyl groups, alkoxy groups, aryloxy groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl) amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, —C(=O)-heterocyclyl groups, —C(=O)—O-heterocyclyl groups, —C(=O)NH(heterocyclyl) groups, —C(=O)—N (heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups, substituted and unsubstituted diheterocyclylaminoalkyl, substituted and unsubstituted (heterocyclyl)(alkyl)aminoalkyl, substituted and unsubstituted (heterocyclyl)(aryl)aminoalkyl, substituted and unsubstituted alkoxyalkyl groups, substituted and unsubstituted hydroxyalkyl groups, substituted and unsubstituted aryloxyalkyl groups, and substituted and unsubstituted heterocyclyloxyalkyl groups; -(alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl) (heterocyclyl) groups, —C(=O)—N(aryl) (heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups, —NH(alkyl) groups, —NH(aryl) groups, —N(alkyl)$_2$ groups, —N(aryl)$_2$ groups, —N(alkyl)(aryl) groups, —NH (heterocyclyl) groups, —N(heterocyclyl)(alkyl) groups, —N(heterocyclyl)(aryl) groups, —N(heterocyclyl)$_2$ groups, substituted and unsubstituted alkyl groups, substituted and unsubstituted aryl groups, substituted and unsubstituted alkoxy groups, substituted and unsubstituted aryloxy groups, substituted and unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups; wherein the structure of $R^8$ has the following formula:

and wherein X is independently selected from C, N, O, S, or —CN;

$R^9$, $R^{10}$, and $R^{11}$ may be the same or different and are independently selected from the group consisting of H, C, N, O, S, Cl, Br, F, I, —CN, —NO$_2$, —OH, —CH$_3$, —CF$_3$, —NH$_2$, —C(=O)—, —C—N—R$^{12}$, —C≡N, —C—N—C (=O)—C—F, —C—N—C(=O)—C=C, substituted and unsubstituted alkyl groups, substituted and unsubstituted aryl groups, substituted and unsubstituted heterocyclyl groups, —OH, alkoxy groups, aryloxy groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl) aminoalkyl groups, substituted and unsubstituted alkylamino groups, substituted and unsubstituted arylamino groups, and substituted and unsubstituted dialkylamino groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups; $R^{12}$ is selected from the group consisting of —C(=O)— groups, —C(=O)—C— groups, —C(=O)—C=C, —S(=O)$_2$— groups, —S(=O)$_2$—C— groups, —S(=O)$_2$—C=C— groups, —S(=O)$_2$—C=C—CH$_3$, —OH, alkoxy groups, aryloxy groups, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups; and wherein the structure of $Q^1$ or $Q^2$ is selected from the group consisting of Group B structures, —CH$_3$, —OH, —O—CH$_3$, —C—N—C(=O)—C=C, and —C—N—C(=O)—C—F.

In illustrative embodiments, the compound is listed in Chart A/FIG. 1. In illustrative embodiments, the receptor tyrosine kinase is selected from the group consisting of AKT, c-Kit, and platelet derived growth factor receptor (PDGFR). In illustrative embodiments, the receptor tyrosine kinase is PDGFR. In illustrative embodiments, the PDGFR is platelet derived growth factor receptor-alpha (PDGFR-α) or platelet derived growth factor receptor-beta (PDGFR-β) or both. In illustrative embodiments, the PDGFR is a homodimer or heterodimer selected from the group consisting of PDGFR-αα, PDGFR-ββ and PDGFR-αβ, or any combination thereof. In illustrative embodiments, In illustrative embodiments, the excipient comprises leucine and trehalose. In illustrative embodiments, the dry powder comprises particles having a mass median aerodynamic diameter of less than or equal to about 5 μm. In illustrative embodiments, at least 40% of the particles have a mass median aerodynamic diameter of less than about 3 μm. In illustrative embodiments, the dry powder has a moisture content below about 5% by water weight. In illustrative embodiments, the dry powder is substantially amorphous.

In illustrative embodiments, the pH of reconstituted powder is greater than 3. In illustrative embodiments, the median TMAX value is 1-60 minutes or more. In illustrative embodiments, the median AUC value is 100000-400000 ng/ml*min. In illustrative embodiments, the mean maximum blood plasma concentration of the compound (CMAX) is within the range of about 100-3000 ng/ml. In illustrative embodiments, the half-life of the compound ranges from 100-300 minutes when delivered by inhalation. In illustrative embodiments, the emitted is 40% or more. In illustrative embodiments, the bioavailability by inhalation is 10% or more. In illustrative embodiments, the dry powder is encapsulated in a capsule. In illustrative embodiments, the salt is a chloride, hydrochloride, sulfate, phosphate, mesylate, bismesylate, tosylate, lactate, tartrate, malate, bis-acetate, citrate, fumarate, bromate or bishydrochloride salt. In illustrative embodiments, the composition is formulated as a free base. In illustrative embodiments, the compound of Structure 1 possesses an IC50 of less than 300 nM for the kinase receptor. In illustrative embodiments, the dry powder composition is administered to the subject via pulmonary administration.

In illustrative embodiments, a dry powder inhaler is used to administer the dry powder composition. In illustrative embodiments, the dry powder inhaler is a capsule-based dry powder inhaler. In illustrative embodiments, the capsule-based dry powder inhaler is a monodose inhaler. In illustrative embodiments, the disease is pulmonary arterial hypertension (PAH) and the PAH is selected from the group consisting of primary PAH, idiopathic PAH, heritable PAH, refractory PAH, BMPR2, ALK1, endoglin associated with hereditary hemorrhagic telangiectasia, endoglin not associated with hereditary hemorrhagic telangiectasia, drug-induced PAH, and toxin-induced PAH, PAH associated with systemic sclerosis, mixed connective tissue disease, HIV, hepatitis, and portal hypertension.

In illustrative embodiments, the PAH is secondary to pulmonary hypertension, congenital heart disease, hypoxia, chronic hemolytic anemia, newborn persistent pulmonary hypertension, pulmonary veno-occlusive disease (PVOD), pulmonary capillary hemangiomatosis (PCH), left heart disease pulmonary hypertension, systolic dysfunction, diastolic dysfunction, valvular disease, lung disease, interstitial lung disease, pulmonary fibrosis, schistosomiasis, chronic obstructive pulmonary disease (COPD), sleep-disordered breathing, alveolar hypoventilation disorders, chronic exposure to high altitude, developmental abnormalities, chronic thromboembolic pulmonary hypertension (CTEPH), pulmonary hypertension with unclear multifactorial mechanisms, hematologic disorders, myeloproliferative disorders, splenectomy, systemic disorders, sarcoidosis, pulmonary Langerhans cell histiocytosis, lymphangioleimoyomatosis, neurofibromatosis, vasculitis, metabolic disorders, glycogen storage disease. Gaucher disease, thyroid disorders, tumoral obstruction, fibrosing mediastinitis, and chronic renal failure on dialysis.

In illustrative embodiments, the disease is selected from the group consisting of cancer, metastatic cancer, HIV, hepatitis, PAH, primary PAH, idiopathic PAH, heritable PAH, refractory PAH, BMPR2, ALK1, endoglin associated with hereditary hemorrhagic telangiectasia, endoglin not associated with hereditary hemorrhagic telangiectasia, drug-induced PAH, and toxin-induced PAH, PAH associated with systemic sclerosis, and mixed connective tissue disease, pulmonary hypertension, congenital heart disease, hypoxia, chronic hemolytic anemia, newborn persistent pulmonary hypertension, pulmonary veno-occlusive disease (PVOD), pulmonary capillary hemangiomatosis (PCH), left heart disease pulmonary hypertension, systolic dysfunction, diastolic dysfunction, valvular disease, lung disease, interstitial lung disease, pulmonary fibrosis, schistosomiasis, COPD, sleep-disordered breathing, alveolar hypoventilation disorders, chronic exposure to high altitude, developmental abnormalities, chronic thromboembolic pulmonary hypertension (CTEPH), pulmonary hypertension with unclear multifactorial mechanisms, hematologic disorders, myeloproliferative disorders, splenectomy, systemic disorders, sarcoidosis, pulmonary Langerhans cell histiocytosis, lymphangioleimoyomatosis, neurofibromatosis, vasculitis, metabolic disorders, glycogen storage disease, Gaucher disease, thyroid disorders, tumoral obstruction, fibrosing mediastinitis, and chronic renal failure on dialysis.

In illustrative embodiments, the treating comprises improving the World Health Organization (WHO) functional PAH classification of a subject, and wherein the improvement is from class IV to class III, II or I, or an improvement from class III to class II or I, or an improvement form class II to class I. In illustrative embodiments, the inhibition is effective in treating one or more of a pulmonary disorder, pulmonary arterial hypertension (PAH), PAH associated with plexiform and/or neointimal lesions, PAH associated with pulmonary fibrosis and/or progressive vasodegeneration, PAH associated with interstitial lung disease or pulmonary fibrosis, abnormal fibroblast and/or myofibroblast proliferation, or pulmonary vascular disorders associated with abnormal endothelial cell proliferation, or any combination thereof.

In one aspect, the present invention is a method of preparing a dry powder formulation of spray-dried particles comprising: (a) preparing a feedstock comprising: (i) a non-selective receptor tyrosine kinase (RTK) inhibitor compound of Structure 1, a tautomer, enantiomer, isomer or stereoisomer of the compound, a pharmaceutically acceptable salt of the compound, tautomer, enantiomer, isomer or stereoisomer of the compound, or any mixtures thereof—, and (ii) a hydrophobic excipient selected from the group consisting of tryptophan, tyrosine, leucine, trileucine, isoleucine and phenylalanine, a s O-aryl groups, —C(=O)NH$_2$, —C(=O)NH(alkyl) groups, —C(=O)NH(aryl) groups, —C(=O)N(alkyl)$_2$ groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups, substituted and unsubstituted diheterocyclylaminoalkyl, substituted and unsubstituted (heterocyclyl)(alkyl)aminoalkyl, substituted and unsubstituted (heterocyclyl)(aryl)aminoalkyl, substituted and unsubstituted alkoxyalkyl groups, substituted and unsubstituted hydroxyalkyl groups, substituted and unsubstituted aryloxyalkyl groups, and substituted and unsubstituted heterocyclyloxyalkyl groups; -(alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl) (heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted and unsubstituted alkyl groups, substituted and unsubstituted aryl groups, substituted and unsubstituted alkoxy groups, substituted and unsubstituted aryloxy groups, substituted and unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups; wherein the structure of R$^8$ has the following formula:

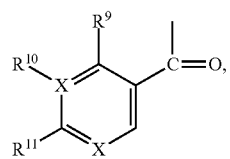

and wherein X is independently selected from C, N, O, S, or —CN;
R$^9$, R$^{10}$, and R$^{11}$ may be the same or different and are independently selected from the group consisting of H, C, N, O, S, Cl, Br, F, I, —CN, —NO$_2$, —OH, —CH$_3$, —CF$_3$, —NH$_2$, —C(=O)—, —C—N—R$^{12}$, —C≡N, —C—N—C(=O)—C—F, —C—N—C(=O)—C=C, substituted and unsubstituted alkyl groups, substituted and unsubstituted aryl groups, substituted and unsubstituted heterocyclyl groups, —OH, alkoxy groups, aryloxy groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, and substituted and unsubstituted dialkylamino groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups; R$^{12}$ is selected from the group consisting of —C(=O)— groups, —C(=O)—C— groups, —C(=O)—C=C, —S(=O)$_2$— groups, —S(=O)$_2$—C— groups, —S(=O)$_2$—C=C— groups, —S(=O)$_2$—C=C—CH$_3$, —OH, alkoxy groups, aryloxy groups, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted cyano groups, substituted and unsubstituted pyrimidinyl groups, substituted and unsubstituted cyano(aryl) groups, substituted and unsubstituted cyano(heterocyclyl) groups, and substituted and unsubstituted cyano-pyrimidinyl groups; and wherein the structure of Q$^1$ or Q$^2$ is selected from the group consisting of Group B structures, —CH$_3$, —OH, —O—CH$_3$, —C—N—C(=O)—C=C, and —C—N—C(=O)—C—F. In illustrative embodiments, the compound of structure 1 is a compound listed in Chart A/FIG. 1. In illustrative embodiments, the disease is selected from the group consisting of parenchymal lung disease, interstitial lung disease, pulmonary fibrosis, and pulmonary hypertension associated with pulmonary fibrosis. In illustrative embodiments, the disease is treated with one or more compounds of structure 1.

BRIEF DESCRIPTION OF THE FIGURES

FIG. 1A shows that the IC$_{50}$ of Imatinib against PDGFRα is 71 nM, while FIG. 1B shows an IC$_{50}$ for PK10453 against PDGFRα of 35 nM. FIG. 1C, furthermore, shows that the IC$_{50}$ of Imatinib for PDGFRβ is 607 nM, while FIG. 1D shows an IC$_{50}$ for PK10453 against PDGFRβ of 10.1 nM.

FIGS. 2A-B show that PDGFAA stimulation of pAKT(S473) and pAKT(T308), respectively, in HLFs were blocked by PK10453 (■) and Imatinib (▲) with a comparable IC$_{50}$ between 0.3-0.6 μM. FIG. 2C shows that PDGFBB stimulation of pAKT(Ser473) was blocked by PK10453 (■) with an IC$_{50}$ of 0.13 μM compared to 1.8 μM for Imatinib (▲). FIG. 2D shows that PDGFBB stimulation of pAKT(Thr308) was blocked by PK10453 (■) with an IC$_{50}$ of 0.43 μM compared to 3.25 μM for imatinib (▲). FIG. 2E shows examples of ICWs for PDGFAA and PDGFBB stimulated AKT phosphorylation, PK10453 vs. Imatinib.

The signal at 800 nm is color coded green and represents the phospho-protein specific signal; the signal at 700 nm is color coded red and represents signal from total AKT. As shown, the 800 and 700 nm signals are superimposed (§p<0.01; * p<0.001).

Figure 3:
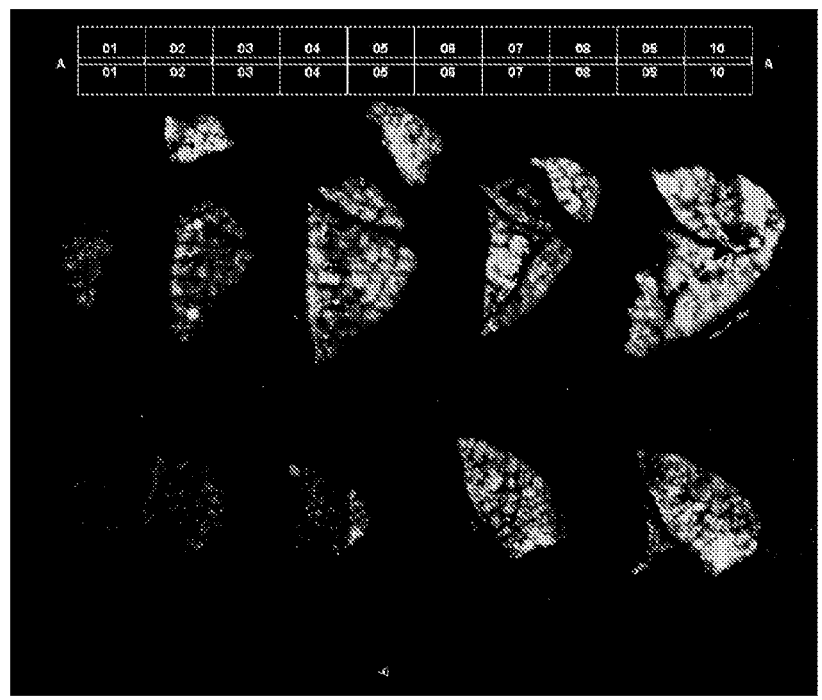

FIG. 3 depicts fluorescence images of frozen rat lung sections (right upper, middle, and lower lobes) after 2 min of PK10453 (Structure 2) and IR780 tracer inhalation. Image acquisition occurred at 800 nm (green), which is the λ of IR780 detection, while image acquisition at 700 nm (red) represents tissue autofluorescence. Digital ruler intervals are show (1 cm).

Figure 4:
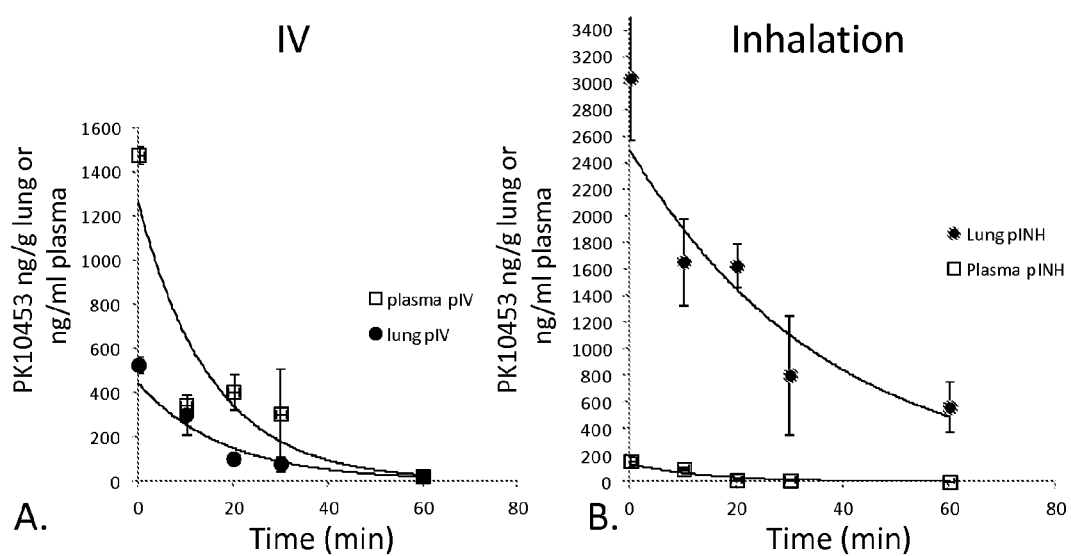

FIG. 4 shows graphic data for intravenous (IV) and inhaled (INH) PK10453 (Structure 2). FIG. 4A is a pharmacokinetic (PK) graph concerning IV administered PK10453 and associated concentrations in the lungs and plasma as a function of time. FIG. 4B is a PK graph concerning INH administered PK10453 and associated levels in the lungs and plasma per time.

Figure 5:
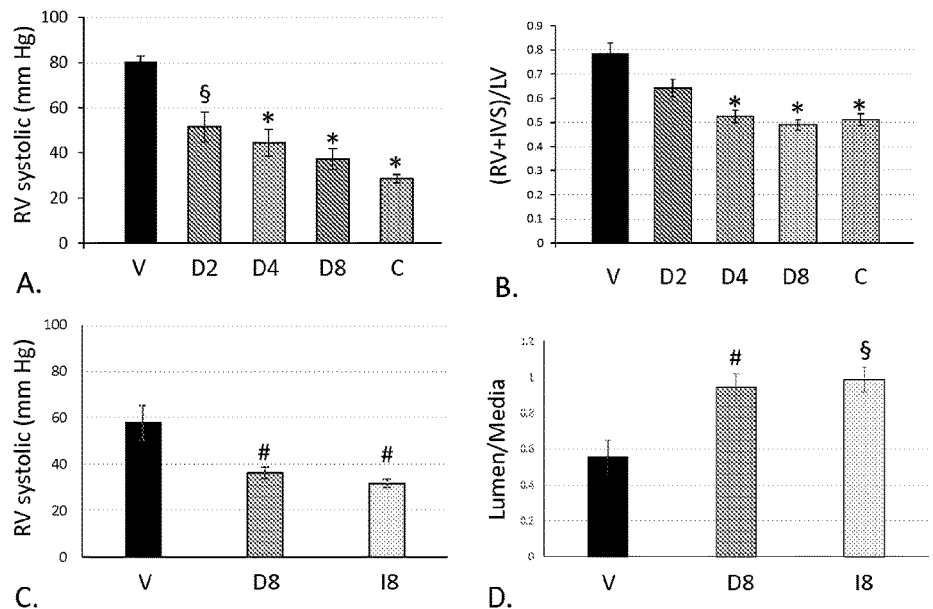

FIG. 5 depicts the effect of PK10453 (Structure 2) on right ventricle (RV) systolic pressure and RV hypertrophy in the MCT and MCT+PN model systems. FIG. 5A is a graph showing the effect of PK10453 on RV systolic pressure in the MCT model, where C (n=3), V (n=2), D2 (n=6), D4 (n=6), and D8 (n=5) respectively represent control, vehicle, 2 min exposure, 4 min exposure, and 8 min exposure times, for two weeks, three times daily. Asterisks (*) indicate p<0.001 and section symbols (§) indicate p<0.05. FIG. 5B is a graph showing the effect of PK10453 on RV hypertrophy in the MCT model, where inhalation treatments were initiated three weeks after administration of MCT. C, D2, D4, and D8 respectively represent controls, 2, 4, and 8 min exposure times, for two weeks three times daily. The asterisks (*) indicate p<0.001. FIG. 5C is a graph showing the effect of PK10453 on RV systolic pressure (RVSP) in the rat MCT model: comparison of PK10453 to imatinib; # p<0.01. FIG. 5D shows the Lumen/Media ratio in the MCT model of PK10453, Imatinib and vehicle: Vehicle (V, n=4): 0.55±0.1; PK10453 (D8, n=12): 0.94±0.08; Imatinib (I8, n=5): 0.99±0.07; §p<0.05, # p<0.01.

Figure 6:
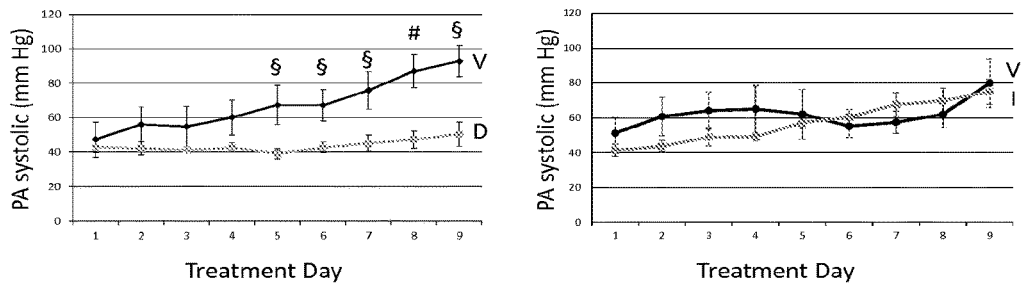

FIG. 6 shows graphs for telemetry studies in the rat MCT+PN model. FIG. 6A is a graph showing pulmonary artery systolic pressure measured over time in ambulatory subjects using the MCT+PN model system with PK10453. V (n=5) and D4 (n=6) respectively represent vehicle and 4 min exposure to PK10453 (Structure 2) three times daily. Asterisks (*) indicate p<0.001 and section symbols (§) indicate p<0.01. FIG. 6B is a graph showing pulmonary artery systolic pressure measured over time in ambulatory subjects using the MCT+PN model system with Imatinib. V=vehicle; I=Imatinib (p=NS).

Figure 7:
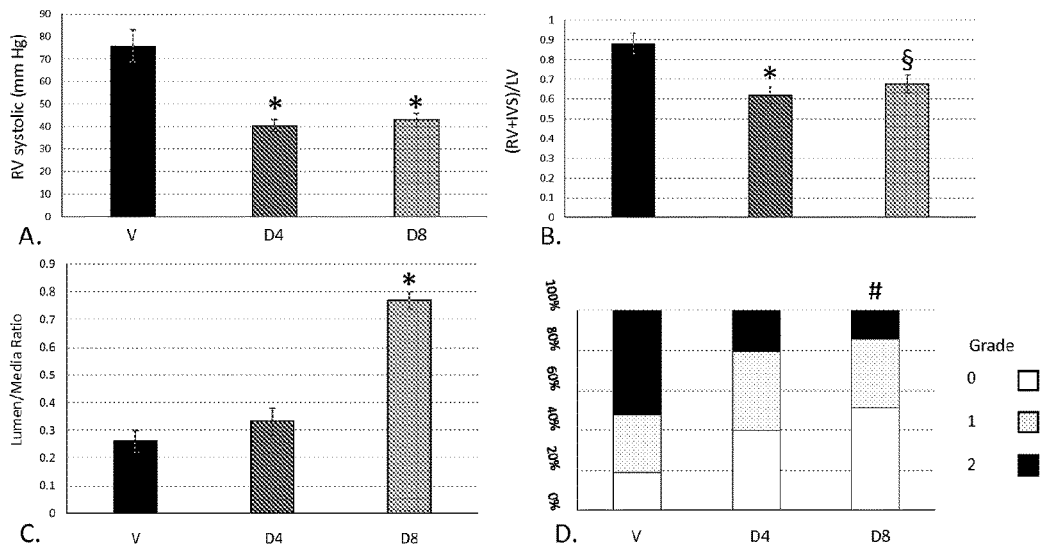

FIG. 7 represents graphs relating to hemodynamic and morphometric analyses in the rat MCT+PN model. FIG. 7A shoes that RV systolic pressure: V (n=9) RVS, 75.7±7.1 mm Hg, D4 group (n=10) RVS 40.4±2.7 mm Hg, D8 (n=8) RVS 43±3.0 mm Hg (p<0.001 V vs. D4 and V vs. D8). FIG. 7B shows RV hypertrophy was decreased by treatment with PK10453 (Structure 2); (RV+IVS)/LV ratio: V (n=11); D4 (n=13); D8 (n=7); *p<0.001, §p<0.05. FIG. 7C shows the rat MCT+PN model, the lumen area/media area ratio was greater in the D8 (n=5) treated groups compared to PK10453 D4 (n=6) and vehicle (n=6); *p<0.0001 D8 vs. V, D8 vs. D4. FIG. 7D shows occlusion analyses, which were performed on the same animal samples used for the lumen/media ratio analysis. The occlusion analysis showed a significant decrease in Grade 2 (>50% occlusive) lesions in the D8 group (#p<0.01).

Figure 8:
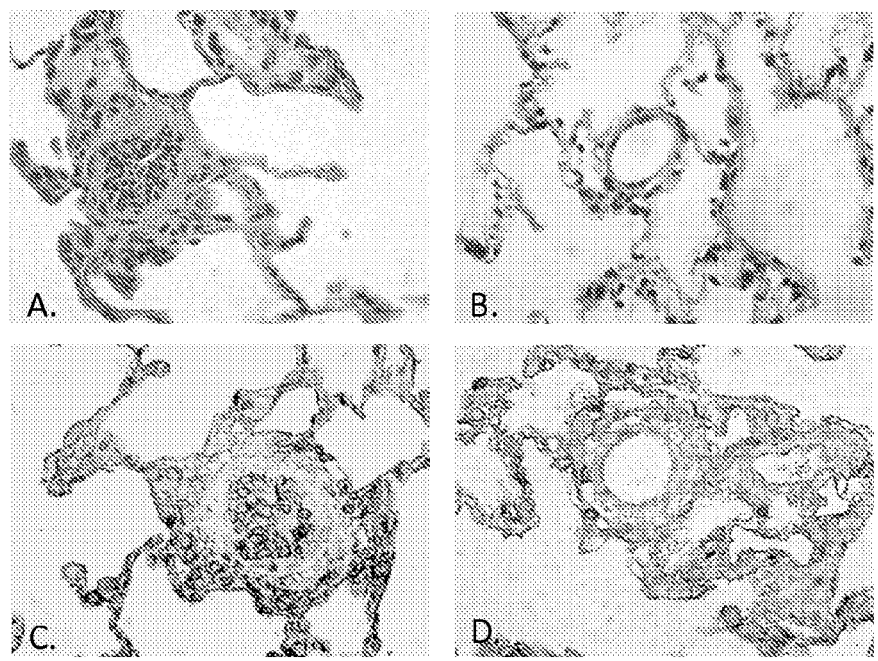

FIG. 8 illustrates the effect of PK10453 (Structure 2) on neointimal lesions in the rat MCT+PN model via 40× microscopic images of pulmonary arteriole hypertrophy and intraluminal cellular proliferation of PK10453 treated specimens. FIG. 8A shows a microscope image of neointimal lesions. FIG. 8B shows an image of PK10453 treated subjects. FIG. 8C shows a phosphoPDGFRβ (pPDGFRβ) stain, vehicle treated animal, while FIG. 8D shows a pPDGFRβ stain for PK10453 (D8) treated animals.

Figure 9:
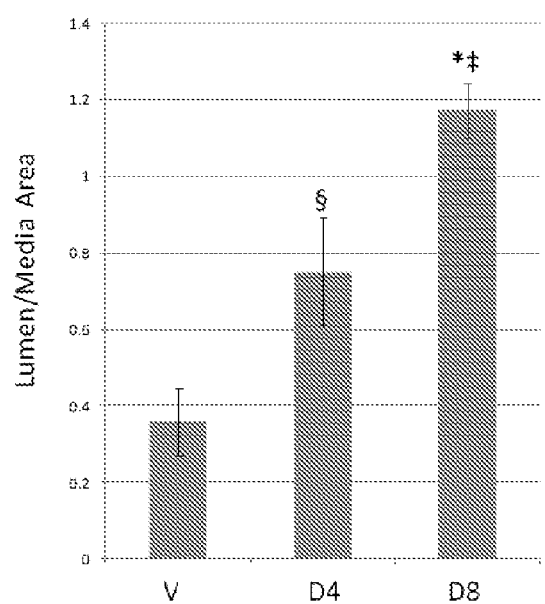

FIG. 9 is a graph showing lumen area:media area, which is increase in D4 (n=6) and D8 (n=5) treated groups compared to vehicle (n=6) via MCT+PN model. Symbol (§) is p=0.032 (D4 vs. V), symbol (‡) is p=0.028 (D8 vs. D4), and asterisk (*) indicates p=0.00014 (D8 vs. V).

Figure 10:
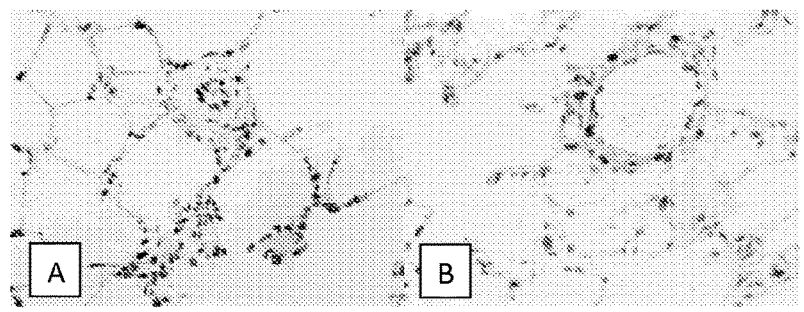

FIG. 10 depicts an immunohistochemical evaluation of MCT+PN samples. FIG. 10A shows that pSTAT3 localized to the nuclei of endothelial cells and perivascular cells with vehicle treatment. FIG. 10B shows lung pSTAT3 nuclear signal from a subject treated with Structure 2.

Figure 11:
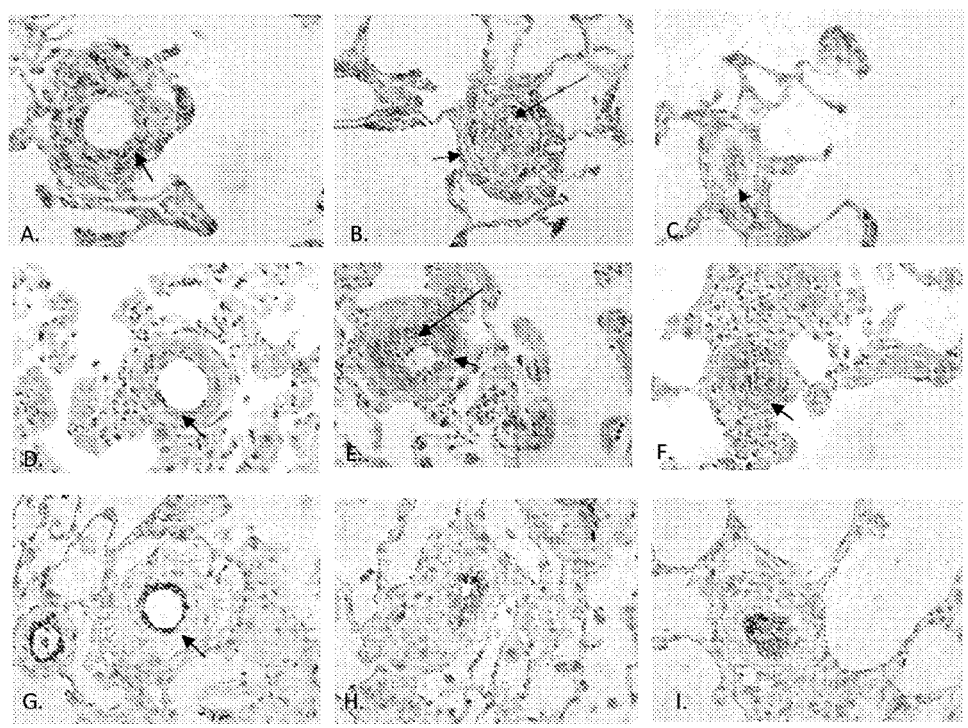

FIG. 11 relates to vehicle treated animals (MCT+PN model) at 40× for immunohistochemically stained αSMC actin, Trichrome and vWF stains, which showed a mixed population of endothelial and myofibroblast cells comprising the neointimal and proliferative lesions in pulmonary arterioles in Grade 0, 1, and 2 lesions: Grade 0 lesions were characterized by early intraluminal endothelial cell proliferation, and presence of vascular smooth muscle cells in the media (FIG. 11A, αSMC stain; FIG. 11D, trichrome; FIG. 11G, vWF). Grade 1-2 lesions had extensive intraluminal myofibroblast-like cells, some endothelial cells, and partial fibrosis of medial layer (FIG. 11B, αSMC; FIG. 11E, trichrome; FIG. 11H. vWF). Advanced Grade 2 lesions were characterized by extensive intraluminal myofibroblast-like and endothelial cell proliferation and complete fibrotic replacement of medial layer (FIG. 11C, αSMC; FIG. 11F, trichrome; FIG. 11I. vWF). The long arrow points to the intraluminal space with proliferative lesions, and the short arrow points to the medial layer of the pulmonary arterioles.

Figure 12:
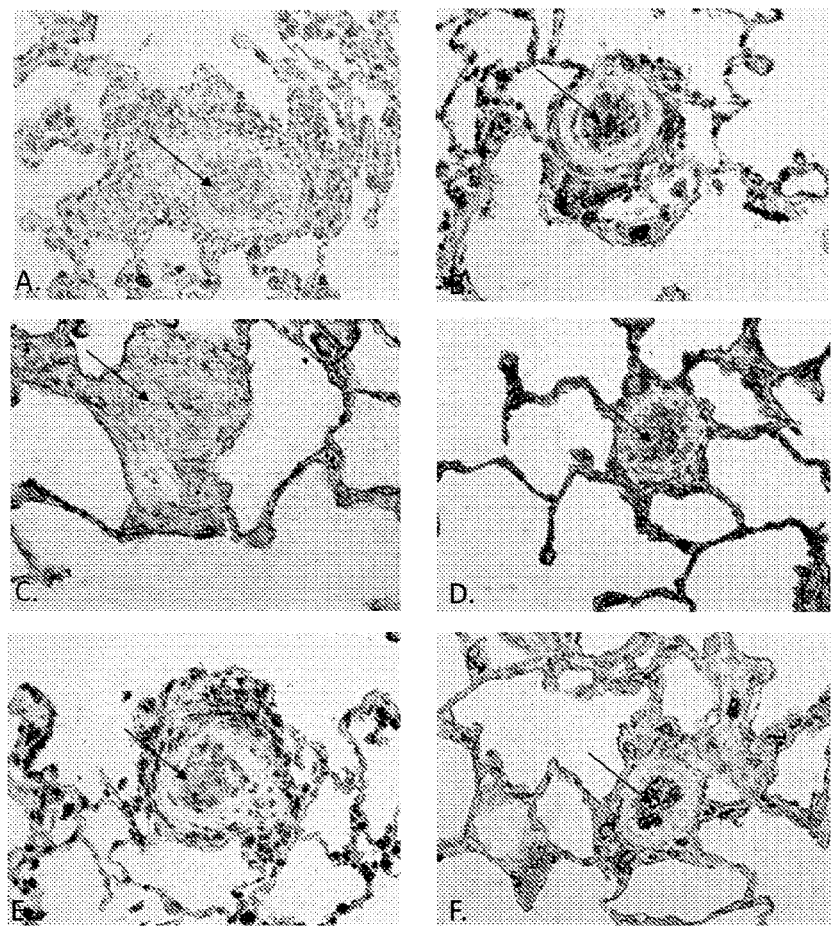

FIG. 12 shows 40× PDGFR signaling in the rat MCT+PN model. FIGS. 12A-F show PDGFAA in a pulmonary arteriole (A); PDGFBB (B); total PDGFRα (C); total PDGFRβ (D); phosphoPDGFRα (pPDGFRα; E); and pPDGFRβ (F). Signal intensity was greater for PDGFBB, PDGFRβ, and especially pPDGFRβ compared to PDGFAA, PDGFRα, and pPDGFRα. The pPDGFRβ signal was intense in a cobblestone pattern in neointimal proliferative and perivascular lesions. Signal intensity was relatively low in vessel media layer. Arrows point to vessel lumens with proliferative lesions (slides are from vehicle treatment).

Figure 13:
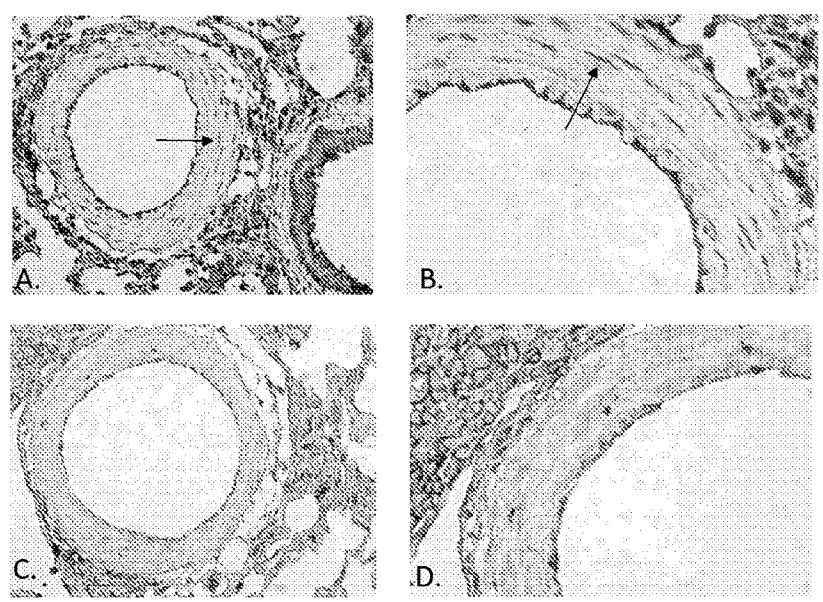

FIG. 13 shows a comparison of pPDGFRα and pPDGFRβ in larger pulmonary arterioles using the rat MCT+PN model system. FIGS. 13A and 13B respectively show 20× and 40× immunohistochemistry for pPDGFRα signal in the media, where the arrow points to a smooth muscle cell positive for pPDGFRα. FIGS. 13C and D respectively show at 20× and 40× imaging that, in contrast to above, there was very little signal in the media for pPDGFRβ. Signal for pPDGFRβ is noted in peri-vascular cells (upper left—FIGS. 13C and D), and endothelial cells.

Figure 14:
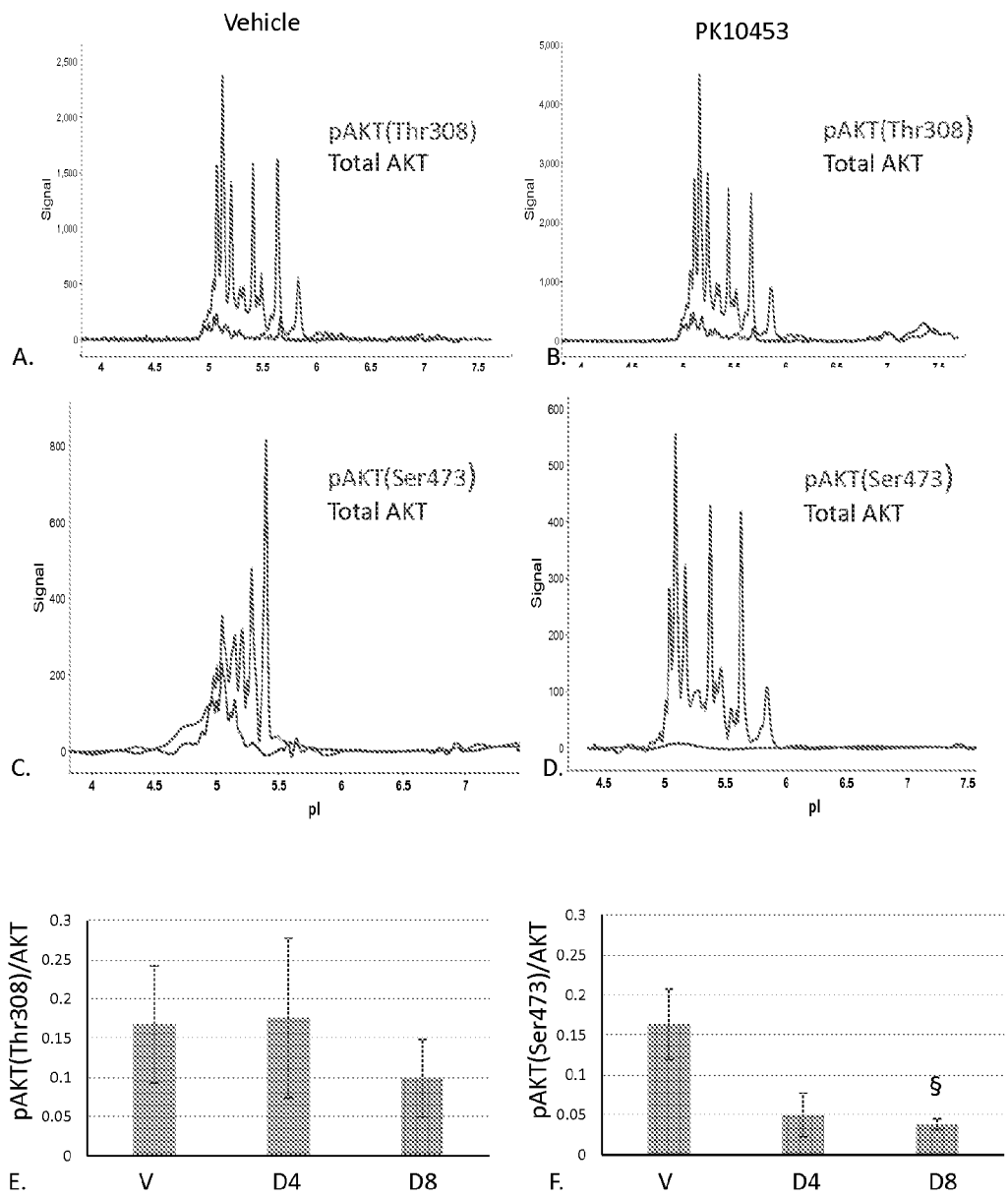

FIG. 14 shows NanoPro Immunoassays shown for the MCT+PN model. FIG. 14A shows pAKT (Thr308) and total AKT, with vehicle treatment. FIG. 14B shows pAKT (Thr308) and total AKT with PK10453 treatment, while FIG. 14C shows pAKT (Ser473) and total AKT, with vehicle treatment. FIG. 14D shows pAKT(Ser473) and total AKT with PK10453 treatment, while FIG. 14E shows that the pAKT(Thr308)/AKT ratio in lung extracts was not significantly different between the groups (V=vehicle; D4=4 minute exposure 3×/day for 2 weeks, D8=8 minute exposure 3×/day for two weeks, p=NS). FIG. 14F represents the pAKT(Ser473)/AKT ratio in lung extracts for D8 group vs. vehicle (V, n=5; D4, n=4; D8, n=5) §p<0.05 D8 vs. V.

Figure 15:
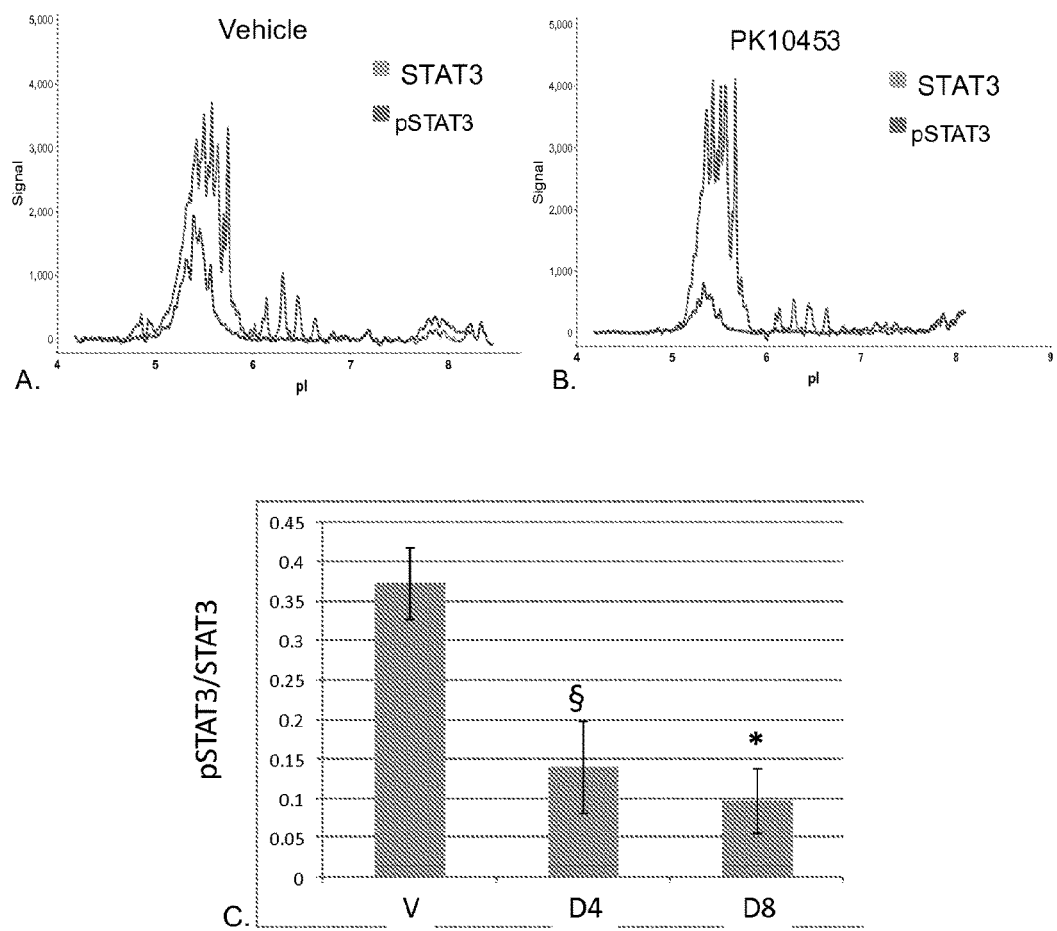

FIG. 15 reveals results from experiments employing the NanoPro Immunoassay lumogram for pSTAT3 and STAT3 in the MCT+PN model. FIG. 15A is a graph of the vehicle treated subjects. FIG. 15B is a graph of the PK10453 (Structure 2) treated subjects. FIG. 15C shows a graph of PK10453 treatment, which decreased pSTAT3/STAT3 in the lungs of subjects using the MCT+PN model (n=4), where V represents vehicle, D4 represents 4 min exposure times three times daily, and D8 represent 8 min exposure times for two weeks three times daily; 3×/day for two weeks PK10453. Asterisks (*) p=0.009 and section symbols (§) indicate p=0.024.

Figure 16:
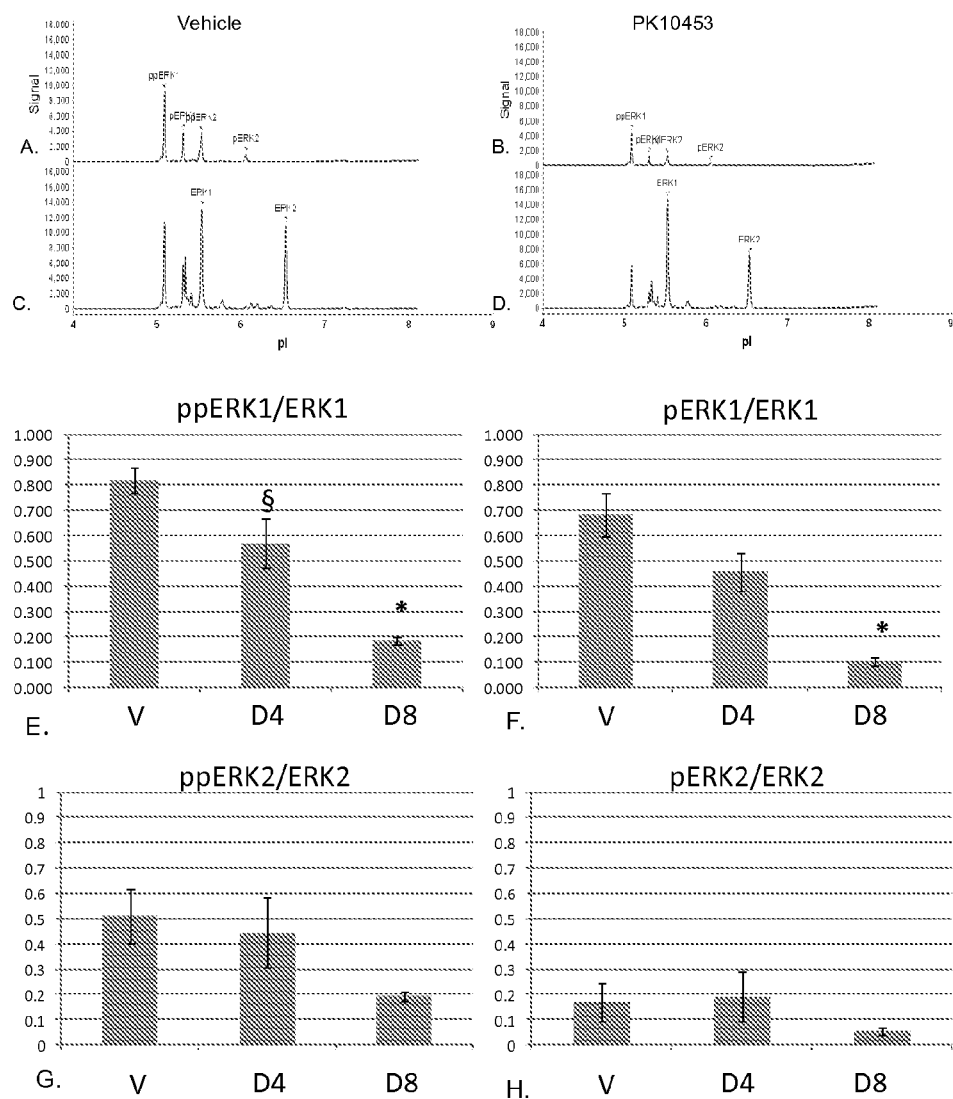

FIG. 16 shows the results from experiments using the Nanopro Immunoassay lumograms for phosphoERK1/2 (pERK1/2) and total ERK1/2 in the MCT+PN model. FIG. 16A shows pERK1/2 in vehicle treated subjects. FIG. 16B shows pERK1/2 in PK10453 treated subjects. FIG. 16C shows total ERK1/2 and vehicle treated subjects. FIG. 16D shows total ERK1/2 in PK10453 treated subjects, where PK10453 decreased ppERK1/ERK1. FIG. 16E shows ppERK1/ERK1 in subjects as indicated. FIG. 16F shows pERK2/ERK2 as indicated. FIG. 16G shows ppERK2/ERK2 as indicated in the lungs. FIG. 16H shows pERK2/ERK2 as indicated in the lungs. The n=4 for each group, while V represents vehicle, D4 represents 4 min exposure times, three times daily, and D8 represents 8 min exposure times of PK10453 (Structure 2) for two weeks three times daily. Asterisks (*) p≤0.0005; §p=045.

Figure 17:
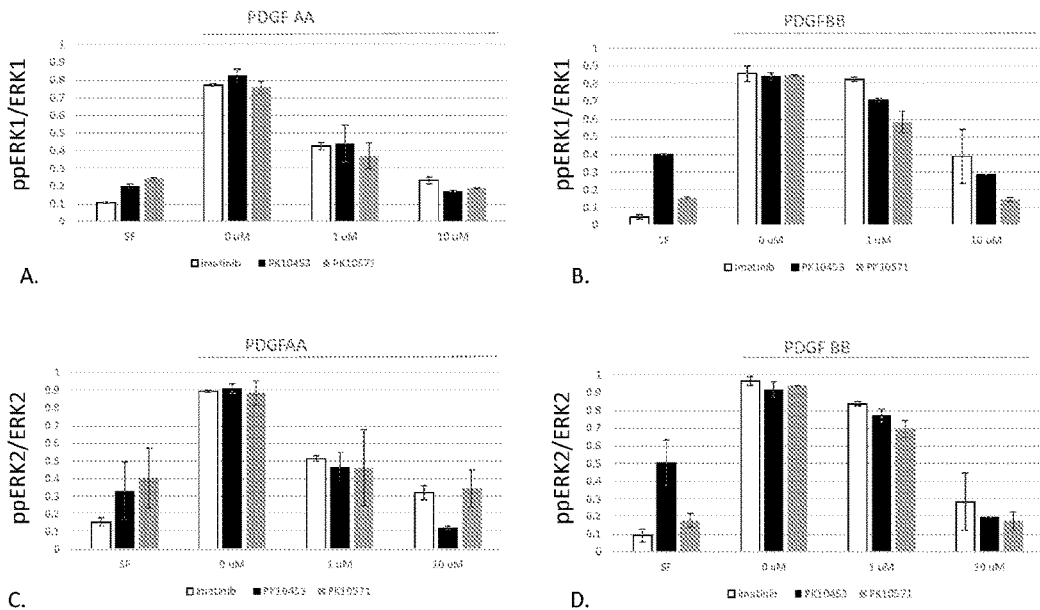
Figure 18:
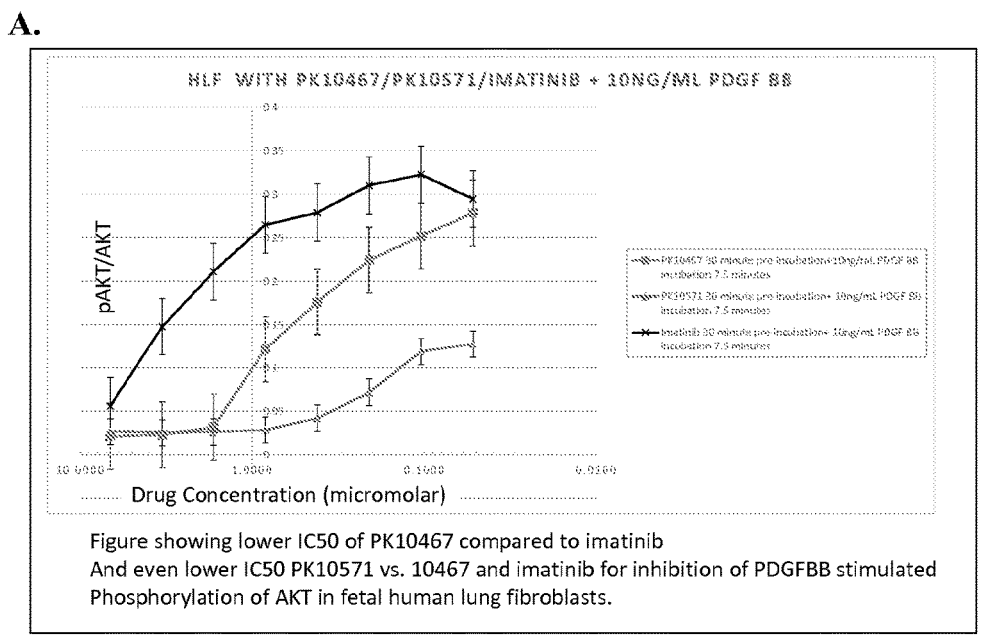
Figure 18:
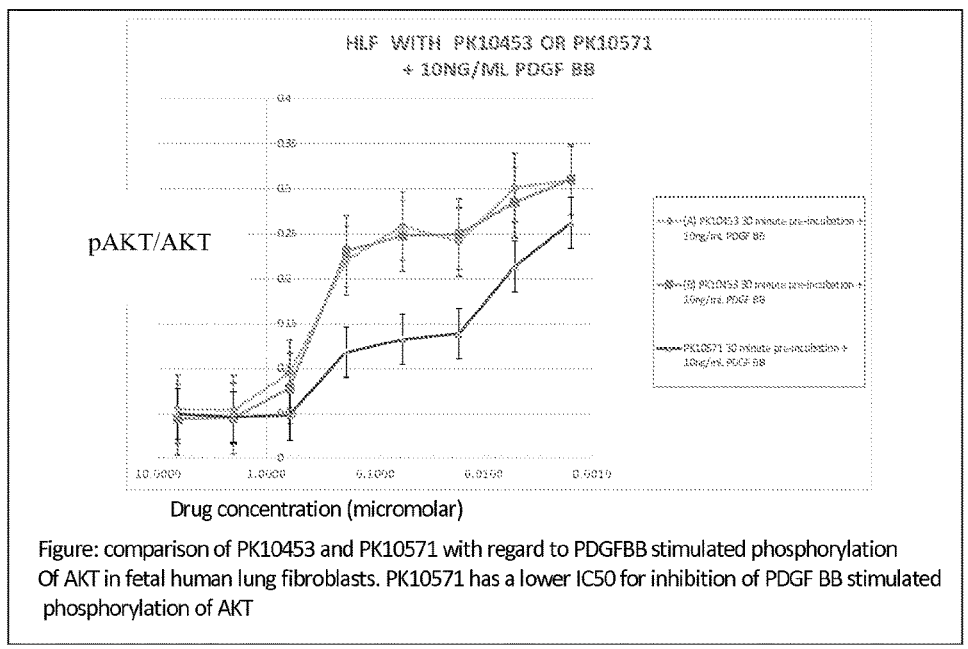
Figure 18:
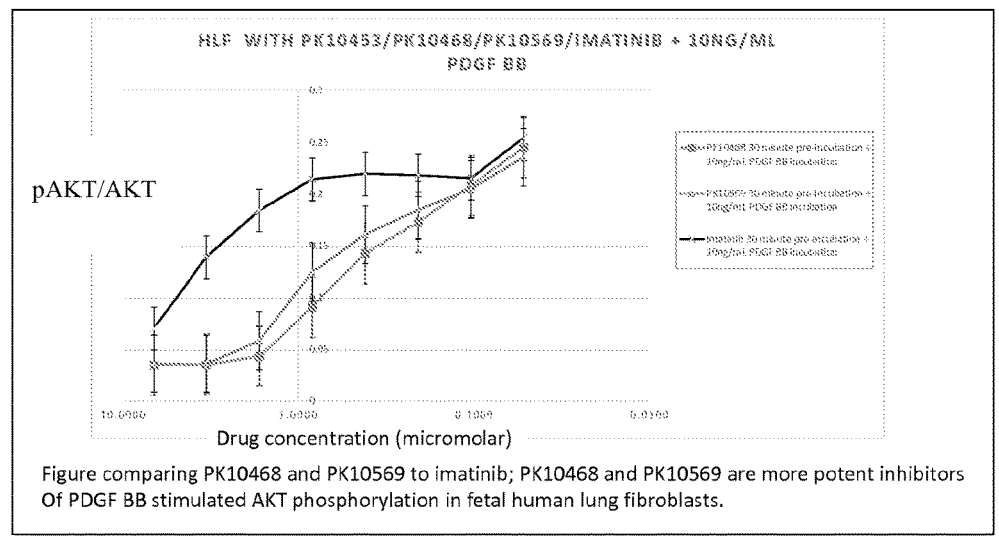
Figure 18:
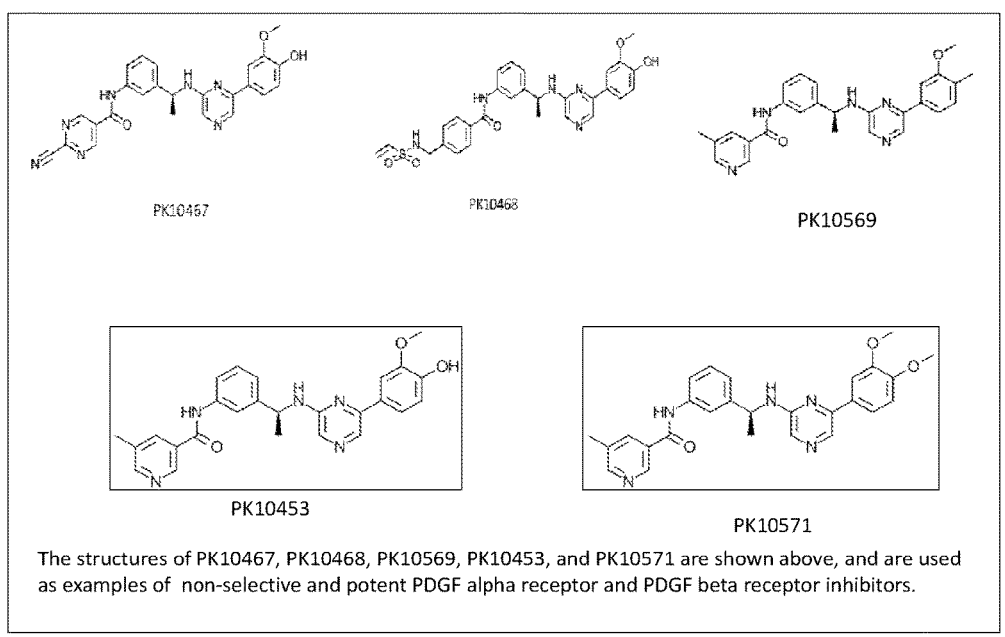

FIG. 17 is a graphic representation showing the effect of imatinib, PK10453 (Structure 2), and PK10571 (Structure 2a) on PDGFAA vs. PDGFBB stimulated phosphorylation of ERK1 and ERK2 in human fetal lung fibroblasts. See FIG. 17A-D.

FIG. 18A-D is a graphic representation of PK compounds: PK10453 (Structure 2), PK10467 (Structure 3), PK10468 (Structure 4), PK10569 (Structure 5) and PK10571 (Structure 2a), showing that all PK compounds possess a lower $IC_{50}$ concentration compared to imatinib for inhibiting PDGFBB stimulated AKT phosphorylation in fetal human lung fibroblasts.

Figure 19:
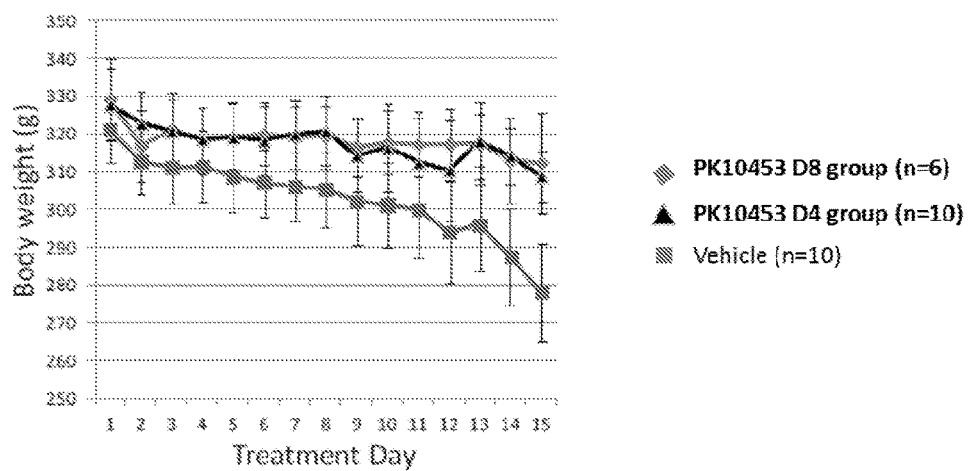

FIG. 19 is a graphic representation of subject body weight in vehicle administered and PK10453 (Structure 2) treated subjects, where squares indicate vehicle treated (n=10), triangles indicate PK10453 D4 group (n=10), and diamonds indicate PK10453 D8 group (n=6).

Figure 20:
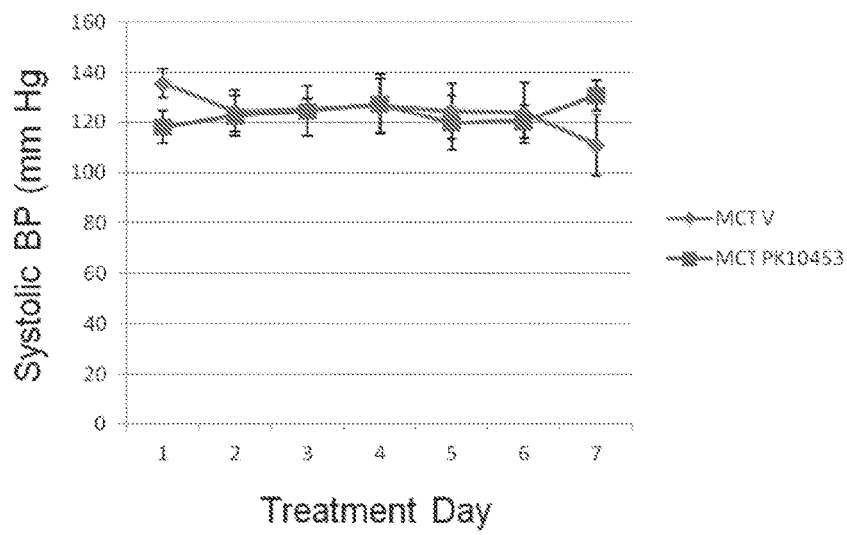

FIG. 20 is a graph representing PAC40 telemetry transmitter data from transmitters implanted in the abdominal aorta for monitoring systemic blood pressure for seven days in ambulatory MCT exposed subjects treated with vehicle (n=3) or PK10453 (n=3).

Figure 21:
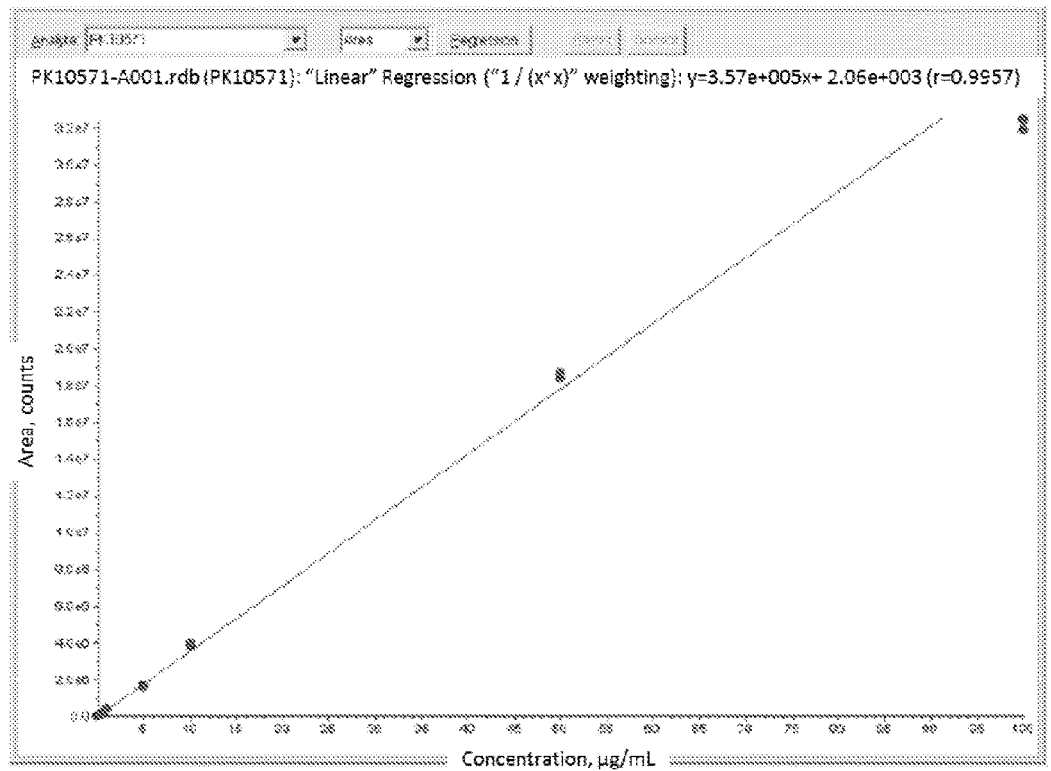

FIG. 21 is a graph showing the calibration curve used to determine PK10571 concentrations in the SDDs. Concentrations are expressed as μg/mL.

Figure 22:
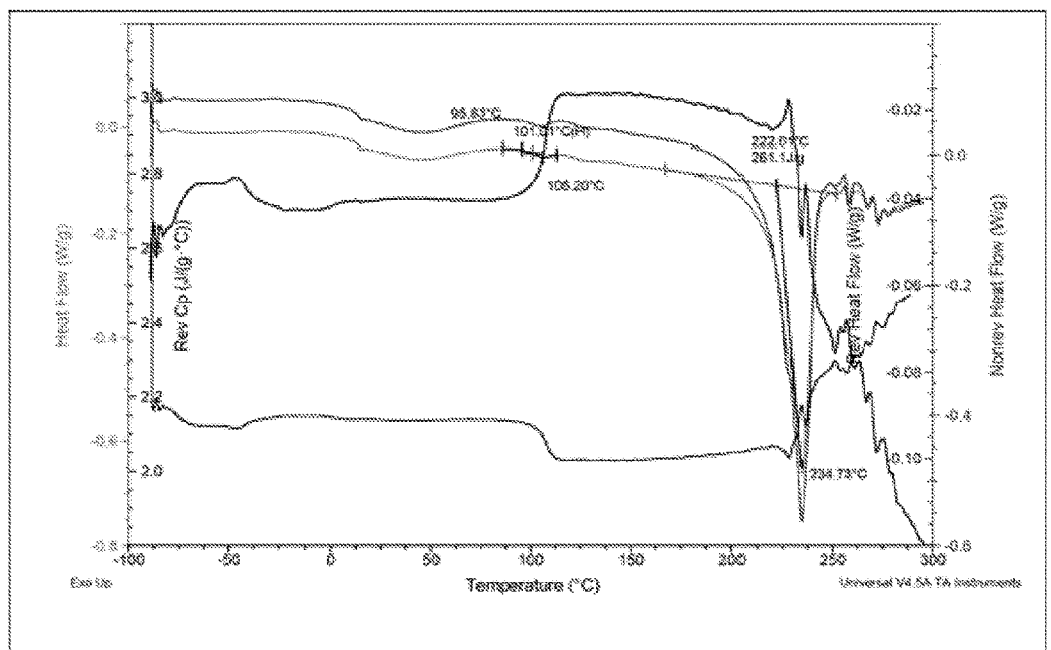

FIG. 22 shows an example of MDSC for PK04 showing glass transition temperature (Tg) at 101° C.

Figure 23:
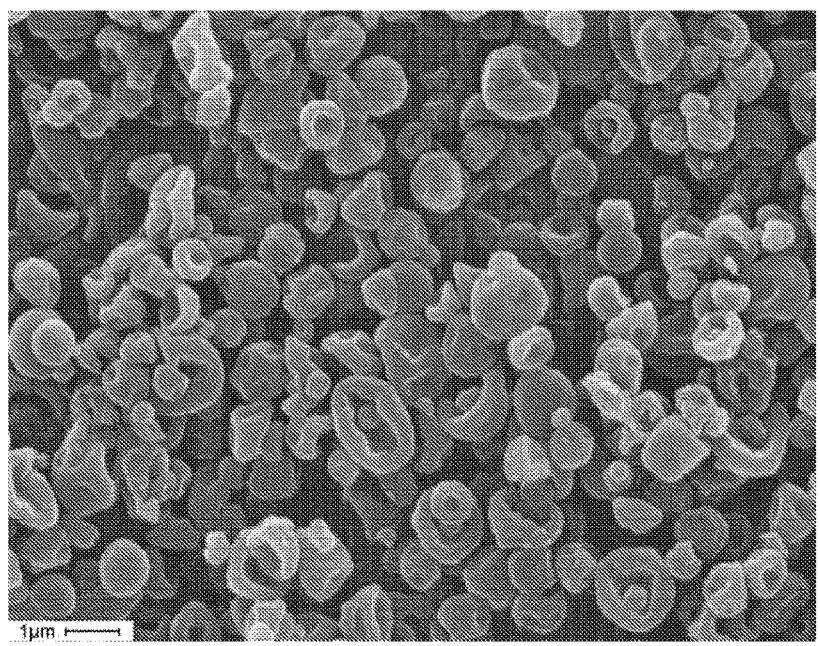

FIG. 23 is a scanning electron micrograph of PK004 SDD containing PK10571 and L-leucine. Morphology is that of dimpled spheres.

Figure 24:
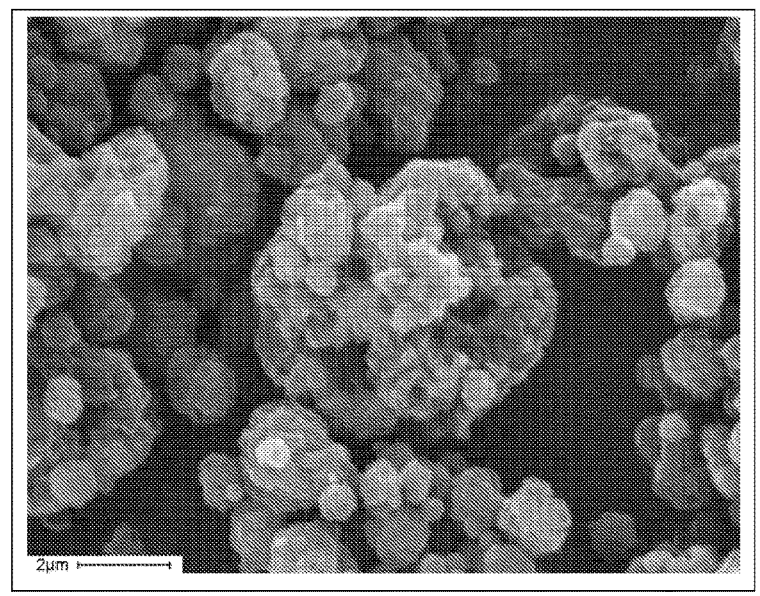

FIG. 24 is a scanning electron micrograph of PK61914 SDD containing PK10571 with Trehalose and Leucine excipients. Morphology is that of rippled/ridged spheres.

Figure 25:
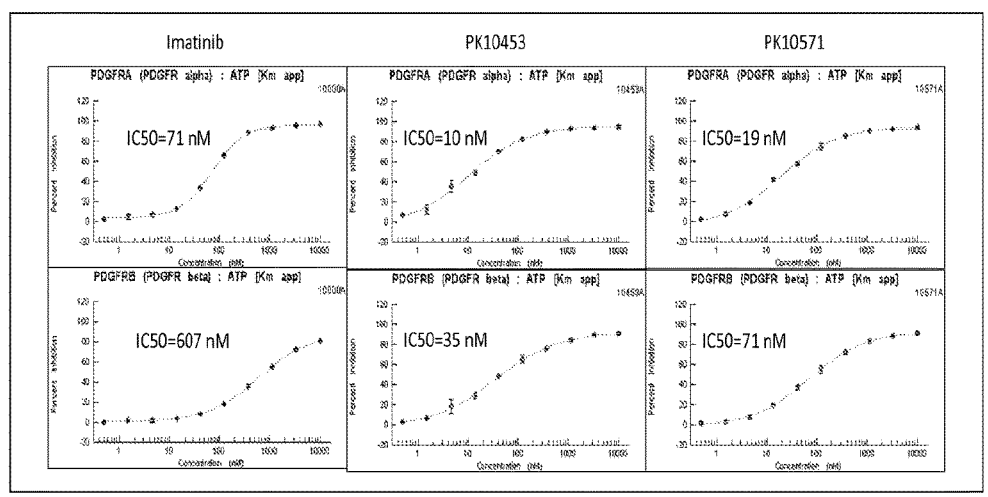

FIG. 25 shows IC50 against PDGFR alpha vs. beta kinase domains. PK10453 and 10571 are more potent than imatinib against the beta isoform.

Figure 26:
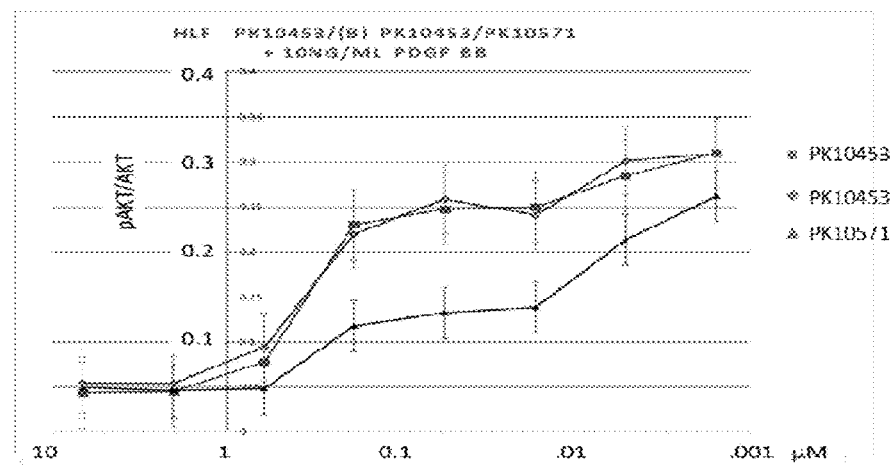

FIG. 26 shows PDGF BB stimulated pAKT in human lung fibroblasts. Each assay each concentration is done in duplicate. PK10453 IC50 0.15 μM. PK10571 IC50 0.05 μM. As we showed in our recent publication in Pulmonary Circulation, the IC50 for inhibition of PDGFBB stimulated AKT phosphorylation by imatinib was 1.8 μM.

Figure 27:
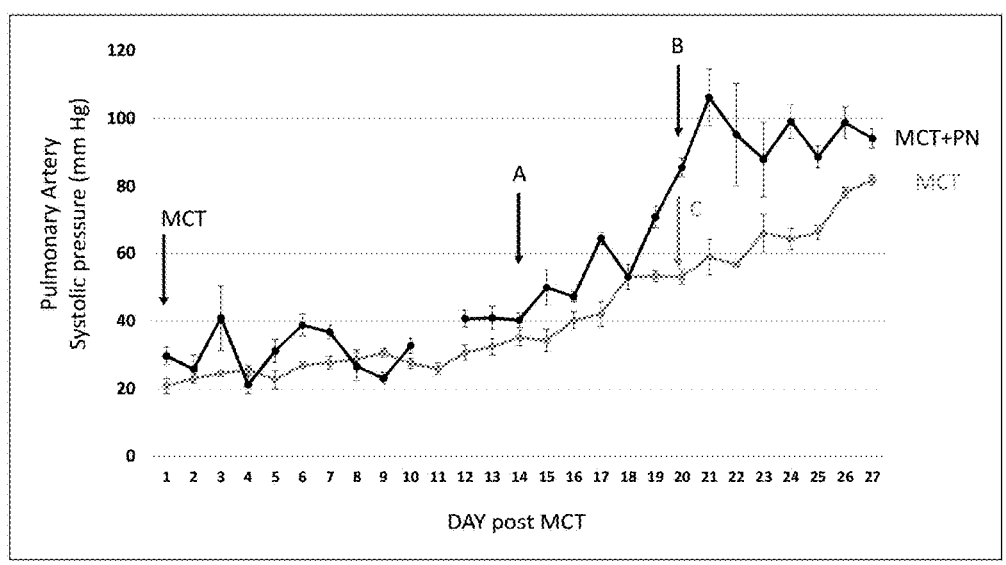

FIG. 27 is a time course over which pulmonary hypertension develops in the MCT+PN model compared to MCT only model. A. PK10453 study time drug treatment started (See Pulm Circ 2014 8(1):82-102). B. PK10571 SDD study time treatment started in MCT+PN model. C. Start time typical for MCT only model. Data acquired via telemetry monitoring of PA pressures in ambulatory rats. (Note: Day 11 in MCT+PN model data not shown).

Figure 28:
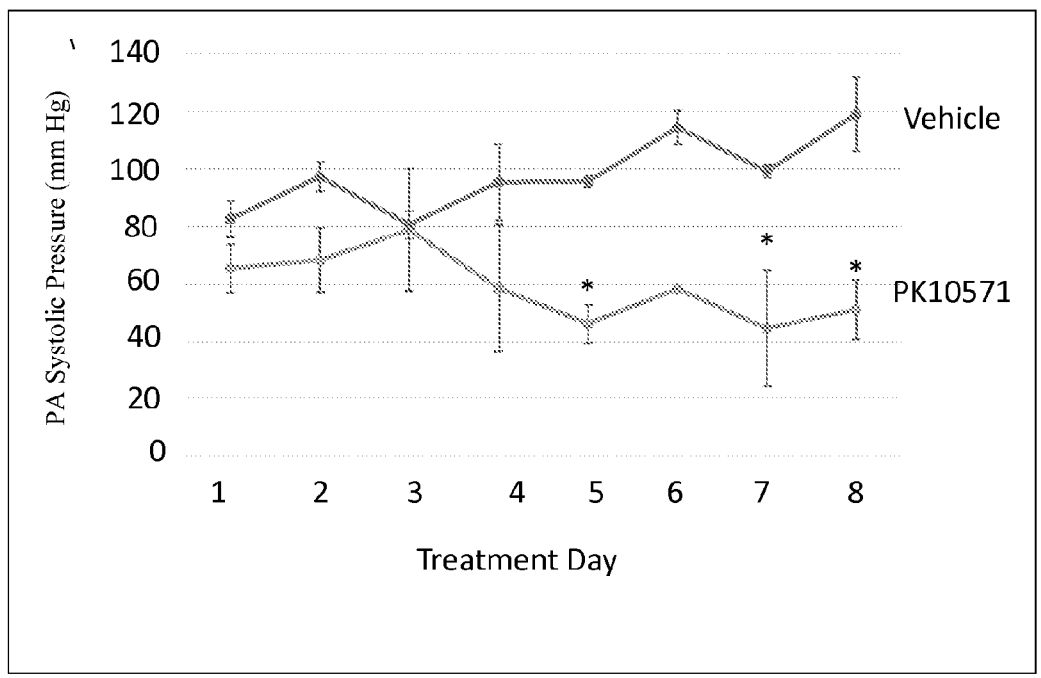

FIG. 28 is a graph showing reduction of PA pressure over time in MCT+PN rats treated with Inhaled PK10571 (n=5) treated group. Pressure data from PAC40 telemetry implants in PA. Vehicle group was n=7 but 4 vehicle animals died between days 2 and 4 of treatment. See text for details. Data shown are mean±SE.*p<0.05 Repeated measures ANOVA (note: day 1 PK10571 vs. Vehicle p=NS); Some Day 6 data files were lost for Drug group except for 1 animal, so this data point could not be used for analysis. (Day 1 of treatment=Day 21 post MCT; Day 31 post pneumonectomy).

Figure 29:
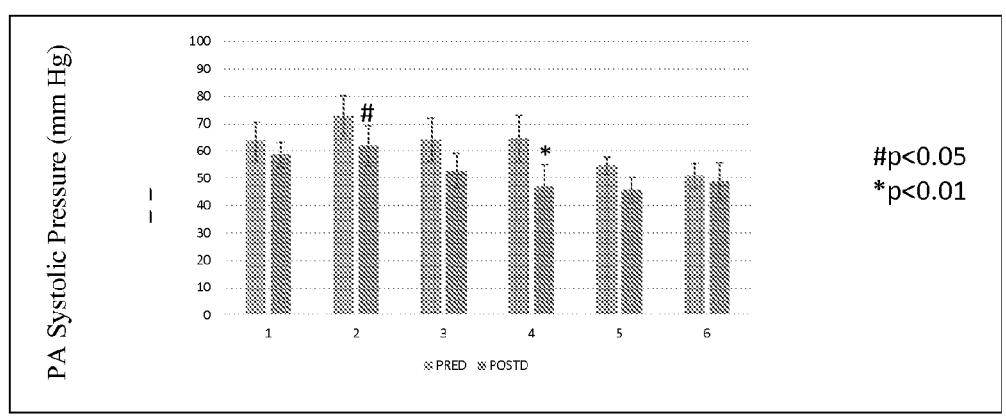

FIG. 29 is a graph showing PK10571 in MCT+PN model: pre and post dose (approximately 1 hour). Data shown for day 1-6 treatment. There was a transient decrease in pulmonary artery systolic pressure seen post dosing in the early stage of treatment (i.e., up to day 4), though this transient dose effect appeared to decrease later in treatment while the overall PA systolic pressure fell. These data suggest both vasodilatory and anti-proliferative effects of PK10571, with the later probably being more important.

Figure 30:
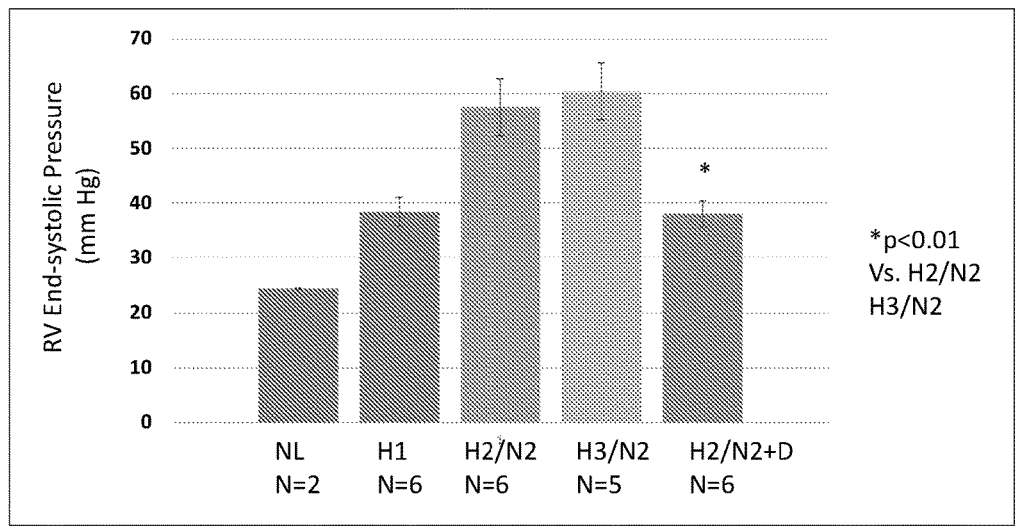

FIG. 30 is graph showing Efficacy of inhaled PK10571 in the SU5416/hypoxia/normoxia model of PAH. NL=normal control; H1=SU5416+1 week hypoxia; H2/N2=SU5416+2 weeks of hypoxia and 12 days of normoxia with inhaled vehicle twice daily during 11 days of normoxia (Vehicle was started on day 2 of normoxia); H3/N2=SU5416+3 weeks hypoxia and 2 weeks normoxia; H2/N2+D=SU5416+2 weeks hypoxia and 12 days of normoxia and treatment with inhaled PK10571 twice daily during 11 days of normoxia. (Drug treatment was started on Day 2 of normoxia). Inhaled PK10571 resulted in a significant decrease in RV end systolic pressure compared to vehicle treated animals (H2/N2). There was no significant difference between H2/N2 and H3/N2 groups. Statistical analysis: ANOVA with Bonferroni correction for multiple comparisons.

Figure 31:
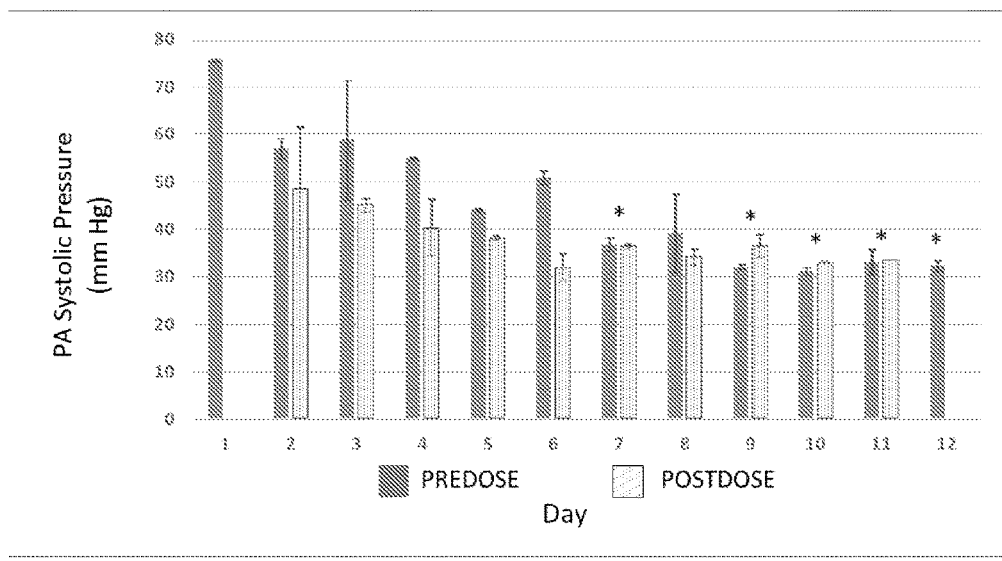

FIG. 31 is graph showing SU5416/hypoxia(2 weeks)/normoxia(12 days); PA pressures monitored continuously in n=3 animals treated with PK10571 twice daily. Treatment was started the day after removal from the hypoxia chamber (day 2). In our experience there is an initial drop in PA pressure in the first 24 hours after removal from the hypoxia chamber and introduction to normal atmosphere. Therefore we started the drug treatment on day 2 after removal from the hypoxia chamber and continued treatment for 10 days. On day 12, the animals underwent euthanasia and tissue harvest. PA systolic pressure prior to daily dosing (blue) and PA systolic pressure approximately 1 hour after dosing (orange) are shown. Statistical analysis was performed with repeated measures ANOVA and the Bonferroni correction for multiple comparisons. *p<0.0001 day 6, 7, 9-12 vs day 2 and 4. Other significant comparisons Day 1 vs 2,4,5-12 p<0.0001; Day 5 vs. Day 11 p=0.002.

Figure 32:
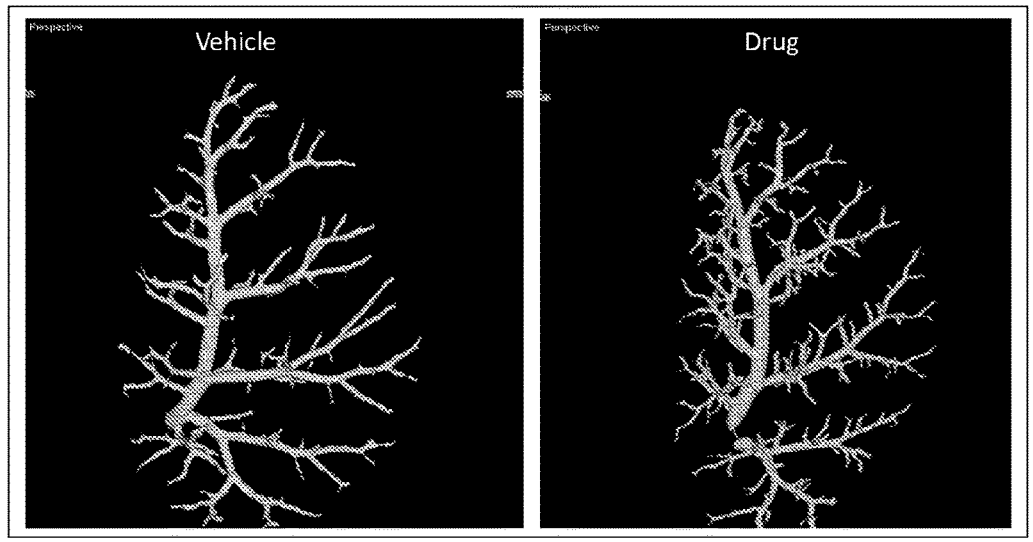

FIG. 32 is a 3D microCT of Pulmonary Arterial Vasculature after treatment with sodium nitroprusside in SU5416/hypoxia/normoxia model of PAH. Vehicle treated animal on left. PK10571 treated animal on right. Resolution: 20 microns.

Figure 33:
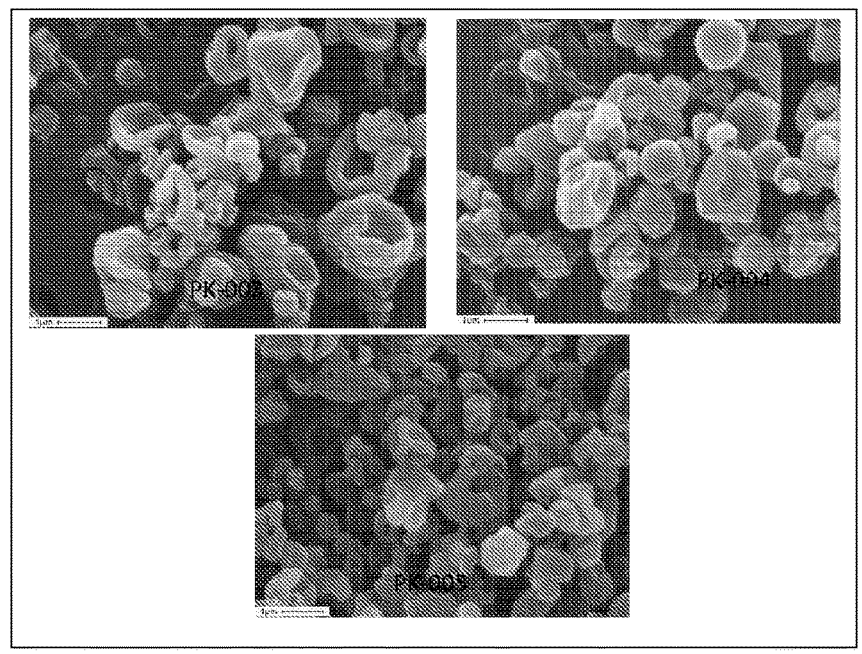

FIG. 33 is a scanning electron micrograph of PK10571 spray dried with leucine excipient.

Figure 34:
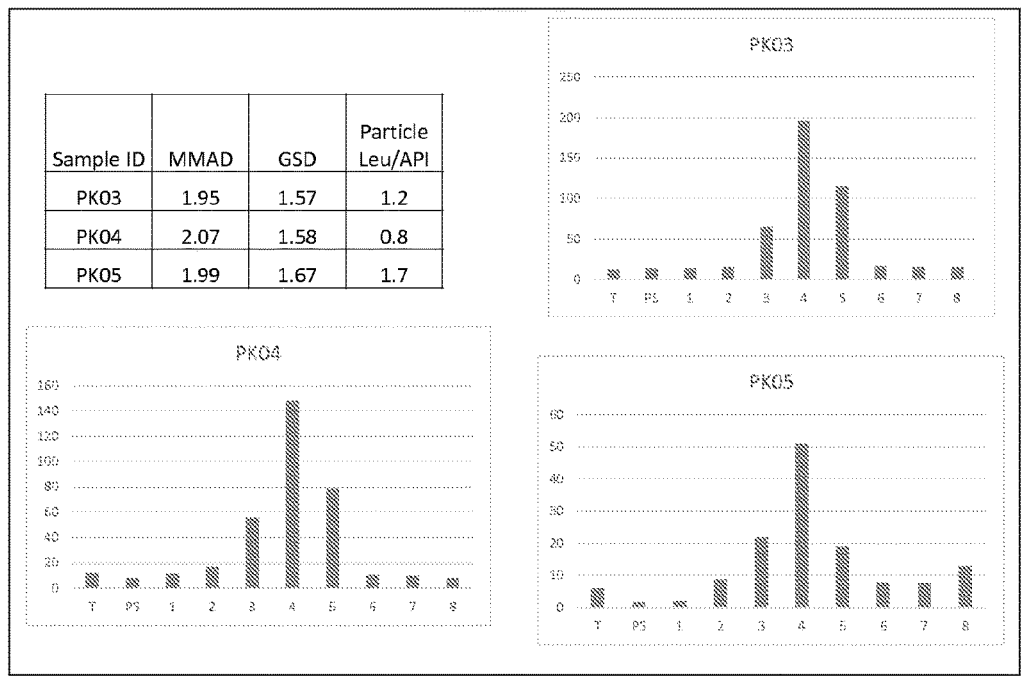

FIG. 34 shows the Mass Median Aerodynamic Diameter was determined with an NGI cascade Impactor: T="throat"; PS=pre-separator. 1-8=Stages of the NGI cascade impactor. MMAD=Mass median aerodynamic diameter; GSD=geometric standard deviation. Here, PK10571 spray dried with 1,2-Distearoyl-sn-glycero-3-phosphocholine (DSPC), where the observed glass transition temperature for PK013 PK10571-DPSC (S142533) was 67° C.

Figure 35:
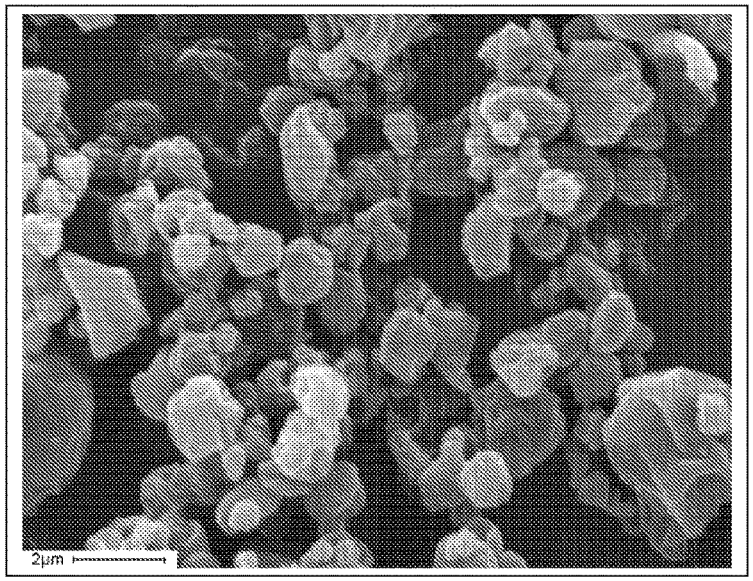

FIG. 35 shows a scanning electron micrograph of PK10571 with DSPC excipient.

Figure 36:
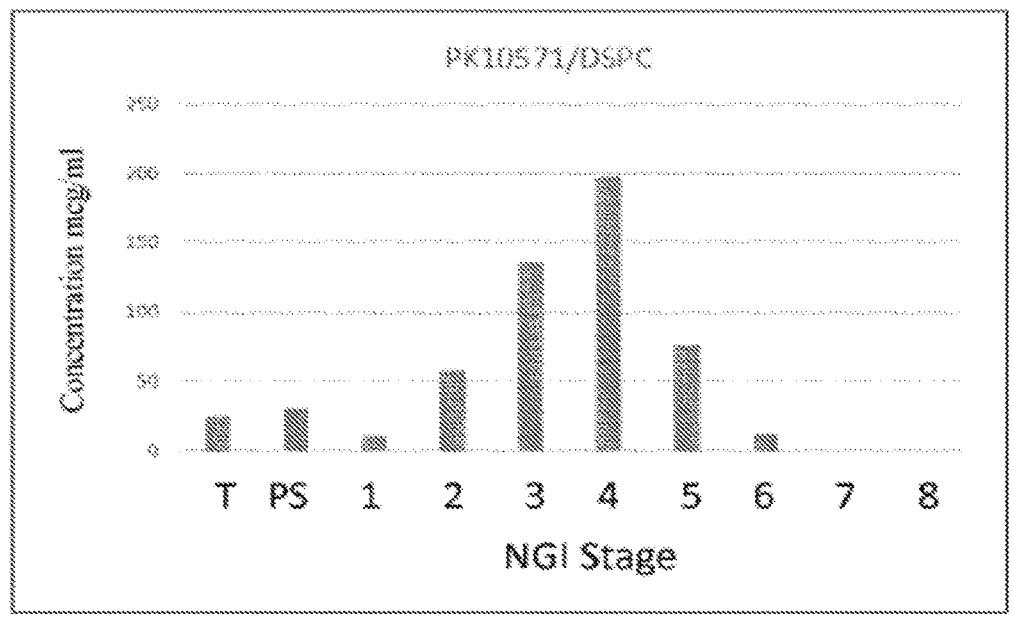

FIG. 36 is a graph showing particle size distribution of PK10571/DSPC spray dry powder. NGI Cascade impactor used at 60 L; min for 4 sec. HPMC capsule loaded in Monodose inhaler. MMAD=2.5 micron GSD 1.6.

Figure 37:
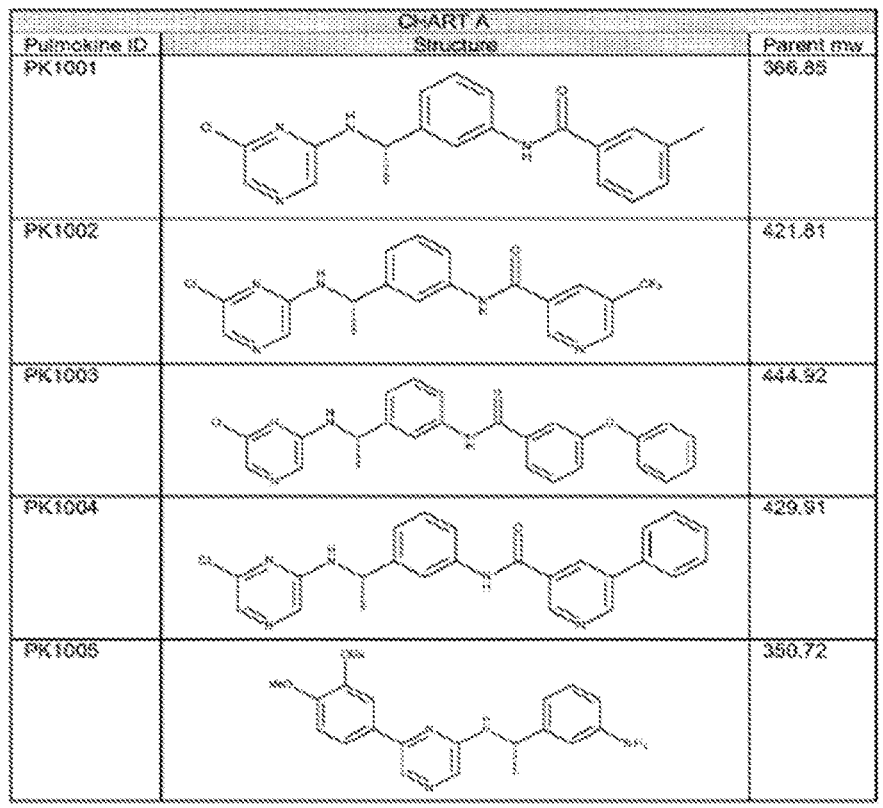
Figure 37:
Figure 37:
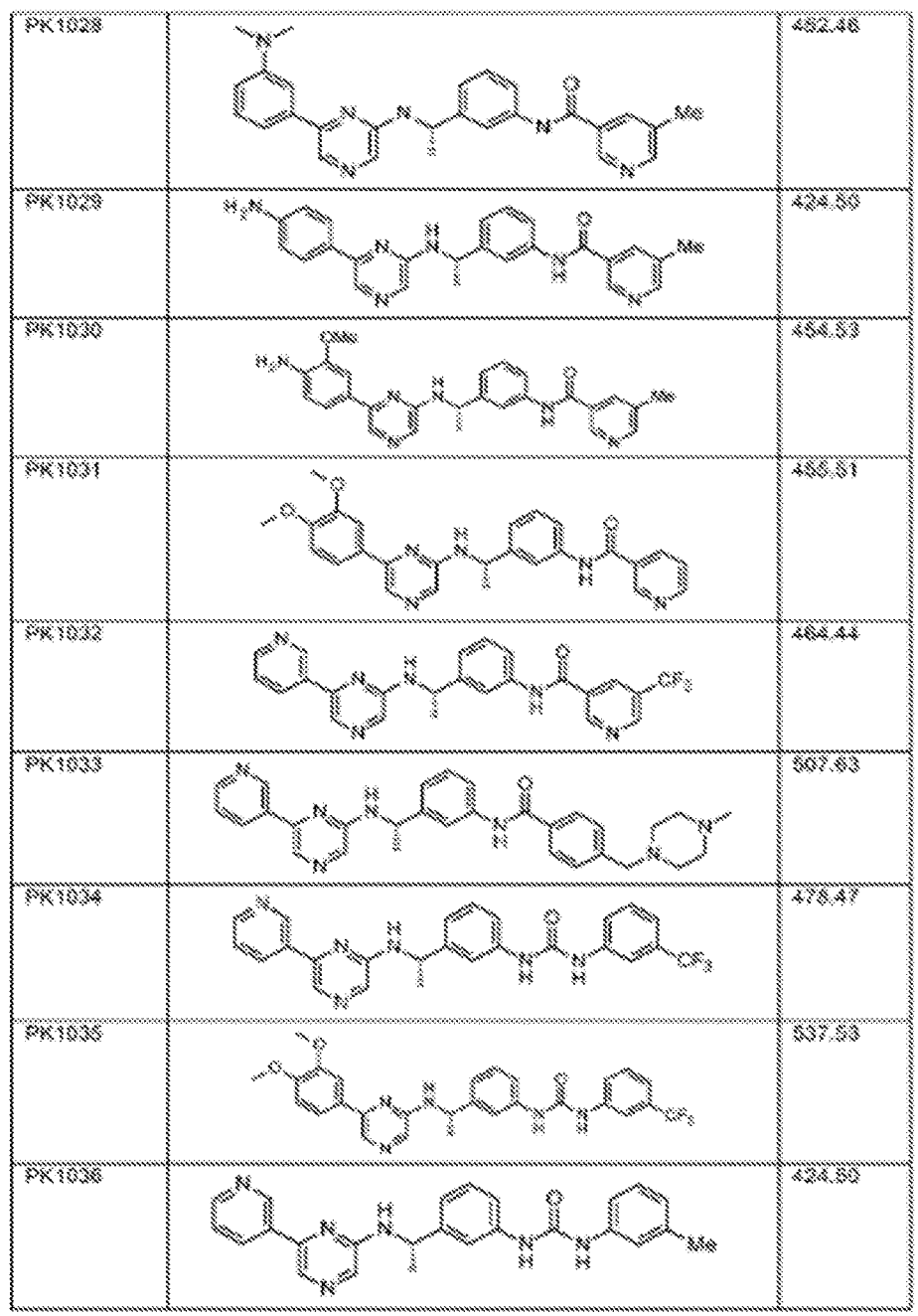

FIG. 37 is a chart identifying compound nomenclature, structure and molecular weight (MW).

Figure 38:
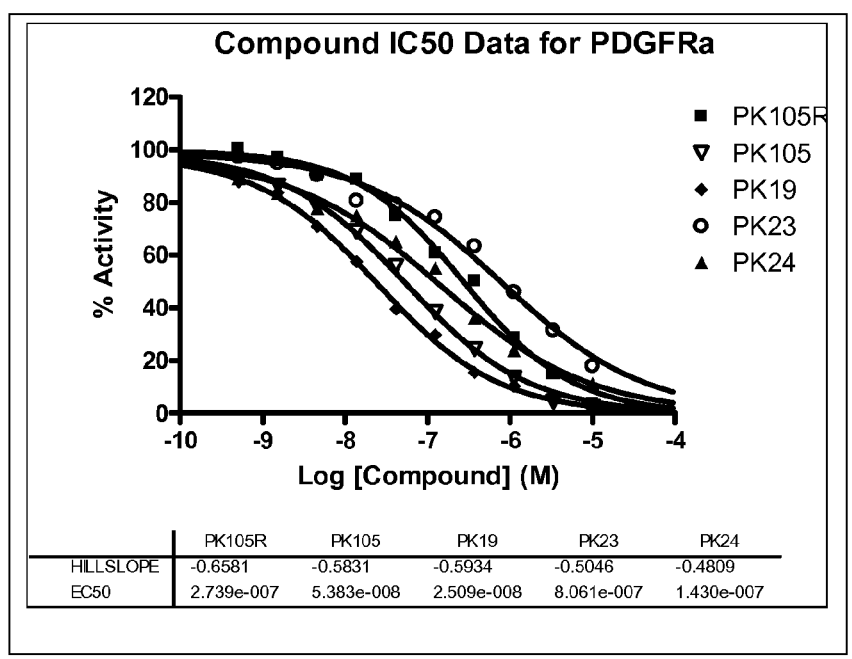

FIG. 38 is a graph showing compound IC50 data for PDGFRα.

Figure 39:
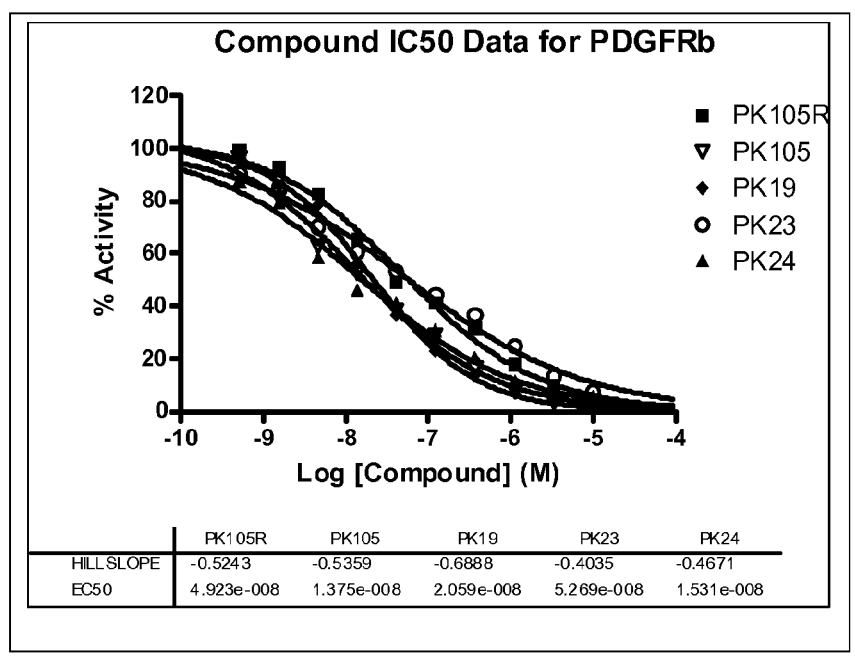

FIG. 39 is a graph showing compound IC50 data for PDGFRβ, where: PK105R=PK10571 racemic mixture; PK105=PK10571; PK19=PK1019; PK23=PK1023; and PK24=PK1024.

Figure 40:
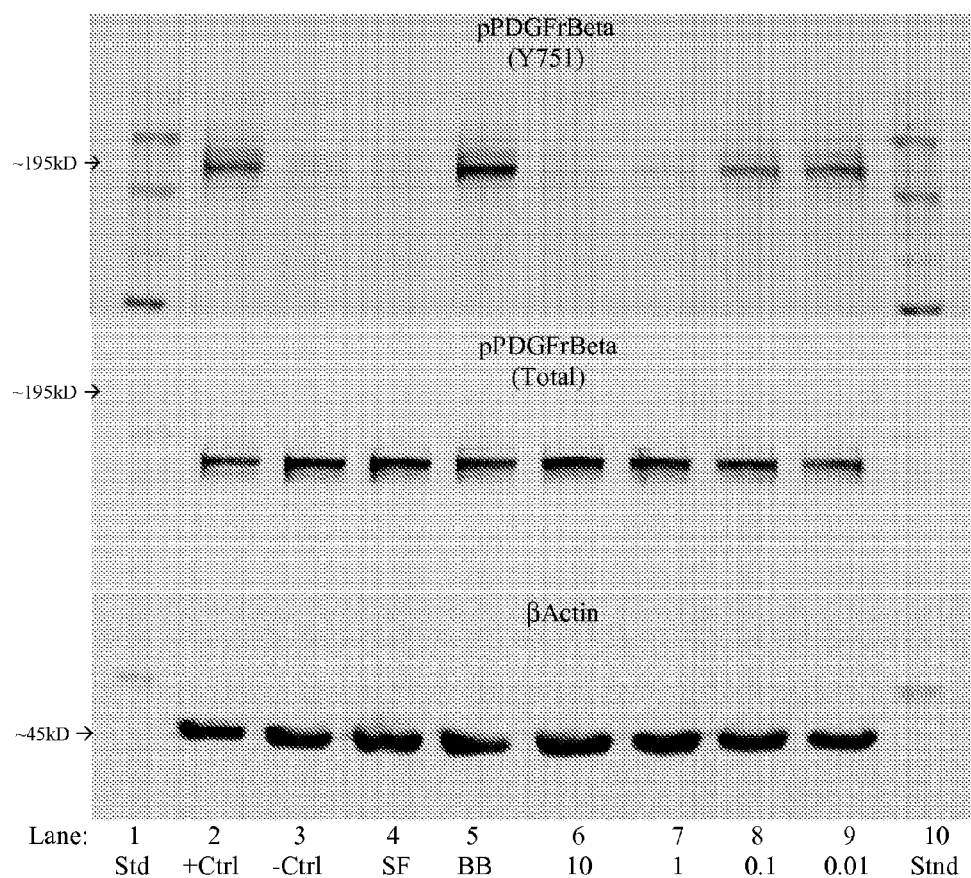
Figure 40:
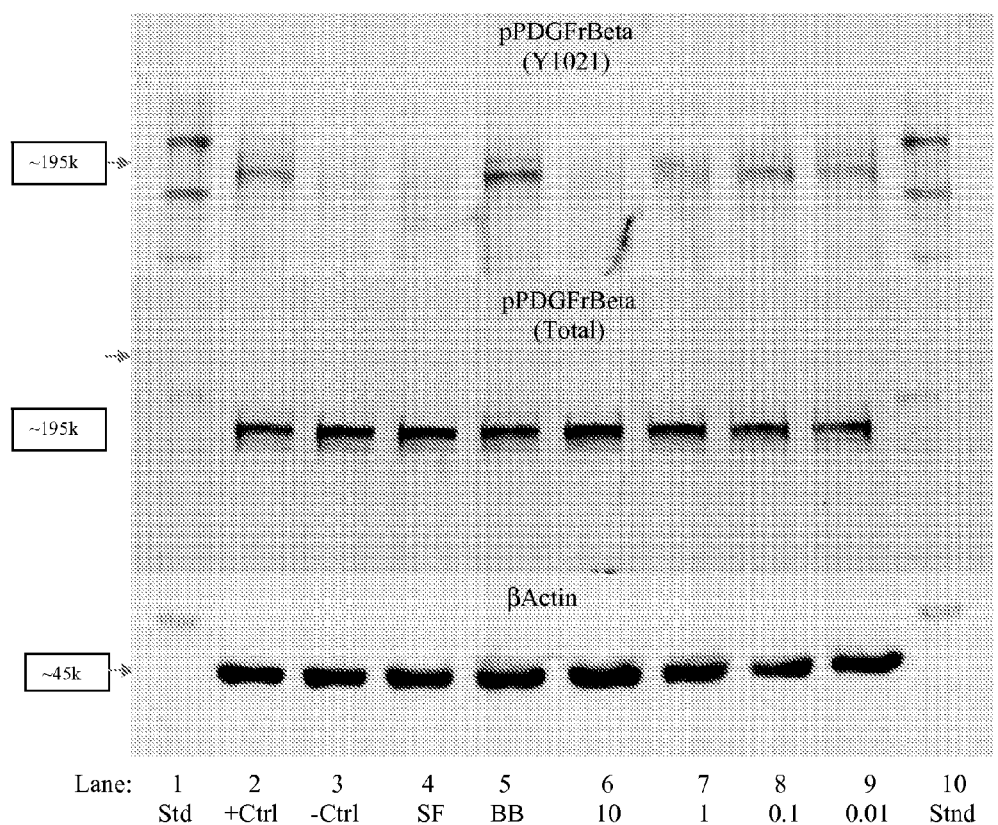

FIG. 40 illustrates pPDGFrBeta (Y751; FIG. 40A; Y1021 FIG. 40B) and β-Actin, stripped and reprobed with total PDGFrBeta.

Figure 41:
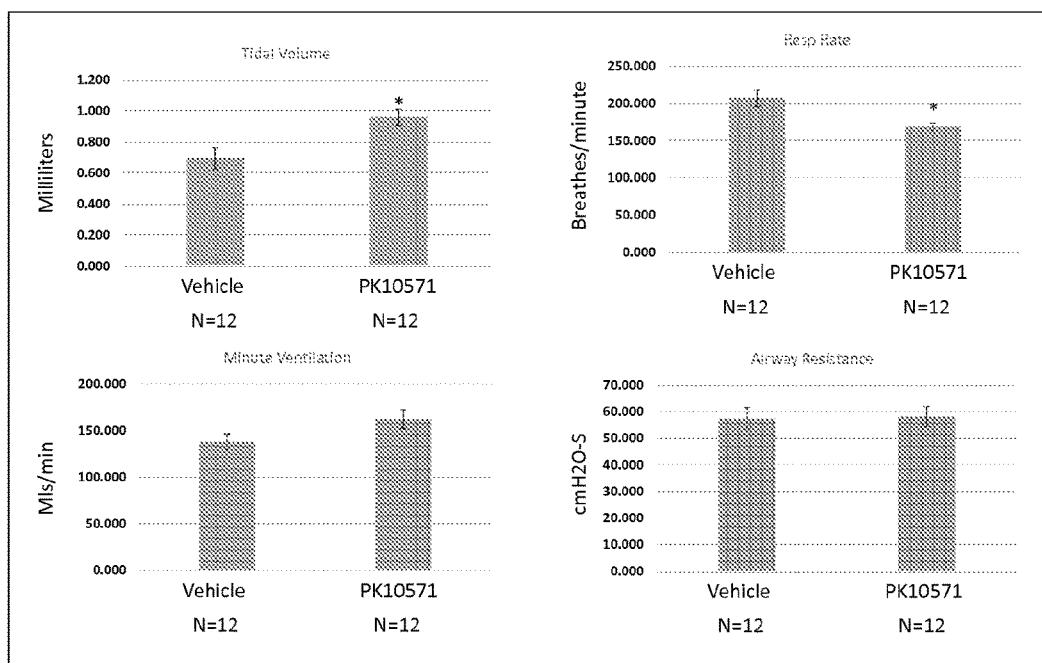
Figure 42:
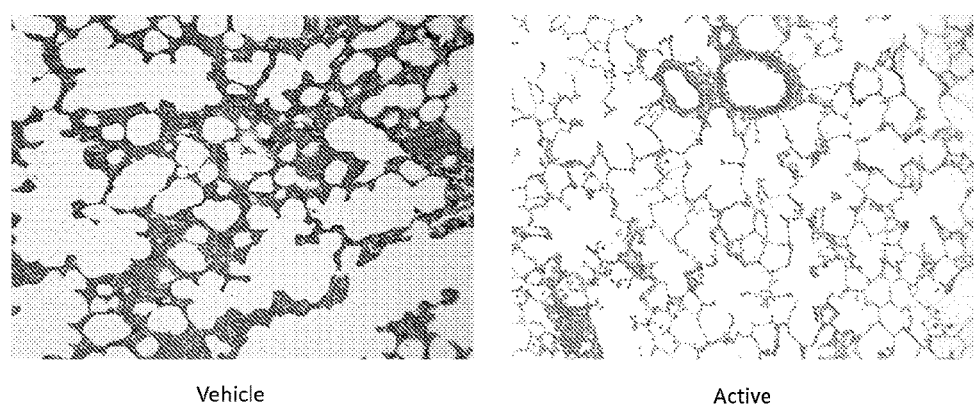

FIG. 41 is a graph showing PK10571 dry powder was delivered by inhalation to Sprague Dawley rats with monocrotaline pneumonectomy induced pulmonary hypertension associated with pulmonary fibrosis FIG. 42 is a trichrome stain of lung sections from Vehicle treated animal compared to PK10453 treated animal in rat monocrotaline plus pneumonectomy model. Blue color indicates collagen.

DETAILED DESCRIPTION

Pulmonary arterial hypertension (PAH) is an orphan disease associated with high morbidity and mortality. With currently available standard therapy, three-year survival in patients with idiopathic PAH (iPAH) was reported to be 84%, but only 49% in patients with PAH secondary to scleroderma.[1-3] Despite recent advances in vasodilator therapy for PAH, more effective treatments are needed.[4-15] Compounds of the present disclosure, including PK10571, are highly potent platelet derived growth factor receptor (PDGFR) inhibitor. PDGFR is a tyrosine kinase receptor which, when activated by its agonist, induces cell proliferation.[17-19] Increased PDGFR signaling has been shown to play a role in the pathogenesis of PAH, and inhibition of this pathway has been shown to improve cardiopulmonary hemodynamics in patients with PAH[20-22]. A recent phase III trial of oral imatinib (a modest PDGFR and ABL inhibitor) for PAH met its primary endpoint[23]. However, imatinib administered orally was associated with significant systemic side effects, including GI side effects, bone marrow suppression, and increased bleeding[24].

The development of PK10571 (Structure X) and related compounds for direct pulmonary delivery, e.g., spray-dry powders (SDPs), which are also termed spray-dry dispersions (SDDs), imparts therapeutic indications possessing lower systemic—therapeutically efficacious—doses, and an improved therapeutic window for this class of drugs. A 45-fold greater drug level in present in the lung, when administered accordingly, compared to intravenous administration, i.e., 45-fold therapeutic advantage.[16] Compounds such as PK10571 have similar potency and selectivity against the PDGFR receptor, such as, e.g., PK10453 (Structure Y), greater potency in cell based assays of PDGFBB signaling, no adverse effect on healthy pulmonary arterial endothelial permeability or harrier function, a longer half-life in vivo than PK10453, and superior pre-clinical efficacy. See FIGS. 21-26.

Developing a drug for inhaled treatment of PAH requires attention to specific formulation requirements, such as, e.g., the drug product must be formulated to generate a stable inhalable particle that can be deposited in the lung when inhaled. Moreover, for PAH, the deposited drug must also exert an effect on the pulmonary vasculature, and, in particular, the pulmonary arteries and arterioles. The formulation should also exert a therapeutic effect by lowering pulmonary arterial pressure, decreasing pulmonary vascular resistance, or decreasing pathologic findings of the disease in the lung or circulation such as pulmonary fibrosis.

Efficacy is shown in patients by a variety of indicators, such as, e.g., bio markers including PDGF AA, PDGF BB, or PDGF AB, decrease in pulmonary vascular resistance and/or pulmonary hypertension as measured by cardiac catheterization, decrease in pulmonary as measured by echocardiography, improvement in right ventricular function as measured by echocardiography or MRI, decreased pulmonary metabolic activity as measured by PET scanning, increased exercise capacity as measured by six-min walk distance, cardiopulmonary exercise testing, increased time to clinical worsening, increased survival, decreased number of hospitalizations, decreased need to add additional medication for treatment, decreased need for lung transplantation, and/or decreased need for atrial septostomy.

The present disclosure also relates to, inter alia, a novel class of compounds which function as kinase inhibitors. Likewise, methods for using such compounds in the prevention and treatment of disease conditions are disclosed herein. The present disclosure further relates to pharmaceutical formulations of the compounds, which possess prophylactic and/or therapeutic indications for subjects in need of kinase inhibitors, e.g., patients afflicted with vascular disease, proliferative disorders, cancers, and related diseases or conditions, as further detailed below. The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "an amino acid" includes a combination of two or more nucleic acids, and the like. Moreover, as used herein, the following abbreviations have certain meanings as detailed below.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the following PK compounds and structure designations are used interchangeably throughout the application: PK10453=Structure 2; PK10571=Structure 2a; PK10467=Structure 3; PK10468=Structure 4; and PK10569=Structure 5.

As used herein, the "administration" of an agent or drug, e.g., one or more kinase inhibitor compounds, to a subject or subjects includes any route of introducing or delivering to a subject a compound to perform its intended function. Administration can be carried out by any suitable route, including orally, intranasally, by inhalation, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and where some biologically or medically relevant result is achieved.

As used herein, the terms "comparable" or "corresponding" in the context of comparing two or more samples, responses to treatment, or drugs, refer to the same type of sample, response, treatment, and drug respectively used in the comparison. For example, the phosphorylation state or level of AKT (pAKT) in a sample can be compared to the phosphorylation state or level in another sample. In some embodiments, comparable samples may be obtained from the same individual at different times. In other embodiments, comparable samples may be obtained from different individuals, e.g., a patient and a healthy individual. In general, comparable samples are normalized by a common factor for control purposes.

As used herein, the term "composition" refers to a product with specified ingredients in the specified amounts, as well as any product which results, directly or indirectly, from combination of the specified ingredients in the specified amounts.

As used herein, the terms "drug," "compound," "active agent," "agent," "actives," "pharmaceutical composition," "pharmaceutical formulation," and "pharmacologically active agent" are used interchangeably and refer to any chemical compound, complex or composition, charged or uncharged, that is suitable for administration and that has a beneficial biological effect, suitably a therapeutic effect in the treatment of a disease or abnormal physiological condition, although the effect may also be prophylactic in nature. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent," and "API" (active pharmaceutical ingredient) are used, then, or when a particular active agent is specifically identified, it is to be understood that applicants intend to include the active agent per se as well as pharmaceutically acceptable, pharmacologically active salts, esters, amides, prodrugs, metabolites, analogs, etc.

As used herein, the terms "effective amount" or "pharmaceutically effective amount" or "Therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

As used herein, the terms "irreversible" or "irreversibly" when referring to a kinase inhibitor means an inhibitor of the activity of a kinase, tyrosine kinase, and/or RTK, which is covalently, i.e., permanently, bound or associated with such a kinase.

As used herein, the term "neoplastic disease" refers to cancers of any kind and origin and precursor stages thereof. Accordingly, the term "neoplastic disease" includes the subject matter identified by the terms "neoplasia", "neoplasm", "cancer", "pre-cancer" or "tumor." A neoplastic disease is generally manifest by abnormal cell division resulting in an abnormal level of a particular cell population. Likewise, because the monoclonal expansion of endothelial cells may refer to a "neoplasm" of the pulmonary arteriolar endothelial cells, PAH is also encompassed within the foregoing terms. The abnormal cell division underlying a neoplastic disease, moreover, is typically inherent in the cells and not a normal physiological response to infection or inflammation. In some embodiments, neoplastic diseases for diagnosis using methods provided herein include carcinoma.

As used herein, the term "non-selective", when referring to a kinase inhibitor or receptor kinase inhibitor, means an inhibitor of the activity of a kinase, tyrosine kinase, domain, and/or RTK, which is not solely specific to a single kinase, receptor, tyrosine kinase, RTK or domain, i.e., a cognate target, but within the context of inhibiting a single kinase, receptor, tyrosine kinase, RTK, domain, etc., e.g., for PDGFR, the inhibitor is non-specific with respect to affinities and/or $IC_{50}$ concentrations for the kinase, receptor, tyrosine kinase, RTK, domain, etc. For example, PK10453 (Structure 2) targets PDGFR, non-selectively, by inhibiting both PDGFR-β and PDGFR-α isoforms, but nevertheless may still possesses a lower $IC_{50}$ for a receptor isoform, e.g., PDGFR-β.

As used herein, the term "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, lactic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

As used herein, the term "reference level" refers to a level of a substance which may be of interest for comparative purposes. In some embodiments, a reference level may be a specified composition dosage as an average of the dose level from samples taken from a control subject. In other embodiments, the reference level may be the level in the same subject at a different time, e.g., a time course of administering, such as a level at 2, 4, 6, 8, and 10 minutes (min), etc.

As used herein, the terms "treating" or "treatment" or "alleviation" refer to both therapeutic treatment and prophylactic or preventative measures, wherein the objective is to prevent or slow down (lessen) the targeted pathologic condition or disorder. A subject is successfully "treated" for a disorder if, after receiving a therapeutic agent according to the methods of the present invention, the subject shows observable and/or measurable reduction in or absence of one or more signs and symptoms of a particular disease or condition.

As used herein, the term "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cycloalkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norhornyl, and bicyclo [2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. In some embodiments, unsubstituted alkyl groups include straight and branched chain alkyl groups having from 1 to 3 carbon atoms and include methyl, ethyl, propyl, and —CH(CH$_3$)$_2$.

As used herein, the term "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. In suitable embodiments, substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

As used herein, the term "unsubstituted aryl" refers to aryl groups that do not contain heteroatoms. Thus the term includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Unsubstituted aryl groups may be bonded to one or more carbon, oxygen, nitrogen, and/or sulfur atom(s).

As used herein, the term "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the term "substituted aryl" includes, but is not limited to, tolyl and hydroxyphenyl, among others.

As used herein, the term "unsubstituted alkenyl" refers to straight and branched chain and cyclic groups such as those described with respect to unsubstituted alkyl groups as defined above, except that at least one double bond exists between two carbon atoms. Non-limiting examples include vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, cyclohexenyl, cyclopentenyl, cyclohexadienyl, butadienyl, pentadienyl, and hexadienyl among others.

As used herein, the term "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon/non-hydrogen atoms is bonded to a carbon not involved in a carbon double bond.

As used herein, the term "unsubstituted alkynyl" refers to straight and branched chain groups such as those described with respect to unsubstituted alkyl groups as defined above, except that at least one triple bond exists between two carbon atoms. Examples include, but are not limited to, —C═C(H), —C═C(CH₃), —C═C(CH₂CH₃), —C(H₂)C═C(H), —C(H)₂C═C(CH₃), and —C(H)₂C═C(CH₂CH₃), among others.

As used herein, the term "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a carbon triple bond.

As used herein, the term "unsubstituted aralkyl" refers to unsubstituted alkyl groups as defined above in which a hydrogen or carbon bond of the unsubstituted alkyl group is replaced with a bond to an aryl group as defined above. For example, methyl (—CH₃) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group, i.e., a benzyl group. Thus, the term includes, but is not limited to, groups such as benzyl, diphenylmethyl, and 1-phenylethyl(—CH(C₆H₅)(CH₃)), among others.

As used herein, the term "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom. Non-limiting examples of substituted aralkyl groups include —CH₂C(═O)(C₆H₅), and —CH₂(2-methylphenyl), among others.

As used herein, the term "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridinyl, dihydropyridinyl, pyrimidyl, pyrazinyl, pyridazinyl, triazolyl, e.g., 4H-1,2.4-triazolyl, 1H-1,2,3-triazolyl, 2H-1,2,3-triazolyl etc., tetrazolyl, e.g., 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl, e.g., 1,2,4-oxadiazolyl, 1,3,4-oxadiazolyl, 1,2,5-oxadiazolyl, etc.; saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl, e.g. 2H-1,4-benzoxazinyl, etc.); unsaturated 3 to 8 membered rings containing 1 to 3 sulfur atoms and 1 to 3 nitrogen atoms such as, but not limited to, thiazolyl, isothiazolyl, thiadiazolyl, e.g., 1,2,3-thiadiazolyl, 1,2,4-thiadiazolyl, 1,3,4-thiadiazolyl, 1,2,5-thiadiazolyl, etc.; saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl, e.g., 2H-3,4-dihydrobenzothiazinyl, etc., unsaturated 3 to 8 membered rings containing oxygen atoms such as, but not limited to furyl; unsaturated condensed heterocyclic rings containing 1 to 2 oxygen atoms such as benzodioxolyl, e.g., 1,3-benzodioxoyl, etc.; unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene oxide and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiophene, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

As used herein, the term "substituted heterocyclyl" refers to an unsubstituted heterocyclyl group as defined above in which one or more of the ring members are bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, N-alkyl piperazinyl groups such as 1-methyl piperazinyl, piperazine-N-oxide, N-alkyl piperazine N-oxides, 2-phenoxy-thiophene, and 2-chloropyridinyl among others. In addition, substituted heterocyclyl groups also include heterocyclyl groups in which the bond to the non-hydrogen atom is a bond to a carbon atom that is part of a substituted and unsubstituted aryl, substituted and unsubstituted aralkyl, or unsubstituted heterocyclyl group. Examples include but are not limited to 1-benzylpiperidinyl 3-phenythiomorpholinyl, 3-(pyrrolidin-1-yl)-pyrrolidinyl, and 4-(piperidin-1-yl)-piperidinyl. Groups such as N-alkyl substituted piperazine groups such as N-methyl piperazine, substituted morpholine groups, and piperazine N-oxide groups such as piperazine N-oxide and N-alkyl piperazine N-oxides are examples of some substituted heterocyclyl groups. Groups such as substituted piperazine groups such as N-alkyl substituted piperazine groups such as N-methyl piperazine and the like, substituted morpholine groups, and N-oxide groups are examples of some substituted heterocyclyl groups that are suited for various "R" groups.

As used herein, the term "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—CH₃) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

As used herein, the term "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group. In addition, a substituted heterocyclylalkyl group also includes groups in which a carbon bond or a hydrogen bond of the alkyl part of the group is replaced by a bond to a substituted and unsubstituted aryl or substituted and unsubstituted aralkyl group.

As used herein, the term "unsubstituted alkylaminoalkyl" refers to an unsubstituted alkyl group as defined above in which a carbon or hydrogen bond is replaced by a bond to a nitrogen atom that is bonded to a hydrogen atom and an unsubstituted alkyl group as defined above. For example, methyl (—CH$_3$) is an unsubstituted alkyl group. If a hydrogen atom of the methyl group is replaced by a bond to a nitrogen atom that is bonded to a hydrogen atom and an ethyl group, then the resulting compound is —CH$_2$—N(H)(CH$_2$CH$_3$) which is an unsubstituted alkylaminoalkyl group.

As used herein, the term "substituted alkylaminoalkyl" refers to an unsubstituted alkylaminoalkyl group as defined above except where one or more bonds to a carbon or hydrogen atom in one or both of the alkyl groups is replaced by a bond to a non-carbon or non-hydrogen atom as described above with respect to substituted alkyl groups except that the bond to the nitrogen atom in all alkylaminoalkyl groups does not by itself qualify all alkylaminoalkyl groups as being substituted.

As used herein, the term "unsubstituted dialkylaminoalkyl" refers to an unsubstituted alkyl group as defined above in which a carbon bond or hydrogen bond is replaced by a bond to a nitrogen atom which is bonded to two other unsubstituted alkyl groups as defined above.

As used herein, the term "substituted dialkylaminoalkyl" refers to an unsubstituted dialkylaminoalkyl group as defined above in which one or more bonds to a carbon or hydrogen atom in one or more of the alkyl groups is replaced by a bond to a non-carbon and non-hydrogen atom as described with respect to substituted alkyl groups. The bond to the nitrogen atom in all dialkylaminoalkyl groups does not itself qualify all dialkylaminoalkyl groups as substituted.

As used herein, the term "unsubstituted alkoxy" refers to a hydroxyl group (—OH) in which the bond to the hydrogen atom is replaced by a bond to a carbon atom of an otherwise unsubstituted alkyl group as defined above. As used herein, the term "substituted alkoxy" refers to a hydroxyl group (—OH) in which the bond to the hydrogen atom is replaced by a bond to a carbon atom of an otherwise substituted alkyl group as defined above.

As used herein, the term "unsubstituted heterocyclyloxy" refers to a hydroxyl group (—OH) in which the bond to the hydrogen atom is replaced by a bond to a ring atom of an otherwise unsubstituted heterocyclyl group as defined above. As used herein, the term "substituted heterocyclyloxy" refers to a hydroxyl group (—OH) in which the bond to the hydrogen atom is replaced by a bond to a ring atom of an otherwise substituted heterocyclyl group as defined above. As used herein, the term "unsubstituted heterocyclyloxyalkyl" refers to an unsubstituted alkyl group as defined above in which a carbon bond or hydrogen bond is replaced by an oxygen bond, which is bonded to an unsubstituted heterocyclyl group.

As used herein, the term "substituted heterocyclyloxyalkyl" refers to an unsubstituted heterocyclyloxyalkyl group as defined above in which a bond to a carbon or hydrogen group of the alkyl group of the heterocyclyloxyalkyl group is bonded to a non-carbon and non-hydrogen atom as described above with respect to substituted alkyl groups or in which the heterocyclyl group of the heterocyclyloxyalkyl group is a substituted heterocyclyl group as defined above.

As used herein, the term "unsubstituted heterocyclylalkoxy" refers to an unsubstituted alkyl group as defined above in which a carbon bond or hydrogen bond is replaced by a bond to an oxygen atom which is bonded to the parent compound, and in which another carbon or hydrogen bond of the unsubstituted alkyl group is bonded to an unsubstituted heterocyclyl group as defined above. As used herein, the term "substituted heterocyclylalkoxy" refers to an unsubstituted heterocyclylalkoxy group as defined above in which a bond to a carbon or hydrogen group of the alkyl group of the heterocyclylalkoxy group is bonded to a non-carbon and non-hydrogen atom as described above with respect to substituted alkyl groups or in which the heterocyclyl group of the heterocyclylalkoxy group is a substituted heterocyclyl group as defined above. Further, a substituted heterocyclylalkoxy group also includes groups in which a carbon bond or a hydrogen bond to the alkyl moiety of the group may be substituted with one or more additional substituted and unsubstituted heterocycles.

As used herein, the term "unsubstituted arylaminoalkyl" refers to an unsubstituted alkyl group as defined above in which a carbon bond or hydrogen bond is replaced by a bond to a nitrogen atom which is bonded to at least one unsubstituted aryl group as defined above.

As used herein, the term "substituted arylaminoalkyl" refers to an unsubstituted arylaminoalkyl group as defined above except where either the alkyl group of the arylaminoalkyl group is a substituted alkyl group as defined above or the aryl group of the arylaminoalkyl group is a substituted aryl group except that the bonds to the nitrogen atom in all arylaminoalkyl groups does not by itself qualify all arylaminoalkyl groups as being substituted. However, substituted arylaminoalkyl groups does include groups in which the hydrogen bonded to the nitrogen atom of the group is replaced with a non-carbon and non-hydrogen atom.

As used herein, the term "unsubstituted heterocyclylaminoalkyl" refers to an unsubstituted alkyl group as defined above in which a carbon or hydrogen bond is replaced by a bond to a nitrogen atom which is bonded to at least one unsubstituted heterocyclyl group as defined above. As used herein, the term "substituted heterocyclylaminoalkyl" refers to unsubstituted heterocyclylaminoalkyl groups as defined above in which the heterocyclyl group is a substituted heterocyclyl group as defined above and/or the alkyl group is a substituted alkyl group as defined above. The bonds to the nitrogen atom in all heterocyclylaminoalkyl groups does not by itself qualify all heterocyclylaminoalkyl groups as being substituted.

As used herein, the term "unsubstituted alkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to a hydrogen atom and an unsubstituted alkyl group as defined above.

As used herein, the term "substituted alkylaminoalkoxy" refers to unsubstituted alkylaminoalkoxy groups as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if the hydrogen bonded to the amino group is bonded to a non-carbon and non-hydrogen atom and/or if the alkyl group bonded to the nitrogen of the amine is bonded to a non-carbon and non-hydrogen atom as described above with respect to substituted alkyl groups. The presence of the amine and alkoxy functionality in all alkylaminoalkoxy groups does not by itself qualify all such groups as substituted alkylaminoalkoxy groups.

As used herein, the term "unsubstituted dialkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to two other similar or different unsubstituted alkyl groups as defined above.

As used herein, the term "substituted dialkylaminoalkoxy" refers to an unsubstituted dialkylaminoalkoxy group as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if one or more of the alkyl groups bonded to the nitrogen of the amine is bonded to a non-carbon and non-hydrogen atom as described above with respect to substituted alkyl groups. The presence of the amine and alkoxy functionality in all dialkylaminoalkoxy groups does not by itself qualify all such groups as substituted dialkylaminoalkoxy groups.

As used herein, the term "protected" with respect to hydroxyl groups, amine groups, and sulfhydryl groups refers to forms of these functionalities which are protected from undesirable reaction with a protecting group known to those skilled in the art such as those set forth in *Protective Groups in Organic Synthesis*, Greene, T. W.; Wuts, P. G. M., John Wiley & Sons, New York, N.Y., (3rd Edition, 1999), which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, e.g., methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Non-limiting examples of protected amine groups include amides such as, formamide, acetamide, trifluoroacetamide, and benzamide; imides, such as phthalimide, and dithiosuccinimide; and others. Non-limiting examples of protected sulfhydryl groups include thioethers such as S-benzyl thioether, and S-4-picolyl thioether; substituted S-methyl derivatives such as hemithio, dithio and aminothio acetals, among others.

Overview

Various compounds have been found useful in treating certain diseases such as, e.g., cancer. For example, Gleevec® (imatinib mesylate or "imatinib") is a compound that has shown efficacy in treating chronic myeloid leukemia (CML) and gastrointestinal stromal tumors (GIST). Other experimental drugs include sorafenib and PNU-166196 for the respective treatment of renal cell carcinoma and leukemia. Although significant advances have been made in the development of pharmaceutical compositions for treating certain cancers; new compounds, compositions, methods of treatment, and model systems for developing drugs are required for preventing and/or treating cancer and other diseases, e.g., pulmonary-vascular disease such as pulmonary arterial hypertension (PAH). In particular, platelet derived growth factor (PDGF) receptor tyrosine kinases are an attractive therapeutic target for PAH. The PDGF signaling pathway is activated in human idiopathic PAH (iPAH) and in animal models of the disease. For example, PDGFA, PDGFB, PDGFRα, and PDGFRβ mRNA expression is increased in small pulmonary arteries from patients with iPAH compared to control subjects, and Western blot analysis shows a significant increase in protein expression of PDGFRβ in PAH lungs.

The migration of PASMCs is inhibited by imatinib, a PDGFRα inhibitor. Imatinib also decreases RVSP and improved survival in the rat MCT model of PAH. In several case reports of patients with refractory PAH, a favorable response to imatinib has been observed. See Ghofrani et al., "Imatinib in pulmonary arterial hypertension patients with inadequate response to established therapy." *Am J Respir Crit Care Med. Vol.* 182:1171-7 (2010). The IMPRES trial, which examined the effect of imatinib in patients with severe PAH, showed an improvement in the six minute walk distance and in cardiopulmonary hemodynamics. However, orally administered imatinib may be associated with systemic side effects including gastrointestinal distress and bone marrow suppression. See Paniagua et al., "Imatinib for the treatment of rheumatic diseases: *Nat Clin Pract Rheumatol; Vol* 3:190-1 (2007). To improve the therapeutic window, i.e., increase efficacy and decrease systemic side-effects, the present inventors employed inhalation delivery of kinase inhibitors for PAH.

Imatinib, moreover, was developed using an in vivo murine MCT model system, which is an imperfect system concerning preclinical drug candidate efficacy assessment at least because it is unreliable with respect to expressing certain human disease phenotypes, e.g., the development of neointimal and/or plexiform lesions associated with PAH. Cool et al., "Pathogenesis and evolution of plexiform lesions in pulmonary hypertension associated with scleroderma and human immunodeficiency virus infection." *Hum Pathol.* 28:434-442 (1997). Therefore, examining the effects of kinase inhibitors in more aggressive models presenting human disease phenotypes is essential for more accurately reflecting the pathology of the human disease and, consequently, the development of the next generation of compounds and compositions for effectively treating human disease.

The present inventors have employed such a model, while further comparing the present compounds and therapies to imatinib. As further detailed below, the present inventors performed efficacy studies using a murine monocrotaline (MCT) plus pneumonectomy (PN) model system (MCT+PN). This model imparts neointimal and/or plexiform lesions characteristic of human disease, e.g., PAH. To this end, for example, the pathologic signature of PAH consists of concentric and plexiform lesions in small precapillary pulmonary arterioles. See Cool et al. (1997); and Tuder et al., "Plexiform lesion in severe pulmonary hypertension: association with glomeruloid lesion." *Am J Pathol* 159:382-

383 (2001). Concentric lesions arise from the proliferation of neointimal cells, which occlude the vessel lumen. It has been reported that these concentric obstructive neointimal lesions are composed of myofibroblasts and/or endothelial cells. See, e.g., Yi et al., *Am J Respir Grit Care Med* 162:1577-86 (2000).

In addition, perivascular infiltrates, consisting of T cells, B cells, and macrophages, have been found in plexogenic PAH. See Sakagami, "In vivo, in vitro and ex vivo models to assess pulmonary absorption and disposition of inhaled therapeutics for systemic delivery." *Adv Drug Deliv Rev* 58:1030-1060 (2006). Plexiform lesions, moreover, are characterized by disorganized vascular channels that stain for endothelial cell markers, and such lesions in lung samples from patients with idiopathic and/or primary PAH consist of a monoclonal expansion of endothelial cells. Lee et al., "Monoclonal endothelial cell proliferation is present in primary but not secondary pulmonary hypertension." *J Clin Invest* 101:927-934 (1998). As such, PAH of this type is essentially a "cancer" of pulmonary arteriolar endothelial cells (see id.), at least because in the initial or early stages of the disease, an acute apoptotic loss of normal endothelial cells may result in the emergence and clonal expansion of apoptosis resistant endothelial cells. Lee et al. (1998). The neoplastic process associated with PAH provides for not only kinase inhibitor treatment of PAH, but also the development of new compounds, compositions, and methods, via MCT+PN model determinations, with superior efficacy, potency and a broader spectrum of inhibition compared to previously generated kinase inhibitors using inferior model systems, which may possess a narrow selectivity for RTK inhibition, for the treatment of neoplastic disease. Drug-kinase homology modeling ensures that such inhibitors, including, for example, non-selective and irreversibly derivatives thereof, target vulnerable kinase domains for optimal efficacy, as further described below.

Compound Synthesis

In one aspect, the present disclosure provides for the synthesis of Structure I compounds, which are readily synthesized using the procedures described in the following sections and as disclosed in WO 2008/058341, which is hereby incorporated by reference in its entirety and for all purposes as if fully set forth herein. Compounds of Structure 1, moreover, are typically prepared from starting materials, such as, e.g., dihaloheterocycle. The first step is a nucleophilic aromatic substitution to generate a monoamino-monohalo intermediate. The nucleophilic aromatic substitution is typically carried out by addition of a primary or secondary amine to the di-halogenated heterocycle in a solvent such as ethanol, isopropanol, tert-butanol, dioxane, THF, DMF, ethoxyethanol, toluene or xylene. The reaction typically occurs at elevated temperature in the presence of excess amine or a non-nucleophilic base such as triethylamine or diisopropylethylamine, or an inorganic base such as potassium carbonate or sodium carbonate.

Alternatively, the amino substituent may be introduced through a transition metal catalyzed amination reaction. Typical catalysts for such transformations include Pd(OAc) 2/P(t-Bu)$_3$, Pd$_2$(dba)$_3$/BINAP and Pd(OAc)$_2$/BI AP. These reactions are typically carried out in solvents such as toluene or dioxane, in the presence of bases such as caesium carbonate or sodium or potassium tert-butoxide at temperatures ranging from room temperature to reflux. See, e.g., Hartwig and Angew, *Chem. Mt. Ed* 37, 2046 (1998). The amines employed in the first step of the synthesis of these compounds are obtained commercially or are prepared using methods well known to those skilled in the art. α-alkylbenzylamines, moreover, may be prepared through reduction of oximes. Typical reductants include lithium aluminium hydride, hydrogen gas in the presence of palladium on charcoal catalyst, Zn in the presence of hydrochloric acid, sodium borohydride in the presence of a Lewis acid such as TiCb, ZrCU, Q$_2$ and M0O$_3$, or sodium borohydride with Amberlyst HI 5 ion exchange resin and LiCl. α-alkylbenzylamines may also be prepared by reductive amination of the corresponding ketones. A classical method for such a transformation is the Leuckart-Wallach reaction, though catalytic conditions (HCO$_2$NH$_4$, [(CH3)$_5$C$_5$RhCl2]2) or other procedures, e.g., NH$_4$OAc, Na(CN)BH$_3$) are also used, α-Alkylbenzylamines may also be prepared from the corresponding α-alkylbenzyl alcohols. Such methods include derivatisation of the hydroxyl as a mesylate or tosylate and displacement with a nitrogen nucleophile, such as phthalimide or azide which is converted to the primary amine using conventional synthetic methods; or, displacement of the hydroxyl with a suitable nitrogen nucleophile under Mitsunobu-like conditions. α-alkylbenzyl alcohols can be prepared by reduction of the corresponding ketones with a reducing agent such as sodium borohydride in a solvent such as methanol. Alternatively, α-alkylbenzyl alcohols can be obtained through addition of an alkyl metal species (such as a Grignard reagent) to a benzaldehyde derivative, which is typically performed at room temperature or below in solvents such as tetrahydrofuran. α-Alkyl benzylamines of high optical purity may be prepared from chiral α-alkyl benzyl alcohols using the methods outlined above. The chiral α-alkyl benzyl alcohols may be obtained through chiral reduction of the corresponding ketones.

The monoamino-monohalo intermediate formed from the dihaloheterocycle and the amine described above, may then be further functionalized. For example, where the amine substituent bears an additional functional group, this functional group may be derivatized or functionalized using methods well-known to those skilled in the art. For example, a free primary amino group could be further functionalized to an amide, sulphonamide or urea functionality, or could be alkylated to generate a secondary or tertiary amine derivative. Preferable methods for the formation of an amide include coupling the amine with a carboxylic acid using coupling reagents such as dicyclohexylcarbodiimide, 1-(3-dimethylaminopropyl)-3-ethylcarbodiimide, diisopropylcarbodiimide or carbonyldiimidazole in solvents such as dichloromethane, tetrahydrofuran or 1,4-dioxane. Alternatively, the acid component may be activated by conversion to an acid chloride (using thionyl chloride, oxalyl chloride, bis(trichloromethyl) carbonate or cyanuric chloride) or to mixed anhydride species (using, for example, t-butyl chloroformate or isopropyl chloroformate) or to active ester intermediates (such as N-hydroxysuccinimidyl, pentafluorophenyl or p-nitrophenyl esters) prior to amine reaction.

The monoamino-monochloro intermediate may then be reacted in a palladium mediated cross-coupling reaction with a suitably functionalized coupling partner to replace the halogen atom with an alternative moiety. Typical coupling partners are organoboronic acids or esters. See, e.g., Miyaura and Suzuki, *Chem Rev.* 952457 (1995); Stille, *Chem., Int. Ed. Engl* 25, 508 (1986); Kumada et al., *Org. Synth. Coll. Vol.* 6, 407 (1998); and: Negishi, J. *Organomet. Chem.* 653, 34 (2002) for Suzuki coupling, organostannanes, Stille coupling, Grignard reagents, Kumada coupling, organozinc species, and Negishi coupling, respectively. The Suzuki coupling is the preferred coupling method and is typically performed in a solvent such as DME, THF, DMF, ethanol, propanol, toluene, or 1,4-dioxane in the presence of a base such as potassium carbonate, lithium hydroxide, caesium carbonate, sodium hydroxide, potassium fluoride or potassium phosphate. The reaction may be carried out at elevated temperatures and the palladium catalyst employed may be selected from $Pd(PPh_3)_4$, $Pd(OAc)_2$, $[PdCl_2(dppf)]$, $Pd_2(dba)_3/P(t-Bu)_3$.

The monoamino-monochloro intermediate may also be subjected to a second nucleophilic aromatic substitution reaction using similar conditions to those outlined above. Those skilled in the art will appreciate that the order of the reactions described for the syntheses above may be changed in certain circumstances and that certain functionalities may need to be derivatized, i.e., protected, in certain instances for the reactions described above to proceed with reasonable yield and efficiency. The types of protecting functionality are well-known to those skilled in the art. The products formed from the reaction sequences described above may be further derivatized using techniques well known to those skilled in the art. The leaving group may be any suitable known type such as those disclosed in March, "Advanced Organic Chemistry: Reactions, Mechanisms and Structure." 4th Ed. pp 352-7, John Wiley & Sons, NY (1992). In some embodiments, the leaving group is a halogen, e.g., chlorine.

Kinases

Protein kinases are a family of enzymes that catalyze the phosphorylation of specific residues in proteins. Such enzymes are generally categorized into three groups, those which preferentially phosphorylate serine and/or threonine residues, those which preferentially phosphorylate tyrosine residues, and those which phosphorylate both tyrosine and Ser/Thr residues. Protein kinases are therefore key elements in signal transduction pathways responsible for transducing extracellular signals, including the action of cytokines on their receptors, to the nuclei, triggering various biological events. The many roles of protein kinases in normal cell physiology include cell cycle control including proliferation, differentiation, metabolism, apoptosis, cell mobility, mitogenesis, transcription, translation and other signaling processes.

Platelet derived growth factor receptor kinase (PDGFR) is one type of RTK. The sequence of PDGFR can be found in GenBank, accession number NM-002609 (mRNA) and NP-002600 (protein) and has been described, at least, in Matsui, et al., "Isolation of a novel receptor cDNA establishes the existence of two PDGF receptor genes" *Science* 243(4892):800-804 (1989); Claesson-Welsh, L. et al. "cDNA cloning and expression of a human platelet-derived growth factor (PDGF) receptor specific for B-chain-containing PDGF molecules" Mol. Cell. Biol. 8(8):3476-3486 (1988); and Gronwald, et al. *PNAS.* 85(10):3435-3439 (1988).

Moreover, PDGFR's cognate binding ligand, PDGF, is a strong mitogenic factor for cells of mesenchymal origin such as fibroblasts, smooth muscle cells, and glial cells. PDGF is a 32 kDa protein heterodimer usually composed of two polypeptide chains, A and B, linked by disulfide bonds. In addition to the PDGF AB heterodimer, two homodimeric forms of PDGF exist (AA and BB). During blood clotting and platelet adhesion, the PDGF is released from granules at sites of injured blood vessels, suggesting that PDGF may have a role in the repair of blood vessels. PDGF may stimulate migration of arterial smooth muscle cells from the medial to the intimal layer of the artery where the muscle cells may proliferate. The cellular proliferation induced by all isoforms of PDGF is mediated by ligand binding to the PDGF receptor. The PDGF receptor belongs to the class III tyrosine kinase family and consists of two receptor subtypes, termed type A (or type alpha), and type B (or type beta), as detailed above. Other members of the PDGF receptor family include CSF-IR, cKIT and FLT3. The two PDGF receptor isoforms may be distinguished by their markedly different ligand binding specificities. PDGFβ receptor binds only B-chain (isoforms BB and AB), while PDGF a receptor can bind all forms of PDGF (isoforms containing A and/or B chain). With the importance of PDGF-related processes to proliferation of endothelial cells and vascular smooth muscle, there are a range of pathogenic processes that PDGFRβ kinase inhibitors are useful for, e.g., disease prevention and treatment.

PDGF expression has been shown in a number of different solid tumors, from glioblastomas to prostate carcinomas. In these various tumor types, the biological role of PDGF signaling can vary from autocrine stimulation of cancer cell growth to more subtle paracrine interactions involving adjacent stroma and angiogenesis. Therefore, inhibiting the PDGFR kinase activity with small molecules may interfere with tumor growth, angiogenesis, diseases with neoplastic etiologies, immunological and inflammatory diseases, hyperproliferative diseases including cancer and diseases involving neo-angiogenesis, renal and kidney diseases, bone remodeling diseases, metabolic diseases, vascular diseases, and pulmonary vascular diseases such as, e.g., PAH. Other diseases mediated by PDGF, and thus involving its cognate receptors, include, for example, restenosis, including coronary restenosis after angioplasty, atherectomy, or other invasive methods of plaque removal, and renal or peripheral artery restenosis after the same procedures; vascular proliferative phenomena and fibrosis associated with other forms of acute injury such as pulmonary fibrosis associated with adult respiratory distress syndrome, renal fibrosis associated with nephritis, coronary stenosis associated with Kawasake's disease and vascular narrowings associated with other arteritides such as Takayasha's disease; prevention of narrowings in vein grafts; prevention of narrowings due to accelerated smooth muscle cell migration and proliferation in transplanted organs, and other fibrotic processes, such as scleroderma and myofibrosis and inhibition of tumor cell proliferation.

c-Kit is another receptor tyrosine kinase belonging to PDGF Receptor family and is normally expressed in hematopoictic progenitor, mast and germ cells, c-kit expression has been implicated in a number of cancers including mast cell leukemia, germ cell tumors, small-cell lung carcinoma, GIST, acute myelogenous leukemia (AML), neuroblastoma, melanoma, ovarian carcinoma, breast carcinoma. Smolich et al., *Blood,* 97(5) 1413-21.

Extracellular signal-regulated protein kinases 1 and 2 (ERK1/2) are members of the mitogen-activated protein (MAP) kinase super family that can mediate cell proliferation and apoptosis. The Ras-Raf-MEK-ERK signaling cascade controlling cell proliferation has been well studied but the mechanisms involved in ERK1/2-mediated cell death are largely unknown. ERK1/2 translocates to the nucleus, but can also remain in the cytosol. Cytosolic retention of ERK1/2 denies access to the transcription factor substrates that are responsible for the mitogenic response. In addition, cytosolic ERK1/2, besides inhibiting survival and proliferative signals in the nucleus, potentiates the catalytic activity of some proapoptotic proteins such as DAP kinase in the cytoplasm. Studies that further define the function of cytosolic ERK1/2 and its cytosolic substrates that enhance cell death will be essential to harness this pathway for developing effective treatments for cancer and chronic inflammatory diseases.

STAT3 is a member of the STAT protein family, which typical function in response to cytokines and growth factors. STAT family members are phosphorylated by the receptor associated kinases, and then form homo- or heterodimers that translocate to the cell nucleus where they act as transcription activators. STAT3 is activated through phosphorylation in response to various cytokines and growth factors including IFNs, EGF, ILS, IL6, HGF, LIF and BMP2. This protein mediates the expression of a variety of genes in response to cell stimuli, and thus plays a key role in many cellular processes such as cell growth and apoptosis. The small GTPase Rac1 has been shown to bind and regulate the activity of this protein, while PIAS3 has been shown to inhibit STAT3.

AKT (also known as PKB) is involved in the regulation of metabolism, cell survival, motility, transcription and cell-cycle progression. AKT belongs to the AGC subfamily of the protein kinase superfamily, which consists of more than 500 members in humans. The AKT subfamily comprises three mammalian isoforms, Akt1, Akt2, and Akt3, which are products of distinct genes and share a conserved structure that includes three functional domains: an N-terminal pleckstrin homology (PH) domain, a central kinase domain, and a C-terminal regulatory domain containing the hydrophobic motif (HM) phosphorylation site [FxxF(S/T)Y].

Kinase Inhibitors

In one aspect, the present disclosure provides compounds and methods of inhibiting a kinase, e.g., a tyrosine kinase, such as a RTK, in a subject and/or a method of treating a biological condition mediated by, or associated with, a kinase, e.g., a tyrosine kinase, such as a RTK, in a subject. In some embodiments, the kinase is Cdc2 kinase, AKT, c-Kit, c-ABL, ERK1/2, STAT3, p60src, VEGFR3, PDGFRα, PDGFRβ, FGFR3, PDGFR-αα, PDGFR-ββ, PDGFR-αβ, FLT-3, Fyn, Lck, Tie-2, GSK-3, Cdk2, Cdk4, MEK1, NEK-2, CHK2, CKIε, Raf, CHK1, Rsk2, FMS (CSF-IR), KDR, EphA2, EphA3, EphA8, FLT1, FLT4, HCK, PTK5, RET, SYK, DDR1, DDR2 and PAR-1. Likewise, the kinase is a tyrosine kinase, such as, e.g., Cdc2 kinase, c-Kit, c-ABL, p60src, VEGFR3, PDGFRα, PDGFRβ, FGFR3, PDGFR-αα, PDGFR-ββ, PDGFR-αβ, FLT-3, Fyn, Lck, and/or Tie-2, in some embodiments. The methods include administering to the subject a compound of Structure I, a tautomer of the compound, a pharmaceutically acceptable salt of the compound, a pharmaceutically acceptable salt of the tautomer, or mixtures thereof.

Previously, various indolyl substituted compounds are shown to inhibit one or more kinases, as disclosed in WO 01/29025, WO 01/62251, and WO 01/62252. Likewise, various benzimidazolyl compounds have recently been disclosed in WO 01/28993. Such compounds are reported to be capable of inhibiting, modulating, and/or regulating signal transduction of both receptor-type and non-receptor tyrosine kinases. Some of the disclosed compounds contain a quinolone fragment bonded to the indolyl or benzimidazolyl group. The synthesis of 4-hydroxy quinolone and 4-hydroxy quinoline derivatives has also been reported. For example, Ukrainets et al. have disclosed the synthesis of 3-(benzimidazol-2-yl)-4-hydroxy-2-oxo-1,2-dihydroquinoline. Ukrainets et al., Tet. Lett. 42, 7747-48 (1995) has also disclosed the synthesis, anticonvulsive and antithyroid activity of other 4-hydroxy quinolones and thio analogs such as 1H-2-oxo-3-(2-benzimidazolyl)-4-hydoxyquinoline. Ukrainets et al., Khimiya Geterotsiklicheskikh Soedinii, 1, 105-108 (1993). Other compounds, moreover, such as, for example, 4-Amino-5-fluoro-3-[5-(4-methylpiperazin-1-yl)-1H-benzimidazol-2-yl]quinolin-2(1H)-one has been described as an orally bioavailable benzimidazole-quinolinone that exhibits inhibition of receptor tyrosine kinases that drive both endothelial and tumor cell proliferation. The inhibitory effect was shown on nine tyrosine kinases, FGFR1, FGFR3, VEGFR1, VEGFR2, VEGFR3, PDGFRβ, c-Kit, p60src, and FLT-3, as disclosed in WO 2005/047244. However, this compound does not significantly inhibit EGFR family kinases or insulin receptor kinases at pharmaceutically acceptable doses.

Moreover, 4-(4-methylpiperazin-1-ylmethyl)-N-[4-methyl-3-(4-pyridin-3-yl)pyrimidin-2-ylamino)phenyl]-benzamide (imatinib), as disclosed in US 2006/0154936, inhibits PDGFRα and β kinases, Abl, DDR, and c-KIT, as described in US 2011/0190313. Paragraph [0117] of US 2011/0190313, however, indicates that although imatinib appeared safe and well tolerated over a 6 month period, the primary efficacy parameter (6MWD) did not improve in patients randomized to imatinib compared with placebo, despite significant improvement in secondary endpoints. A continuing need therefore exists for compounds that inhibit, kinases, e.g., tyrosine kinases, such as RTKs, at least because of previous limitations, resistant disease phenotypes, and the need for more effective kinase, e.g., RTK, inhibition, as further detailed below. See US 2008/0268460.

Furthermore, the small molecules that were reported in Frey et al. (1998) were shown to irreversibly inhibit epidermal growth factor receptor (EGFR) by covalently interacting with the receptor, while alkylating a cysteine residue in the ATP binding pocket of the molecule. Indeed, Leproult et al., "Cysteine Mapping in Conformational Distinct Kinase Nucleotide Binding Sites: Application to the Design of Selective Covalent Inhibitors." J. Med. Chem. 54, 1347-1355 (2011), discloses that one approach to designing irreversible inhibitors is to exploit the nucleophilicity of a cysteine thiol group present in the target protein via systematic analysis of cysteine residues present in the nucleotide binding site of kinases. Such an approach can facilitate irreversible inhibition even when taking into consideration the different kinase conformations and therefore improve dosing and toxicity. See id.

The cysteine mapping in Leproult et al. (2011) demonstrate that kinases are potential targets for selective covalent inhibitors. An example is shown of the kinase inhibitor imatinib to which a chloroacetamide group is added in the para position of the benzene ring. Peptide inhibitor adduct formation was shown for both Kit and PDGFα receptors. Id. However, other compounds failed to show similar covalent adducts. Chloroacetamide is shown as an example of an electrophile which can form a covalent bond with a cysteine residue. The general term "warhead" is used to mean an electrophilic trap for forming a covalent bond between the inhibitor and the targeted protein kinase. Chloroacetamide as an electrophile may be too reactive to have clinical utility and may have toxicity for this reason. Leproult et al. (2011) nevertheless suggest that less then optimal positioning of the electrophile could explain why a covalent bond may not form with other less reactive warheads.

The present disclosure provides for, inter alia, distinct warhead positioning on RTK receptor inhibitors. In some embodiments, electrophiles other than those described by Leproult et al. (2011), were employed for increased efficacy. See Barf et al. (2012) and Oballa et al., "A generally applicable method for assessing the electrophilicity and reactivity of diverse nitrile-containing compounds." Bioorg Med Chem Lett 17:998-1002 (2007) (describing nitrile-containing electrophiles). Furthermore, Diller et al., J Med Chem 46:4638-4647 (2003) reported a homology model of the PDGF receptor based on VEGFR2 (55% homology).

Molecular docking was previously employed by the inventors with respect to one aspect of the present invention by using homology models of RTK, based on homologous structures, e.g., PDGFα and PDGFβ receptor homology to c-Kit is 59% and 63%, respectively. In some embodiments, the introduction of various electrophiles in a variety of positions with respect to a RTK inhibitor, e.g., PDGFR inhibitor, scaffold provided the bases for further biochemical analyses. To this end, the spatial orientation of the inhibitor warheads, relative to the target cysteine residues, can be analyzed to calculate the free energy of binding and estimated $K_i$. In some embodiments, compounds with the lowest free energy of binding and closest proximity of the warhead to a cysteine residue impart irreversible non-selective RTK inhibitors.

Accordingly, the present disclosure provides compounds of Structure 1, the enantiomer, isomer or stereoisomer of the compound, a pharmaceutically acceptable salt of the compound, tautomer, enantiomer, isomer or stereoisomer of the compound, or any mixtures thereof, which covalently interact with a receptor tyrosine kinase (RTK), such as, for example, PDGFR or c-Kit or both. In some embodiments, the PDGFR is selected from the group consisting of PDGFR-α, PDGFR-β, PDGFR-αα, PDGFR-ββ, and PDGFR-αβ as demonstrated via homology modeling.

Pharmaceutical Compositions

In one aspect, the present disclosure provides pharmaceutical compositions which include at least one of the compounds of Structure 1 and a pharmaceutically acceptable carrier. The compositions of the present invention may contain other therapeutic agents as described below, and may be formulated, for example, by employing conventional solid or liquid vehicles or diluents, as well as pharmaceutical additives of a type appropriate to the mode of desired administration, for example, excipients, binders, preservatives, stabilizers, flavors, etc., according to techniques such as those well known in the art of pharmaceutical formulation.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment for a treatment course.

The compounds of the present disclosure are administered by any suitable means, for example, orally, such as in the form of tablets, capsules, granules or powders; sublingually; buccally; parenterally, such as by subcutaneous, intravenous, intramuscular, intra(trans)dermal, or intracisternal injection or infusion techniques, e.g., as sterile injectable aqueous or non-aqueous solutions or suspensions, nasally such as by inhalation spray or insufflation, topically, such as in the form of a cream or ointment ocularly in the form of a solution or suspension, vaginally in the form of pessaries, tampons or creams, or rectally such as in the form of suppositories, in unit dosage formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, for extended release, by the use of devices such as subcutaneous implants or osmotic pumps.

For administration to the respiratory tract, e.g., inhalation, including intranasal administration, the active compound may be administered by any of the methods and formulations employed in the art for administration to the respiratory tract. Thus, the active compound may be administered in the form of, e.g., a solution, suspension, or as a dry powder. The agents according to this aspect of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The propellant-driven inhalation aerosols which may be used according to the invention may also contain other ingredients such as co-solvents, stabilizers, surfactants, antioxidants, lubricants and pH adjusters. The propellant-driven inhalation aerosols according to the invention which may be used according to the invention may be administered using inhalers known in the art, e.g., metered dose inhalers. As another alternative, the agents of the present invention may be administered to the airways in the form of a lung surfactant formulation. The lung surfactant formulation can include exogenous lung surfactant formulations (e.g., Infasurf® (Forest Laboratories), Survanta® (Ross Products), and Curosurf® (DEY, California, USA) or synthetic lung surfactant formulations (e.g., Exosurl® (GlaxoWellcome Inc.) and ALEC). These surfactant formulations are administered via airway instillation (i.e., after intubation) or intratracheally.

As a further alternative, the agents of the present invention may be administered to the airways in the form of an inhalable powder. The powder formulation may include physiologically acceptable excipients such as monosaccharides (e.g. glucose or arabinose), disaccharides (e.g. lactose, saccharose and maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in hydrate form.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipients mentioned above. These finer excipients are also selected from the group of possible excipients listed hereinbefore.

Finally, in order to prepare the inhalable powders according to the invention, micronised formulations, preferably with an average particle size of 0.5 to 10 μm is added to the excipient mixture. Processes for producing the inhalable powders according to the invention by grinding and micronizing and by finally mixing the ingredients together are known from the prior art.

In formulations intended for administration to the respiratory tract, including intranasal formulations, the active compound is typically configured to have a small particle size, e.g., approximately 5 microns or less, via micronisation techniques and the like. Sustained release formulations of the active compound are employed in some embodiments. The active compound, in some embodiments, is administered by oral inhalation as a free-flow powder via inhaler.

The pharmaceutical composition and method of the present disclosure further include additional therapeutically active compounds (second agents), as noted herein and/or known in the art, which are typically employed for treating one or more pathological conditions in concert with the compositions comprising compounds of Structure 1 of the present disclosure. The combination of therapeutic agents acts synergistically to effect the treatment or prevention of the various diseases, disorders, and/or conditions described herein. Such second agents, include, but are not limited to, of prostanoids, endothelin antagonists, cytoplasmic kinase inhibitors, receptor kinase inhibitors, endothelin receptor antagonists, e.g., ambrisentan, bosentan, and sitaxsentan, PDE5 (PDE-V) inhibitors, e.g., sildenafil, tadalafil, and vardenafil, calcium channel blockers, e.g., amlodipine, felodipine, varepamil, diltiazem, and menthol, prostacyclin, treprostinil, iloprost, beraprost, nitric oxide, oxygen, heparin, warfarin, diuretics, digoxin, cyclosporins, e.g., cyclosporin A, CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39, i.e., CD 154, fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen, aspirin, acetaminophen, leflunomide, deoxyspergualin, cyclooxygenase inhibitors such as celecoxib, steroids such as prednisolone or dexamethasone, gold compounds, beta-agonists such as salbutamol, LABAs such as salmeterol, leukotriene antagonists such as montelukast, antiproliferative agents such as methotrexate, FK506 (tacrolimus, Prograf), mycophenolate mofetil, cytotoxic drugs such as azathioprine, VP-16, etoposide, fludarabine, doxorubin, adriamycin, amsacrine, camptothecin, cytarabine, gemcitabine, fluorodeoxyuridine, melphalan and cyclophosphamide, antimetabolites such as methotrexate, topoisomerase inhibitors such as camptothecin, DNA alkylators such as cisplatin, kinase inhibitors such as sorafenib, microtubule poisons such as paclitaxel, TNF-α inhibitors such as tenidap, anti-TNF antibodies or soluble TNF receptor, hydroxy urea and rapamycin (sirolimus or Rapamune) or derivatives thereof.

The compounds of the invention may also be prepared as salts which are pharmaceutically acceptable, but it will be appreciated that non-pharmaceutically acceptable salts also fall within the scope of the present disclosure at least to the extent that such salts are useful as intermediates in the preparation of pharmaceutically acceptable salts. Examples of pharmaceutically acceptable salts include, but are not limited to, sulfates, phosphates, mesylates, bismesylates, tosylates, lactates, tartrates, malates, bis-acetates, citrates, bishydrochloride salts, salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety. The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin. In some embodiments, the salt is a sulfate, phosphate, mesylate, bismesylate, tosylate, lactate, tartrate, malate, bis-acetate, citrate, or bishydrochloride salt.

In some embodiments, the compounds of the present disclosure are administered in a therapeutically effective amount. Such an administration imparts that a compound of Structure 1 will elicit a response associated with, e.g., cells, tissues, fluids, of a subject being sought by the clinician. In the treatment or prevention of conditions mediated by, or associated with, kinase inhibition, e.g., RTK inhibition, an appropriate dosage level is administered. In some embodiments, from about 0.01 to 500 mg/kg of subject body weight per day is administered in single or multiple doses. In accord, dosage levels are from about 0.1 to about 250 mg/kg per day in some embodiments, while in other embodiments from about 0.5 to about 100 mg/kg per day is administered to the subject. Suitable dosage levels include, for example, from about 0.01 to 250 mg/kg per day, from about 0.05 to 100 mg/kg per day, or from about 0.1 to 50 mg/kg per day. Within this range, in some embodiments, the dosage is from about 0.05 to 0.5, 0.5 to 5 or 5 to 50 mg/kg per day. For oral administration, the compositions are provided in the form of tablets containing 1.0 to 1000 mg of the active ingredient, including, but not limited to, 1, 5, 10, 15, 20, 25, 50, 75, 100, 150, 200, 250, 300, 400, 500, 600, 750, 800, 900, and 1000 mg of the active ingredient. The dosage may be selected, for example, to any dose within any of these ranges, for therapeutic efficacy and/or symptomatic adjustment of the dosage to the subject being treated. In some embodiments, the compounds of the present disclosure are administered by inhalation as described in, e.g., U.S. Pat. No. 8,257,741, U.S. Pat. No. 8,263,128, WO 2010/132827, WO 2010/102066, WO 2012/040502, WO 2012/031 129, and/or WO 2010/102065, from 1 to 20, 1 to 15, 1 to 10, 1 to 5, 1 to 4, or 1 to 3 times daily, or once or twice per day. In some embodiments, the compounds of the present disclosure are administered from 1 to 5 times daily.

In some embodiments, the unit dose is sufficient to provide one or more of: (a) a $C_{max}$ of about 1 to 5000 ng/mL of the compound In a subject's plasma or a $C_{max}$ of about 1 to 5000 ng/mL of the compound In the subject's blood when it is administered to the subject; and (b) about 1 to 5000 ng/mL of the compound in a subject's plasma 24 h after administration or about 1 to 5000 ng/mL of the compound in the subject's blood 24 h after administration to the subject.

The therapeutically effective amount of a compound of Structure 1, the tautomer of the compound, enantiomer, isomer or stereoisomer of the compound, a pharmaceutically acceptable salt of the compound, tautomer, enantiomer, isomer or stereoisomer of the compound, or any mixtures thereof, is not associated with adverse side effects, in some embodiments. Such adverse side effects include, but are not limited to, decreased lung function, increased or decreased systemic blood pressure, immunocompromised, bone marrow suppression, anemia, hypoxia, in the subject compared to the subject prior to the administering.

Prevention and Treatment of Disease

In one aspect, the present disclosure provides a compound of Structure 1, a tautomer of the compound, enantiomer, isomer or stereoisomer of the compound, a pharmaceutically acceptable salt of the compound, tautomer, enantiomer, isomer or stereoisomer of the compound, or any mixtures thereof for treating one or more diseases, where Structure 1 is described herein.

The present disclosure accordingly provides compounds, compositions, and methods of inhibiting kinases, e.g., tyrosine kinases, and methods of treating biological conditions mediated by, or associated with, such kinases. For example, the present disclosure provides methods of inhibiting one or more kinases, such as, e.g., cell division cycle 2 kinase (Cdc2 kinase), c-Kit, c-ABL, p60src, AKT, VEGFR3, PDGFRα, PDGFRβ, PDGFR-αα, PDGFR-ββ, PDGFR-αβ, FGFR3, FLT-3, FY oncogene kinase related to SRC, FGR, YES (Fyn), lymphocyte-specific protein tyrosine kinase (Lck), tyrosine kinase with Ig and EGF homology domains (Tie-2), FMS (CSF-IR), KDR, EphA2, EphA3, EphA8, FLT1, FLT4, HCK, PTK5, RET, SYK, DDR1, DDR2, glycogen synthase kinase 3 (GSK-3), cyclin dependent kinase 2 (Cdk2), cyclin dependent kinase 4 (Cdk4), MEK1, NEK-2, CHK2, CKIε, Raf, checkpoint kinase 1 (CHK1), ribosomal S6 kinase 2 (Rsk2), and PAR-1. In particular, compounds, compositions, and methods of inhibiting tyrosine kinases, such as, e.g., cell division cycle 2 kinase (Cdc2 kinase), ERK1/2, STAT3, AKT, c-Kit, c-ABL, p60src, VEGFR3, PDGFRα, PDGFRβ, PDGFR-αα, PDGFR-ββ, PDGFR-αβ, FGFR3, FLT-3, FYN oncogene kinase related to SRC, FGR, YES (Fyn), lymphocyte-specific protein tyrosine kinase (Lck), tyrosine kinase with Ig and EGF homology domains (Tie-2), FMS (CSF-IR), KDR, EphA2, EphA3, EphA8, FLT1, FLT4, HCK, PTK5, RET, SYK, DDR1, and DDR2. In some embodiments, the tyrosine kinase is a receptor tyrosine kinase (RTK), such as, e.g., PDGFR, PDGFR-αα, PDGFR-ββ, PDGFR-αβ, or c-Kit, or combinations thereof, are provided.

The present disclosure also provides compounds, compositions, and methods of treating biological conditions mediated by, or associated with, kinases, e.g., tyrosine kinases, including Cdc2 kinase, c-Kit, AKT, c-ABL, ERK1/2, STAT3, p60src, VEGFR3, PDGFRα, PDGFRβ, FGFR3, PDGFR-αα, PDGFR-ββ, PDGFR-αβ, FLT-3, Fyn, Lck, Tie-2, GSK-3, Cdk2, Cdk4, MEK1, NEK-2, CHK2, CKIε, Raf, CHK1, Rsk2, FMS (CSF-IR), KDR, EphA2, EphA3, EphA8, FLT1, FLT4, HCK, PTK5, RET, SYK, DDR1, DDR2 and PAR-1. In particular, the present disclosure provides compounds, compositions, and methods of treating biological conditions mediated by, or associated with, tyrosine kinases, including, but not limited to, Cdc2 kinase, AKT, c-Kit, c-ABL, p60src, VEGFR3, PDGFRα, PDGFRβ, PDGFR-αα, PDGFR-βfβ, PDGFR-αβ, FGFR3, FLT-3, Fyn, Lck, Tie-2, FMS (CSF-IR), KDR, EphA2, EphA3, EphA8, FLT1, FLT4, HCK, PTK5, RET, SYK, DDR1, and DDR2. In some embodiments, the disease or condition mediated by, or associated with, one or more kinases is mediated by a RTK, such as, e.g., PDGFR, PDGFR-αα, PDGFR-ββ, PDGFR-αβ, or c-Kit, or combinations thereof.

The disease or condition mediated by, or associated with, one or more kinases of the present disclosure, includes, but is not limited to, PAH, primary PAH, idiopathic PAH, heritable PAH, refractory PAH, BMPR2, ALK1, endoglin associated with hereditary hemorrhagic telangiectasia, endoglin not associated with hereditary hemorrhagic telangiectasia, drug-induced PAH, and toxin-induced PAH, PAH associated with or secondary to one or more of systemic sclerosis, mixed connective tissue disease, cancer, refractory cancer, metastatic cancer, neoplasia, hypoplasia, hyperplasia, dysplasia, metaplasia, prosoplasia, desmoplasia, angiogenic disease, pulmonary function disorders, cardiovascular function disorders, HIV infection, hepatitis, portal hypertension, pulmonary hypertension, congenital heart disease, hypoxia, chronic hemolytic anemia, newborn persistent pulmonary hypertension, pulmonary veno-occlusive disease (PVOD), pulmonary capillary hemangiomatosis (PCH), left heart disease pulmonary hypertension, systolic dysfunction, diastolic dysfunction, valvular disease, lung disease, interstitial lung disease, pulmonary fibrosis, schistosomiasis, chronic obstructive pulmonary disease (COPD), sleep-disordered breathing, alveolar hypoventilation disorders, chronic exposure to high altitude, developmental abnormalities, chronic thromboembolic pulmonary hypertension (CTEPH), pulmonary hypertension with unclear multifactorial mechanisms, hematologic disorders, myeloproliferative disorders, splenectomy, systemic disorders, sarcoidosis, pulmonary Langerhans cell histiocytosis, lymphangioleimoyomatosis, neurofibromatosis, vasculitis, metabolic disorders, glycogen storage disease, Gaucher disease, thyroid disorders, tumoral obstruction, fibrosing mediastinitis, and chronic renal failure on dialysis; and diseases such as pulmonary hypertension, congenital heart disease, hypoxia, chronic hemolytic anemia, newborn persistent pulmonary hypertension, pulmonary veno-occlusive disease (PVOD), pulmonary capillary hemangiomatosis (PCH), left heart disease pulmonary hypertension, systolic dysfunction, diastolic dysfunction, valvular disease, lung disease, interstitial lung disease, pulmonary fibrosis, schistosomiasis, chronic obstructive pulmonary disease (COPD), sleep-disordered breathing, alveolar hypoventilation disorders, chronic exposure to high altitude, developmental abnormalities, chronic thromboembolic pulmonary hypertension (CTEPH), pulmonary hypertension with unclear multifactorial mechanisms, hematologic disorders, myeloproliferative disorders, splenectomy, systemic disorders, sarcoidosis, pulmonary Langerhans cell histiocytosis, lymphangioleimoyomatosis, neurofibromatosis, vasculitis, metabolic disorders, glycogen storage disease, Gaucher disease, thyroid disorders, tumoral obstruction, fibrosing mediastinitis, immunological and inflammatory diseases, hyperproliferative diseases, renal and kidney diseases, bone remodeling diseases, metabolic diseases, vascular diseases, and chronic renal failure on dialysis.

In one aspect, the present disclosure provides a method of treating pulmonary arterial hypertension (PAH) in a subject or a biological condition associated with PAH in a subject by administering to the subject a therapeutically effective amount of a compound of Structure 1, a tautomer of the compound, a pharmaceutically acceptable salt of the compound, a pharmaceutically acceptable salt of the tautomer, or a mixture thereof, wherein a compound of Structure 1 is described herein. In some embodiments, the disease or condition mediated by, or associated with, one or more kinases of the present disclosure is selected form the group consisting of PAH, primary PAH, idiopathic PAH, heritable PAH, refractory PAH, drug-induced PAH, toxin-induced PAH, and PAH with secondary diseases.

Pulmonary arterial hypertension (PAH) is a life-threatening disease characterized by a marked and sustained elevation of pulmonary artery pressure. The disease results in right ventricular (RV) failure and death. Current therapeutic approaches for the treatment of chronic pulmonary arterial hypertension mainly provide symptomatic relief, as well as some improvement of prognosis. Although postulated for all treatments, evidence for direct antiproliferative effects of most approaches is missing. In addition, the use of most of the currently applied agents is hampered by either undesired side effects or inconvenient drug administration routes. Pathological changes of hypertensive pulmonary arteries include endothelial injury, proliferation and hyper-contraction of vascular smooth muscle cells (SMCs), and fibroblast proliferation. PAH patient status, moreover, can be assessed in accordance with the World Health Organization (WHO) classification (modified after the NY Association Functional Classification) as known in the art.

In some embodiments, the compounds of Structure 1 treat or prevent PAH in patients who failed prior therapy, especially after receiving at least one prostanoid, endothelin antagonist or PDE V inhibitor. In other embodiments, the compounds treat or prevent PAH in patients who are more severely affected, in particular in patients with Class II to Class IV functional status, or more severely Class III or IV functional status. In further embodiments, the compounds treat or prevent PAH in patients who are harboring BMPR2 mutations.

The present disclosure provides methods of preventing or treating subjects afflicted with idiopathic or primary pulmonary hypertension, familial hypertension, pulmonary hypertension secondary to, but not limited to, connective tissue disease, congenital heart defects (shunts), pulmonary fibrosis, portal hypertension, HIV infection, sickle cell disease, drugs and toxins, e.g., anorexigens, cocaine, chronic hypoxia, chronic pulmonary obstructive disease, sleep apnea, and schistosomiasis, pulmonary hypertension associated with significant venous or capillary involvement (pulmonary veno-occlusive disease, pulmonary capillary hemangiomatosis), secondary pulmonary hypertension that is out of proportion to the degree of left ventricular dysfunction, and/or persistent pulmonary hypertension in newborn babies, especially in subjects that previously failed prior PAH therapy.

In one aspect, the present disclosure provides a compound of Structure 1, a tautomer of the compound, enantiomer, isomer or stereoisomer of the compound, a pharmaceutically acceptable salt of the compound, tautomer, enantiomer, isomer or stereoisomer of the compound, or any mixtures thereof for treating one or more diseases associated with hyperproliferation, neoplasia, hypoplasia, hyperplasia, dysplasia, metaplasia, prosoplasia, desmoplasia, angiogenesis, inflammation, pulmonary function, and cardiovascular function, where a compound of Structure 1 is described herein.

Hyperproliferative, immunological and inflammatory, metabolic, and vascular diseases, are known in the art, and such diseases, as described in U.S. Provisional Patent No. 61/751,217, which is hereby incorporated by reference in its entirety, are therapeutic targets for the compounds and agents described herein.

Another aspect of the present disclosure related to a method of preventing or reducing elevated pulmonary pressure in a subject, by administering to the subject a therapeutically effective amount of a compound of Structure 1, a tautomer of the compound, a pharmaceutically acceptable salt of the compound, a pharmaceutically acceptable salt of the tautomer, or a mixture thereof, where a compound of Structure 1 is described herein. See, e.g., Summary. In some embodiments, the compounds of Structure 1 treat or prevent a biological condition associated with PAH, such as, e.g., abnormal: right ventricular systolic pressure (RVSP); pulmonary pressure; cardiac output; right ventricular (RV) hypertrophy; and PA hypertrophy.

In some embodiments, the compounds of Structure 1 reduce pulmonary pressure associated with an increase in one or more of right ventricular (RV) function, pulmonary artery (PA) systolic pressure, and/or cardiac output in the subject compared to the subject prior to the administering. In some embodiments, the reduction in pulmonary pressure is associated with a decrease in one or more of RV hypertrophy, PA hypertrophy, RVSP, sustained PA pressure, and the risk of stroke in the subject compared to the subject prior to the administering. In some embodiments, the decrease is at least a 5, 10, 15, 20, 25, 30, 35, 40, 45, 50, 55, 60, 65, 70, 75, 80, 85, 90, or 95% decrease. In some embodiments, the decrease is at least a 40% decrease.

A reduction in pulmonary pressure, in some embodiments, is not associated with decreased lung function and/or increased systemic blood pressure in the subject compared to the subject prior to the administering. Methods for measuring lung function and blood pressure are known in the art. In one aspect, the present disclosure provides a method of treating pulmonary arterial hypertension (PAH) in a subject, comprising: modulating the phosphorylation-state ("PS") of one or more downstream targets of platelet derived growth factor receptor-alpha or platelet derived growth factor receptor-beta or both, wherein the downstream target is any substrate phosphorylated as a result of the PDGFR-α and/or the PDGFR-β activation, by administering to the subject a compound of Structure 1, a tautomer, enantiomer, isomer or stereoisomer of the compound, a pharmaceutically acceptable salt of the compound, tautomer, enantiomer, isomer or stereoisomer of the compound, or any mixtures thereof, wherein the downstream target is selected from the group consisting of AKT, PDGFR, STAT3, ERK1 and ERK2, or any other downstream target of the PDGFR-α and/or the PDGFR-β, and wherein the compound of Structure 1 is described herein. Phosphorylation state profiles for proteins, kinases/receptors, can be ascertain using techniques known in the art, such as, for example, Z-lyte kinase assays, Invitrogen Select Screen®, and other kinases assay's know in the art.

In suitable embodiments, the modulation of the kinase receptor activity is an inhibition of the kinase receptor activity. PDGFR, i.e., PDGFR-α, PDGFR-β, PDGFR-αα, PDGFR-ββ, and PDGFR-αβ, and/or c-Kit are examples of RTKs that are inhibited in some embodiments of the present invention. In some embodiments, the inhibition is at least a 0.001, 0.01, 0.1, 1, 5, 10, 15, 20, 25, 30, 35, 40, 45, 50, 55, 60, 65, 70, 75, 80, 85, 90, or 95% inhibition. In some embodiments, the PSR modulation is a modulation of one or more of AKT, STAT3, ERK1, ERK2, PDGF, and PDGFR i.e., PDGFR-αα, PDGFR-ββ, and PDGFR-β. In some embodiments, the modulation of PS is a decrease of phosphorylated STAT3 to total STAT3 in the subject compared to the PS in the subject prior to the administering. In some embodiments, the decrease is at least a 0.001, 0.01, 0.1, 1, 5, 10, 15, 20, 25, 30, 35, 40, 45, 50, 55, 60, 65, 70, 75, 80, 85, 90, or 95% decrease. In some embodiments, the modulation of PS is a decrease of diphosphorylated ERK1 to total ERK1 in the subject compared to the PS in the subject prior to the administering. In some embodiments, the decrease is at least a 0.001, 0.01, 0.1, 1, 5, 10, 15, 20, 25, 30, 35, 40, 45, 50, 55, 60, 65, 70, 75, 80, 85, 90, or 95% decrease. In other embodiments, the modulation of PS is a decrease of diphosphorylated ERK2 to total ERK2 in the subject compared to the PS in the subject prior to the administering. In some embodiments, the decrease is at least a 0.001, 0.01, 0.1, 1, 10, 50, 60, 70, 80, 85, 90, or 95% decrease.

In some embodiments, the modulation of PS is a decrease of monophosphorylated ERK1 to total ERK1 in the subject compared to the PS in the subject prior to the administering. In some embodiments, the decrease is at least a 0.001, 0.01, 0.1, 1, 5, 10, 15, 20, 25, 30, 35, 40, 45, 50, 55, 60, 65, 70, 75, 80, 85, 90, or 95% decrease. In some embodiments, the modulation of PS is a decrease of phosphorylated PDGFR to total PDGFR in the subject compared to the PS in the subject prior to the administering. In some embodiments, the decrease is at least a 0.001, 0.01, 0.1, 1, 5, 10, 15, 20, 25, 30, 35, 40, 45, 50, 55, 60, 65, 70, 75, 80, 85, 90, or 95% decrease. In some embodiments, the modulation of PS is a decrease of phosphorylated AKT to total AKT in the subject compared to the PS in the subject prior to the administering. In some embodiments, the decrease is at least a 0.001, 0.01, 0.1, 1, 5, 10, 15, 20, 25, 30, 35, 40, 45, 50, 55, 60, 65, 70, 75, 80, 85, 90, or 95% decrease.

EXAMPLES

The present invention is further illustrated by the following examples, which should not be construed as limiting in any way. The following is a description of the materials and methods used throughout the examples, which illustrates that RTK signaling pathways are activated in human disease conditions, e.g., PAH and in animal models of the disease.

Materials.

PK10453, (S)—N-(3-(1-((6-(4-hydroxy-3-methoxyphenyl)pyrazin-2yl)amino)ethyl)phenyl)-5-methylnicotinamide, i.e., Structure 2, was synthesized by Organix, Inc. (Woburn, Mass.). Human PA smooth muscle cells and cell culture media were obtained from Cell Applications, Inc. PDGFBB, para-toluene sulfonic acid, ammonium hydroxide, and IR780 were obtained from Sigma Aldrich (St. Louis, Mo.). Imatinib mesylate was obtained from LC Laboratories (Woburn, Mass.). Human fetal lung fibroblasts (HLFs) were obtained from Cell Applications, Inc., San Diego. DMEM medium was obtained from Mediatech (Manassas, Va.). PDGFAA, PDGFBB, and Glutamax were obtained from Life Technologies (Grand Island, N.Y.). Para-toluene sulfonic acid, ammonium hydroxide, IR780 and monocrotaline (C2401 Lot 031M1921V and LotSLBB7802V) were obtained from Sigma Aldrich (St. Louis, Mo.). Anti-phospho-AKT(Ser 473), anti-phospho-AKT (Thr308), pan-AKT (CST2920 mouse mAB, and CST2965 rabbit mAb), anti-phospho-ERK1/2, anti phospho-STAT3, and total STAT3 antibodies were obtained from Cell Signaling Technologies, (Waltham, Mass.). Anti-total ERK1/2 antibody was obtained from Protein Simple (CA). Anti von-Willebrand Factor, actin, phospho-PDGFRα (Y754), and PDGFBB antibodies were obtained from AbCam (Cambridge, Mass.). Antibodies against PDGFAA (sc-128), PDGFR-alpha (sc-338), PDGFR-beta (sc-432) and p-PDGFR-beta (Tyr 1021) (sc-12909) were obtained from Santa Cruz Biotechnology (CA). 680LT goat anti-mouse IgG, IRDye 800 W goat anti-rabbit IgG, and Odyssey blocking buffer were obtained from Licor (Lincoln, Nebr.).

In Vitro Kinase Assay.

A Z-lyte kinase assay was performed to determine the inhibition of PDGFRalpha and PDGFRbeta mediated phosphorylation by PK10453 (Structure 2). Ten point titration curves were modeled to calculate the $IC_{50}$ (Invitrogen Select Screen®).

PASMC Proliferation Assay.

Human pulmonary artery smooth muscle cells (PASMC) were obtained from Cell Applications (San Diego, Calif.) and grown to 50% confluence in a 96 well format. The cells were switched to serum free media 24 hours prior to stimulation with PDGFBB 50 ng/ml and varying concentrations of PK10453 (Structure 2). After 24 hours of treatment, a Cyquant NF Cell proliferation assay was performed (Invitrogen®), and the fluorescent signal was measured with a Cytofluor Plate reader. Data is based on an average of 8 replicates at each concentration.

In Cell Western (ICW).

To compare the inhibitory profiles of PK10453 (Structure 2) and imatinib for PDGFBB and PDGFAA stimulated AKT phosphorylation, ICWs were performed, with modifications, according to the method of Chen et al., "A cell-based immunocytochemical assay for monitoring kinase signaling pathways and drug efficacy." *Analytical Biochemistry*; Vol. 338: 136-42 (2005). HLFs were maintained in subculture at no more than 6 passages in DMEM with 5% FBS and 4 mM Glutamax at 37° C., 5% $CO_2$. HLFs were plated and grown to 70-80% confluence in 96 well plates then serum-starved for 48 hours. Cells were treated with drug (PK10453 or imatinib) at indicated concentrations for 30 min then exposed to 10 ng/ml PDGF AA or BB for 7.5 min. Cells were fixed in 3.7% formaldehyde, washed with 0.1% Triton X-100, and treated with Odyssey Blocking Buffer for 90 min. Proteins were incubated overnight 1:100 diluted rabbit mAb to phosphorylated AKT (Ser 473 or Thr 308) and 1:100 mouse mAb to total Akt-pan-4040D. Antibodies were detected using IRDye 680LT goat anti-mouse IgG and IRDyc 800 W goat α-rabbit IgG conjugated antibodies. After washing, the signal was quantified using an Odyssey Infrared Imaging System (LI-COR). Phosphoprotein signal (800 nm) was normalized to total protein signal (700 nm) acquired from each well and experimental duplicates on same plate were averaged and reported.

Animals.

Male Sprague Dawley rats (weight 320-330 grams; Taconic Inc.) were used for this study. Animals were housed in standard rat cages with a 12 h light/dark cycle, and standard rat chow and water were provided ad libitum. Animals were cared for and used in accordance with NIH guidelines. All animal protocols were approved by the Bassett Medical Center and Pulmokine IACUC.

Formulation and Aerosol Delivery.

PK10453 (Structure 2) was dissolved at a concentration of 20 mg/ml in 1M tosylic acid. Nebulization was performed with a PARI Nebulizer with an air pressure of 12.5 psi. The aerosol droplets were neutralized by ammonia vapor that was passed into the aerosol air stream. The particles were then dried by flowing through an annular ring of silica bead cartridges prior to reaching the exposure chamber. The 6-port exposure chamber was a nose-only exposure system custom designed and built by Powerscope Inc. (Minneapolis, Minn.). The vacuum flow rate at each port was separately controlled by a flow meter. The aerosol particle size was measured at the exit port of the drying column with an Anderson (Mark II) cascade impactor. The mass median aerodynamic diameter (MMAD) was 2 µm and the associated geometric standard deviation (GSD) was 1.6. Imatinib mesylate was dissolved in water at 20 mg/ml and delivered by a PART nebulizer then dried by passage through an annular ring of silica bead cartridges prior to inhalation.

Estimation of Inhaled Dose.

Filters exposed to PK10453 (Structure 2) for either 4 or 8 min (n=6 each group) via the Powerscope exposure chamber were placed in amber glass vials. Twelve milliliters of 1:3 (v/v) methanokacetonitrile were added to each vial containing a filter for approximately 1 hr, with periodic mixing, followed by sonication for 60 seconds. An aliquot was then diluted 100-fold by adding 10 μL, of unknown filter extract to 990 μL, of 1:3 (v/v) methanokacetonitrile. Samples were vortex mixed for 30 seconds, and then a 100 μL, diluted aliquot was combined with 100 μL of 172 ng/mL of a nonchemically related internal standard (PK18855) in 1:1 methanokwater, vortex mixed and transferred to autosampler vials for LC-MS/MS analysis. Filter extracts were compared against a calibration curve prepared in 100% methanol (PharmOptima®, Inc.). The aerosol concentration of PK10453 (Structure 2) in μg/liter of air was calculated based on the average total μg of PK10453 (Structure 2) on the filters for the 4 and 8 min exposure times, and the flow rate past each filter (0.8 L/min). The inhaled dose was calculated with the average concentration of PK10453/$cm^2$ filter paper (average of 4 and 8 min exposures), the average min ventilation measured by plethysmography (0.15 L/min), and an estimated deposition fraction of 0.1. The imatinib 8 min dose was based on gravimetric analysis.

Imaging.

The spatial distribution of inhaled PK10453 (Structure 2) in the lung was evaluated by fluorescent imaging. A near IR fluorescent tracer, IR-780, was added to the drug solution in the nebulizer to ensure dried aerosol particles contained both the drug and IR tracer. After a two min exposure, animals were placed under general anesthesia underwent intubation via tracheostomy, and the lungs were excised. OCT/PBS was infused via the pulmonary artery, the lung insufflated with air, and the lungs frozen in the vapor phase of liquid nitrogen. Serial approximate 2 mm sections of lung were imaged on a Licor Odyssey Imager.

Pharmacokinetic Studies.

PK10453 (Structure 2) was administered intravenously or by inhalation to animals, which were then euthanized at time 0, 10, 20, and 60 min (n=3 each time point). Blood samples were taken by cardiac puncture, and the lungs excised. The lungs were homogenized and PK10453 (Structure 2) extracted with a 1:3 mixture of acetonitrile:methanol. Similarly, plasma was extracted with a 1:3 mixture of acetonitrile:methanol. Drug was assayed by LC MS/MS (PharmOptima Inc., Portage Mich.). First order exponential curves were fit to the data with Excel. AUC was determined with the trapezoidal method of integration.

Efficacy Study in the Rat MCT Model—PK10453 (Structure 2) Dose Response Study in the Rat MCT Model.

Male Sprague Dawley rats received MCT 60 mg/kg IPMCT, and after 3 weeks, PK10453 (Structure 2) or vehicle control were administered by inhalation. Four groups were studied: vehicle control (4 min exposure) and three treatment groups of PK10453 (Structure 2) with exposure times 2 min (D2), 4 min (D4), or 8 min (D8) three times a day. These regimens were administered for two weeks. The vehicle consisted of aerosolized 1M tosylic acid neutralized with ammonia vapor as described above. The pH of a solution prepared by dissolving captured aerosol particles in water was measured for every dose and was consistently in the range of 5.5-6.0. At the end of the study, the RV systolic pressure was measured, and the heart chambers dissected and weighed.

Efficacy Study in the Rat MCT Model—PK10453 (Structure 2) Vs. Imatinib in the Rat MCT Model.

Male Sprague Dawley rats were given MCT 60 mg/kg IP. Three weeks later vehicle (1M tosylic acid), PK10453 (Structure 2 at 20 mg/ml free base in 1 M tosylic acid), or imatinib mesylate (20 mg/ml in nebulizer solution) were administered to designated groups for 8 min inhalation exposures, three time a day, for two weeks. At the end of the study RVSP pressure was measured; lung and heart fixed in formalin. For measurement of RVSP animals were sedated with isoflurane, intubated via a tracheostomy, and ventilated with a TOPOVENT pressure regulated ventilator (peak inspiratory pressure 18 cm $H_2O$, PEEP 5 cm). After sternotomy, a Scisense high fidelity catheter inserted via the RV apex.

Efficacy Study in the Rat MCT+PN Model.

Pneumonectomy and implantation of a TRM53P telemetry monitor in the pulmonary artery (Telemetry Research, New Zealand and ADInstruments, Colorado) was carried out in rats. Two weeks after MCT, PK10453 (Structure 2) was administered three times daily for 1 week. Dosing was begun 2 weeks after MCT rather than 3 weeks, because in this more aggressive model the animals developed PAH more quickly and developed distress sooner than in MCT only treated animals (data not shown). The two groups underwent 4 min exposures of either the vehicle control or PK10453 (Structure 2). Sampling of PA pressure was performed 5 min before each morning dose in ambulatory animals in room air (estimated atmospheric pressure 716 mm Hg based on elevation of animal facility). In protocol 4 (imatinib vs. vehicle), the animals received DSI PAC40 transmitters followed by monocrotaline 50 mg/kg IP (Lot SLBB7802V). A lower dose of MCT was used for this study, because attempts to use 60 mg/kg of this lot of MCT resulted in the need for early euthanasia in a high proportion of animals due to weight loss and tachypnea. Two weeks after MCT IP injection, vehicle (mesylate 3 mg/ml) or imatinib mesylate 20 mg/ml in nebulizer solution) was administered for 8 min exposures three times a day for 9 days. Telemetry data was obtained for 10 min daily before each morning dose for this protocol.

Measurement of PV Loops.

In a separate cohort of animals, the MCT+PN model was developed as described above, and PK10453 (Structure 2) was then administered for 4 or 8 min three times a day to the drug treated group. The vehicle control group underwent 4 min exposures three times a day. Pressure Volume (PV) loops were obtained with an admittance system (Scisense, Inc.) after 14 days of treatment, while rats were under general anesthesia with isoflurane and 100% $FiO_2$. Also, or in the alternative, RV pressures were obtained in each group after 14 days of treatment. In a subset of each group, pressure Volume (PV) loops were obtained with an admittance system (high fidelity catheter FTE1918B, Scisense, Inc.) after 14 days of treatment. After induction of general anesthesia and intubation via tracheostomy, the rats were placed on a pressure controlled ventilator (TOPOVENT). General anesthesia consisted of isoflurane and 100% $F10_2$ with peak inspiratory pressure set at 18 cm, and PEEP 5 cm $H_2O$. A left thoracotomy was performed with admittance catheter in the RV via the RV outflow tract.

Systemic Blood Pressure Study.

The effect of PK10453 (Structure 2) on systemic BP was studied in ambulatory MCT treated rats with DSI PAC40 transmitters implanted in the descending aorta. Three weeks after administration of MCT 60 mg/kg IP, animals inhaled PK10453 (Structure 2) or vehicle 3×/d with 4 min exposure for 7 days. Blood pressure was recorded before each morning dose.

Plethysmography.

Plethysmography was performed with an EMKA dual chamber plethysmograph and IOX software. Parameters measured included breathing frequency, tidal volume, minute ventilation, peak inspiratory and expiratory flow, and airway resistance (SRaw). Animals were acclimatized to the plethysmograph for three days prior to first data acquisition. Measurements were made prior to the first dose of drug and at the end of the study.

Histology and Morphometric Analysis.

At the end of the study, the heart and lungs were removed from ventilated animals under general anesthesia. Heparinized saline was infused under pressure through the main pulmonary artery. The right upper lobe was immediately tied off and placed in liquid nitrogen for Western blot and NanoPro 100 assay analysis. The heart was removed, and the RV free wall, interventricular septum and LV free wall dissected and weighed. Buffered formalin (10%) was infused under pressure both through the pulmonary artery and the trachea. Morphometric analysis was performed on H&E stained formalin fixed tissue sectioned at 8 The media area and lumen area of pulmonary arterioles were measured with Image J software by a technician blinded to treatment group. Measurements were made on 20 pulmonary arterioles per section. The ratio of the lumen area to the total media area was determined. This ratio normalizes the variation in total pulmonary arteriole area. In addition, occlusive analysis was performed in the monocrotaline plus pneumonectomy study (specifically efficacy study 5) according to the method of Homma et al., "Involvement of RhoA/Rho kinase signaling in protection against monocrotaline-induced pulmonary hypertension in pneumonectomized rats by dehydroepiandrosterone." *Am J Physiol Lung Cell Mol Physiol*. Vol. 295:L71-8 (2008). Briefly, pre-capillary arterioles were assigned grade 0 for no evidence of neointimal lesions, grade 1 for less than 50% luminal occlusion, and grade 2 for greater than 50% occlusion. Masson Trichrome stains were performed on lung sections from the MCT+PN model.

NanoPro Immunoassay.

Relative differences in phosphorylated ERK1/2 and STAT isoforms were measured with a anoProlOO® immunoassay system (Protein Simple/Cell Biosciences, CA). See Fan et al., "Nanofluidic proteomic assay for serial analysis of oncoprotein activation in clinical specimens." *Nat Med* 15:566-571 (2009).

Immunohistochemistry.

Antigen retrieval was performed with citrate buffer (pH 6.0) or Tris-EDTA buffer (pH 9.0). Immunohistochemistry was performed for the following targets: CD20 (a B cell marker), CD3 (a T cell marker), von Willebrand Factor (vWF), total STAT3, phosphoSTAT3 (Tyr705), total PDGFR-alpha, total PDGFR-beta, and phosphoPDGFR-beta. Competing peptides were available for PDGFR-alpha and phospho-PDGFR-beta. Signal detection was performed with an EXPOSE HRP/DAB kit (Abcam®).

Statistical Analysis.

Data are presented as mean±SEM unless otherwise noted. The General Linear Model with the Bonferroni correction for multiple group comparisons was used (SPSS 14.0). Significance was set at the p=0.05 level.

Example 1—Characterization of PK10453 (Structure 2)

Figure 1:
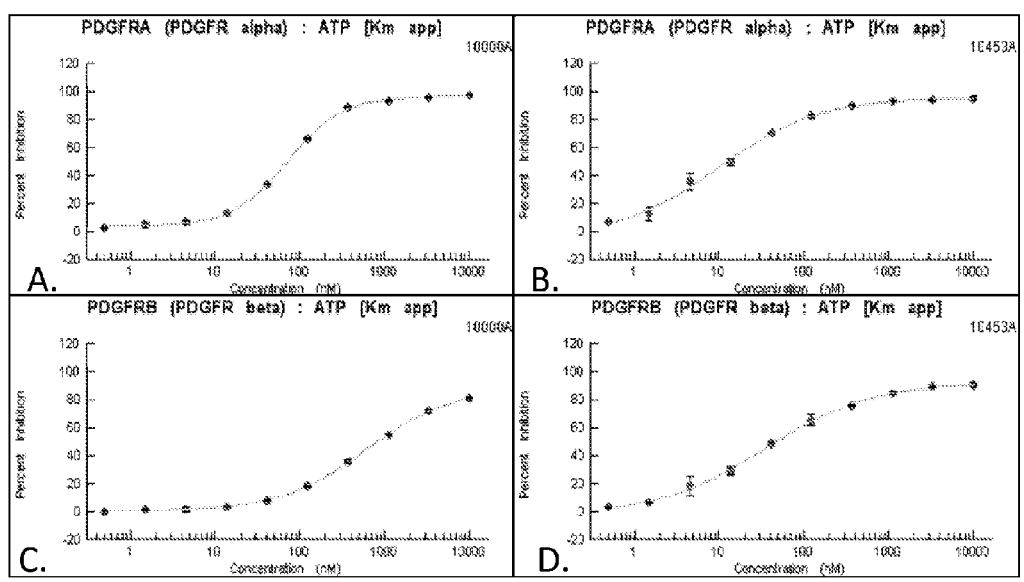
FIG. 1 shows a graph depicting IC$_{50}$ concentrations for Imatinib and PK10453 (Structure 2).
Figure 2:
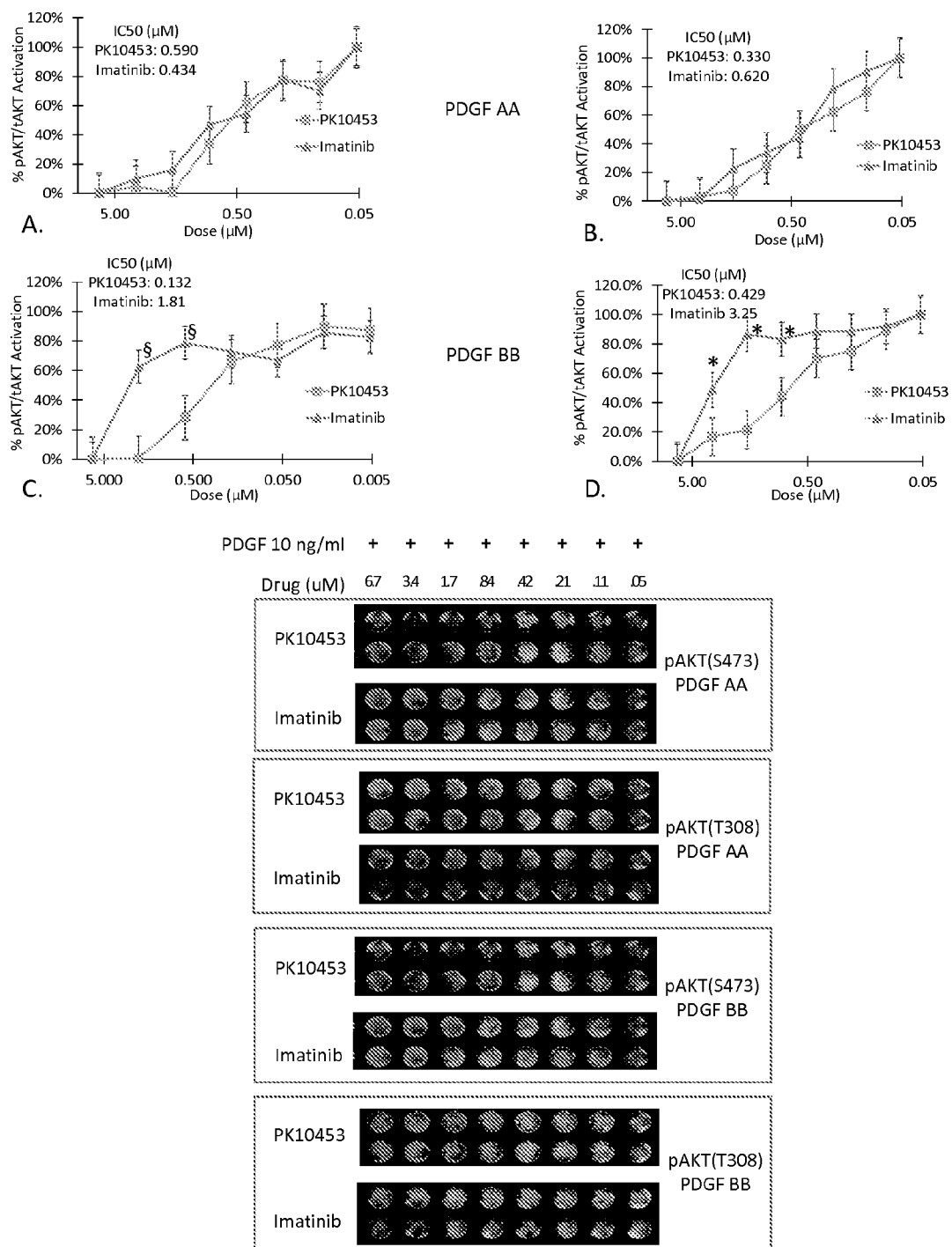
FIG. 2 shows graphs and images of In Cell Western (ICW) assays demonstrating the lower IC$_{50}$ of PK10453 (Structure 2) against PDGFBB stimulated phosphorylation of AKT at Ser473 and Thr308 compared to Imatinib in human fetal lung fibroblasts.

An in vitro kinase assay demonstrated the $IC_{50}$ for PK10453 at ATP $K_m$ was 35 nM for PDGFR-α and 10.1 nM for the PDGFR-β. For imatinib the $IC_{50}$ at ATP $K_m$ was 71 nM for PDGFR-α and 607 nM for PDGFR-beta. See FIG. 1. The $IC_{50}$ of PK10453 for PDGFBB stimulated AKT phosphorylation at Ser473 was 0.13 μM compared to 1.8 μM for imatinib (p<0.01), as shown in the ICW illustrated in FIG. 2. The $IC_{50}$ of PK10453 for PDGFBB stimulated AKT phosphorylation at Thr308 was 0.43 μM vs. 3.25 μM for imatinib (p<0.001). The $IC_{50}$ concentrations of PK10453 and imatinib for PDGFAA stimulated phosphorylation of AKT were not significantly different.

Estimated Inhaled Dose—PK10453 (Structure 2) and Imatinib.

The average concentration of PK10453 was 62.4±3.3 μg/cm² filter paper for the 4 min exposure, and 137±7.0 μg/cm² for the 8 min exposure, which resulted in an aerosol concentration of 91.65 μg/L air for the 4 min exposure and 100.6 μg/L air for the 8 min exposure. The aerosol concentration of imatinib based on gravimetric analysis was 167 mg/L. The average inhaled dose (8 min), assuming a deposition fraction of 0.1 and rat weight 300 g, was approximately 20 μg/kg for PK10453, and 40 μg/kg for imatinib, as shown in Table 1. The estimated inhaled dose was calculated from the measured concentration of PK10453 (Structure 2) and gravimetric analysis of imatinib in the aerosol, the measured minute ventilation (MV), the estimated deposition fraction of 0.1, and rat weight 300 g.

TABLE 1

| API | Aerosol Conc ug/L | Exposure Min | MV L/min | MV * Exposure time | Total Deposition fraction | Lung deposition fraction | Total Inhaled ug | Total Deposited ug | Lung deposited ug | Lung deposited ug/kg |
|---|---|---|---|---|---|---|---|---|---|---|
| PK10453 | 96.13 | 8.00 | 0.15 | 1.20 | 0.10 | 0.60 | 115.36 | 11.54 | 6.92 | 23.07 |
| Imatinib | 167.4 | 8.00 | 0.15 | 1.20 | 0.10 | 0.60 | 200.88 | 20.09 | 12.05 | 40.18 |

Lung Distribution and Pharmacokinetics of Inhaled PK10453 (Structure 2).

Fluorescent images of the lung sections following inhalation of PK10453 with IR780 tracer are shown in FIG. 3, where the fluorescence intensity is shown to be well distributed throughout the lungs. The network of darker lines arises from the connective tissue and therefore does not represent the airways affected by the disease. The spatial distribution of imatinib was similar (data not shown).

For the pharmacokinetic study, the concentration of PK10453 (Structure 2) in lung when administered by inhalation was compared to the concentration achieved with IV administration. As described in Moren "Aerosols in medicine: principles, diagnosis, and therapy." Amsterdam; New York: Elsevier, xx, 429 (1993) and Phalen et al., "Inhalation exposure methodology." *Environ Health Perspect* 56:23-34 (1984)), it is possible to estimate the pharmacokinetic advantage of inhalation relative to intravenous administration, $R_d$, by comparing the AUC of a plot of the drug concentration as a function of time following respiratory and IV administration:

$$R_d=[(AUC_{lung}/AUC_{plasma})\text{respiratory}]/[(AUC_{lung}/AUC_{plasma})\text{IV}]$$

The pharmacokinetic data was modeled to a first order exponential curve, and the AUC calculated from the curves (see Table 2). FIG. 4 shows the drug level in lung and plasma as a function of time following inhalation or IV administration of PK10453 (Structure 2). The data indicate a 45 fold advantage of inhaled compared to IV administered PK10453 ($R_d$=44.6).

TABLE 2

| Y = AEXP (-bX) | A (ng/g lung) | b (min−1) | R2 |
|---|---|---|---|
| Lung (INH) | 2498 | 0.03 | 0.89 |
| Plasma (INH) | 132.7 | 0.07 | 0.93 |
| Lung (IV) | 440 | 0.06 | 0.96 |
| Plasma (IV) | 1260 | 0.07 | 0.92 |

| | AUC | | |
|---|---|---|---|
| Lung (INH) | 1001.82 | | |
| Plasma (INH) | 65.47 | | |
| Lung (IV) | 211.89 | | |
| Plasma (IV) | 617.25 | | |
| | Rd | | |
| | 44.58 | | |

Example 2—MCT Model Efficacy

RVSP values are shown in FIG. 5A. In the vehicle group (n=6), RVSP was 80.4±2.6 mm Hg. For the treatment groups, D2 (n=6), 51.4±6.5; D4 (n=6), 44.4±3.8; and D8 (n=5), 37.1±4.5 mm Hg (p<0.001). Normal control group RVSP was 28.5±2.6 mm Hg (n=3). In the D4 group, there was a 44% reduction in RVSP, and in the D8 group, there was a 54% reduction in RVSP compared to the vehicle treated group. There was also a significant reduction in the degree of RV hypertrophy as measured by the ratio (RV+IVS)/LV weight. See FIG. 5B. The data are represented by this ratio because the septum is shared by the RV and LV. However, use of the RV/(rVS+LV) ratio also showed similar results.

Moreover, there were 6 animals in the vehicle group but accurate RV end systolic pressures were not obtained due to bleeding in 2 animals. Therefore RV systolic pressure is based on n=4 in the vehicle group and was 57.9±7.6 mm Hg. In the PK10453 (Structure 2) group (n=12) RV end systolic pressure was 36.3±2.6 mm Hg, and in the imatinib group (n=6) was 31.8±1.8 mm Hg (p=0.001 Vehicle vs. PK10453; p=0.002 Vehicle vs. Imatinib, FIG. 5C). End systolic volume was greater in the vehicle group (158±12.6 µL) vs. PK10453 (99.5±10 µl) and imatinib (81±4.3 µL) (p=0.05 vehicle vs. PK10453; p=0.014 vehicle vs. imatinib; p=NS PK10453 vs. imatinib). There were no significant differences between the groups for the following parameters: end diastolic volume, ejection fraction, cardiac output, stroke work. The lumen to media ratio was improved by both PK10453 and imatinib compared to vehicle in the MCT model (Vehicle (V, n=4): 0.55±0.1; PK10453 (D8, n=12): 0.94±0.08; Imatinib (18, n=5): 0.99±0.07; p<0.01 D8 vs. V, p<0.05 18 vs. V, FIG. 5D).

Example 3—Efficacy Studies in the Rat MCT+PN Model

Telemetry Studies.

The results of the telemetry study in the rat MCT+PN model are described. At day 0 prior to start of treatment, the PA systolic pressure in the vehicle groups was 41.0±11.7 mm Hg, and in the PK10453 (Structure 2) group, was 43.1±3.5 mm Hg (p=NS). After five days of treatment, the PA systolic pressure was 69.4±12.9 mm Hg in the vehicle group and was significantly lower at 47.3±3.0 mm Hg in the PK10453 group (p<0.01). On treatment day 8, the PA systolic pressure in the vehicle group was 83.5±8.5, but significantly lower at 47.3±4.9 mm Hg in the PK10453 group (p<0.001).

In a separate PK10453 (Structure 2) telemetry study, at day 1 prior to start of treatment, the PA systolic pressure in the vehicle group was 47.4±10.2 mm Hg, and in the PK10453 group, was 43.1±3.5 mm Hg (p=NS). After five days of treatment, the PA systolic pressure was 67.4±1 1.4 mm Hg in the vehicle group and was significantly lower at 47.2±3.0 mm Hg in the PK10453 group (p=0.03). On treatment day 9, the PA systolic pressure in the vehicle group was 92.8±9.1 mm Hg, but significantly lower at 50.5±7 mm Hg in the PK10453 group (p=0.03). For the imatinib telemetry study (study 4), at day 1, the PA systolic pressure in the vehicle group was 51.4±8.9 mm Hg, and in the imatinib group 41.5±3.5 mm Hg. At treatment day 9 the PA systolic pressure in the vehicle group was 80.4±14.2 mm Hg, and in the imatinib group was 75.1±7 mm Hg (p=NS). See FIG. 6.

Measurement of RV Pressure and PV Loops in the MCT+PN Model; PK10453 (Structure 2) Dose Response Study.

In a separate cohort of animals, the MCT+PN model was developed as described. RV pressure was obtained after 14 days of vehicle exposure, and PK10453 treatment with 4 min (D4) and 8 min exposures (D8) three times a day. In the vehicle group (n=9), RV systolic pressure was 75.7±7.1 mm Hg, in the D4 group (n=10) RV systolic pressure was 40.4±2.7 mm Hg, and in the D8 MCT+PN group RV systolic pressure was 43±3.0 mm Hg (p0.001 V vs. D4 and V vs. D8; FIG. 7A). PV loops were obtained in a subset of animals from each group (Vehicle n=3; D4 n=5, D8 n=4).

Example 4—MCT+PNMCT+PN Model Efficacy

PVloop Study.

The RV end systolic pressure (ESP) was lower and the RV ejection fraction (EF) was higher in both the D4 and D8 treatment groups compared to vehicle control. Cardiac output in the D8 group was increased compared to the Vehicle group. See Table 3. The study animals underwent left pneumonectomy followed 7 days later by MCT 60 mg/kg IP. Two weeks after MCT administration, PK10453 (Structure 2) or vehicle were given by inhalation three times a day for two weeks. PV loops were acquired at the end of this period. With respect to Table 3: V=vehicle; D4=4 min inhalation PK10453; D8=8 min inhalation PK10453; n=4 each group; *p<0.001; **p<0.01; §p<0.05 vs. V.

TABLE 3

| Group | Sel | HR (bpm) | ESP (mm Hg) | EDP (mm Hg) | ESV (μl) | EDV (μl) | SV (μl) | CO ml/min | EF | SW |
|---|---|---|---|---|---|---|---|---|---|---|
| V | Mean | 290 | 83.21 | 10.31 | 484.17 | 621.32 | 137.15 | 39.03 | 25.43 | 10123 |
| | SEM | 25 | 3.49 | 1.24 | 148.32 | 139.49 | 14.19 | 0.62 | 8.36 | 2698 |
| D4 | Mean | 288 | 43.20* | 2.62§ | 144.14 | 408.95 | 264.81 | 77.59 | 65.4** | 9818 |
| | SEM | 21 | 6.08 | 0.30 | 25.89 | 34.94 | 12.66 | 2.59 | 3.47 | 769 |
| D8 | Mean | 315 | 38.44* | 4.87 | 155.40 | 488.68 | 333.28** | 105.1** | 67.1** | 5481 |
| | SEM | 41 | 1.43 | 1.86 | 22.69 | 52.00 | 49.81 | 15.51 | 4.59 | 1829 |

Effect of PK10453 (Structure 2) on RV Hypertrophy.

Treatment with PK10453 resulted in a significant decrease in RV hypertrophy in the rat MCT+PNMCT+PN model. See FIG. 7B. The (RV+IVS)/LV ratio in the vehicle group (n=11) was 0.88±0.05, in the PK10453 D4 group (n=13) was 0.62±0.04, and in the PK10453 D8 group (n=7) was 0.68±0.05 ($p<0.001$ D4 vs. V; $p=0.012$ D8 vs. V).

Analysis of Pulmonary Arteriole Histology and Morphology.

The lumen area to media area ratio (L/M) was significantly higher in the PK10453 (Structure 2) treated D8 group compared to the D4 or vehicle groups: D8 (n=5) L/M 0.72±0.05, D4 (n=6) L/M 0.33±0.06, and the vehicle control V (n=6): 0.26±0.04 (p0.0001 D8 vs. V or D8 vs. D4). See FIG. 7C. Occlusion analysis was performed on the same animal samples used for the lumen/media ratio measurements. The occlusion analysis demonstrated a significant reduction in Grade 2 occlusion lesions in the PK10453 D8 treatment group (V (n=6) 41.5±7.1%, D4 (n=6) 28.5±4.2%; D8 11.4±4.1%; $p<0.01$ D8 vs. V; see FIG. 7D. FIG. 8A shows an H&E stain of an occlusive (Grade 2) lesion in a vehicle treated animal (MCT+PN model); comparison is made to a Grade 0 vessel from a PK10453 (D8) treated animal. See FIG. 8B. An example of a Grade 2 lesion stained for phospho-PDGFRbeta is shown in FIG. 8C with comparison to a Grade 0 lesion from a PK10453 (D8) treated animal (MCT+PN model) in FIG. 8D. Staining for phosphoPDGFRbeta showed intense signal in a cobblestone pattern in Grade 2 lesions.

Further examples of pulmonary arteriole hypertrophy and intraluminal cellular proliferative lesions are shown as described, while the quantitative analysis is represented in FIG. 9. The lumen area to media area ratio (L/M) was significantly higher in the PK10453 treated groups compared to vehicle, where the higher dose, D8 (n=4) L/M 1.17±0.07, the lower dose, D4 L/M 0.75±0.14, and the vehicle control V (n=6): 0.36±0.09 ($p=0.032$ D4 vs. V; $p=0.00014$ D8 vs. V; $p=0.028$ D8 vs. D4). The endothelial cell marker, vWF, showed signal predominantly within the pulmonary arterioles. The tyrosine705 phosphoSTAT3 antibody showed localization of pSTAT3 to nuclei of endothelial cells and perivascular cells. See FIG. 10A; and FIG. 10B (with PK10453 treatment).

Trichrome and Immunohistochemistry for Alpha-SMC Actin, and vWf.

The endothelial cell marker, vWF, showed signal predominantly within the pulmonary arterioles. And immunohistochemistry for vascular SMCs (αSMC actin), endothelial cell markers (vWF) and trichrome stains of pulmonary arterioles in the rat MCT+PN was performed to further characterize Grade 0, 1, and 2 lesions. Grade 0 lesions were characterized by early neointimal (intraluminal) proliferation of endothelial cells (ECs) with preservation of vascular SMCs in the media; Grade 1-2 lesions, by neointimal (intraluminal) proliferation/invasion of mixed myofibroblast-like cells (MFs) and ECs with partial loss of vascular smooth muscle cells in the medial layer; and advanced Grade 2 lesions, by extensive MF/EC intraluminal proliferation with complete loss of VSM cells in the medial layer and fibrotic replacement of the media. See FIGS. 11A-I.

Example 5—Immunohistochemistry for PDGF Signaling

In pre-capillary pulmonary arterioles signaling through the PDGFR-β pathway was dominant. Signal for PDGFAA ligand and PDGFR-α were present but qualitatively lower than signal for PDGFBB and PDGFR-β. Phosphorylated PDGFR-β (pPDGFR-β) had a cobblestone appearance in neointimal cells and in perivascular cells and was stronger than signal for phospho-PDGFR-α (PDGFR-α) in precapillary pulmonary arterioles. Minimal signal for pPDGFR-β or alpha was detected in the medial layers of the precapillary pulmonary arterioles. See FIGS. 12A-F. In larger (>50 μm) vessels, signal for pPDGFR-α was present in medial VSM cells. In contrast, pPDGFRβ medial layer signal was low. See FIGS. 13A-D.

Example 6—NanoPro® Immunoassays and Western Blots

Nanopro® Immunoassays for pAKT/AKT are shown in FIG. 14 and pSTAT3/STAT3 are shown in FIG. 15. There was a significant reduction in the pSTAT3/STAT3 ratio in both the D4 and D8 groups compared to vehicle. FIG. 16 shows the effect of inhaled PK10453 (Structure 2) on ppERK1/ERK1, pERK1/ERK1, ppERK2/ERK2 and pERK2/ERK2 in lung homogenates. There were significant reductions in ppERK1/ERK1 and pERK1/ERK1 in the D4 and D8 groups, respectively, compared to vehicle.

Example 7—PDGFAA Stimulates PDGFR-α. Whereas PDGFBB Binds & Activates PDGFR-β

FIG. 17 shows the effect of imatinib, PK10453 (Structure 2), and PK10571 (Structure 2a) on PDGFAA vs. PDGFBB stimulated phosphorylation of ERK1 and ERK2 in human fetal lung fibroblasts. The ratio diphosphorylated ERK1 to total ERK1 (ppERKWERK1) was increased with PDGFAA or PDGFBB stimulation, and significantly decreased at 1 μM and 10 μMy concentration of imatinib, PK10453, and PK10571. The ratio diphosphorylated ERK2 to total ERK2 (ppERK2/ERK2) was increased with PDGFAA or PDGFBB stimulation (10 ng/ml), and significantly decreased at 1 uM and 10 uM concentration of imatinib, PK10453, and PK10571. After PDGF BB stimulation, the ratio of diphosphorylated ERK1 to total ERK1 (ppERK1/ERK1) and diphosphorylated ERK2 to total ERK2 (ppERK2/ERK2) was more effectively decreased at 1 uM PK10453, and PK10571 compared to imatinib. Thus, PK10453 and PK10571 are more potent inhibitors of PDGF BB stimulated ERK1 and ERK2 phosphorylation compared to imatinib.

In particular, and with reference to FIG. 17A-D as noted above, PDGFAA and PDGF BB (10 ng/ml) stimulation of human fetal lung fibroblasts increased ppERK1/ERK1 and ppERK2/ERK compared to serum free media only controls (SF). Imatinib, PK10453 (Structure 2), and PK10571 (Structure 2a) were equally effective at 1 uM in decreasing PDGF AA stimulated ppERK1 and ppERK2 formation (FIGS. 17A and C). However, PK10453 and PK10571 were more effective at 1 uM and 10 uM in decreasing PDGF BB stimulated ppERK1 and ppERK2 (FIGS. 17B and D). These data demonstrate that PK10453 and PK10571 are more effective in blocking signal transduction through the PDGF receptor beta compared to imatinib. Data shown are mean±SEM. The differential effect of PK10453 and PK10571 was more prominent in blocking ERK1 vs. ERK2 phosphorylation. At 1 uM imatinib had no effect on inhibition of ppERK1 formation whereas PK10453 and PK10571 at 1 uM were effective in decreasing PDGFBB stimulated ppERK1 formation. PK10453=structure 2; PK10571=structure 2a. Platelet derived growth factor receptor alpha=PDGFR-alpha=PDGFR-α=PDGF receptor alpha=PDGF alpha receptor. Platelet derived growth factor receptor beta=PDGFR-beta=PDGFRβ=PDGF receptor beta=PDGF beta receptor.

Example 8—PK10453 (Structure 2). PK10467 (Structure 3). PK10468 (Structure 4). PK10569 (Structure 5) and PK10571 (Structure 2a) Possess Lower IC$_{50}$ Concentrations Compared to Imatinib for Inhibiting PDGFBB Stimulated AKT Phosphorylation in Fibroblasts Fetal human lung fibroblasts grown in cell culture are used as a model of fibroblast proliferation that occurs in pulmonary arterial hypertension, pulmonary fibrosis, and related disorders. See FIG. 18A-D. These data highlight that PK10453, PK10467, PK10468, PK10569, and PK10571 are more potent inhibitors of signal transduction mediated through the PDGF beta receptor compared to imatinib. These data show the importance of effective inhibition of PDGF beta receptor signaling in addition to PDGF alpha receptor signaling as a treatment for pulmonary arterial hypertension, pulmonary fibrosis, and related disorders which can be achieved with PK10453, PK10467, PK10468, PK10569, and PK10571. As used above and throughout the application, the PK compounds and structure designations are used interchangeably, as follows: PK10453=Structure 2; PK10571=Structure 2a; PK10467=Structure 3; PK10468=Structure 4; and PK10569=Structure 5. See FIG. 18A-D.

Example 9—Body Weights. Systemic BP, and Plethysmography Studies

Compared to vehicle, there was a trend to a slower rate of decline in body weight in the treated vs. vehicle groups. See FIG. 19. On day seven of treatment, systolic BP was 111±21 mmHg in the MCT vehicle group (n=3) compared to 131±10 mmHg in the MCT PK10453 group (n=3), as shown in FIG. 20. Two-chamber plethysmography was measured at day 1 and day 15 of PK10453/vehicle administration in the rat MCT+PNMCT+PN model. The results are shown in Table 4. Treatment with PK10453 was associated with a slower decline in minute ventilation (MV), and a significant improvement in peak inspiratory flow (PIF) and peak expiratory flow (PEF) in the 4 min exposure group (D4) compared to vehicle.

TABLE 4

| Drug Group | | Day1 | | | | | | Day15 | | | | | |
|---|---|---|---|---|---|---|---|---|---|---|---|---|---|
| | | PIF | PEF | TV (ml) | MV (ml/min) | f | SRaw | PIF | PEF | TV | MV | f | SRaw |
| V (n = 6) | mean | 8.81 | 9.68 | 0.86 | 193.66 | 244.79 | 40.37 | 4.97 | 5.86 | 0.52 | 107.59 | 214.43 | 38.93 |
| | sem | 0.79 | 0.98 | 0.14 | 20.66 | 28.02 | 4.11 | 0.39 | 0.44 | 0.07 | 9.58 | 13.83 | 6.53 |
| D4 (n = 5) | mean | 9.82 | 11.04 | 1.00 | 223.24 | 224.68 | 39.73 | 7.82* | 9.33* | 0.85 | 176.12§ | 217.12 | 33.09 |
| | sem | 0.70 | 0.56 | 0.07 | 11.99 | 9.87 | 3.33 | 0.34 | 0.67 | 0.12 | 14.53 | 18.64 | 4.80 |
| D8 (n = 5) | mean | 8.54 | 9.43 | 0.74 | 174.68 | 259.13 | 36.01 | 6.06 | 6.64 | 0.63 | 128.49 | 232.11 | 49.26 |
| | sem | 0.72 | 1.01 | 0.15 | 22.32 | 26.42 | 3.82 | 0.84 | 0.99 | 0.16 | 19.47 | 30.71 | 7.11 |

Abbreviations:
PIF: peak inspiratory flow;
PEF: peak expiratory flow;
TV: tidal volume;
MV: minute ventilation;
f: breathing frequency (breaths per minute);
SRaw: airway resistance
*p < 0.01 D4 vs. V;
§ p = 0.02 D4 vs. V.

Example 10—Discussion and Applied Embodiments

The PDGF signaling pathway has been found to be activated in human pulmonary arterial hypertension (PAH) and in animal models of the disease. This study tested the hypothesis that a novel, non-selective inhaled PDGF receptor inhibitor, PK10453 (Structure 2), would decrease pulmonary hypertension both in the rat monocrotaline (MCT) model and the rat MCT plus pneumonectomy (+PN) model of PAH. PK10453 delivered by inhalation, for four (D4) and eight (D8) min exposures three times a day for two weeks, decreased right ventricular systolic pressure (RVSP) in both the rat MCT and rat MCT+PN models: vehicle MCT group (n=6) RVSP was 80.4±2.6 mm Hg; in the D4 MCT group (n=6), 44.4±5.8 mm Hg; and in the D8 MCT group (n=5), 37.1±4.5 mm Hg (p<0.001 vs. vehicle); in the vehicle MCT+PN group (n=9) RVSP was 75.7+7.1 mm Hg; in the D4 MCT+PN group (n=10), 40.4+2.7 mm Hg, and in the D8 MCT+PN group (n=8), 43.0+3.0 mm Hg (p<0.001). In the rat MCT+PN model, continuous telemetry monitoring of pulmonary artery pressures also demonstrated that PK10453 prevented the progression of PAH. Imatinib given by inhalation was equally effective in the MCT model, but was not effective in the MCT+PN model.

Immunohistochemistry demonstrated increased activation of the PDGFβ receptor compared to the PDGFα receptor in neointimal and perivascular lesions found in the MCT+PN model. It was shown that imatinib is selective for the PDGFα receptor whereas PK10453 has a lower $IC_{50}$ for inhibition of kinase activity of both the PDGFα and PDGFβ receptors compared to imatinib. PK10453 decreased the ratio of phosphorylated AKT (Ser473) to total AKT, phosphorylated STAT3 (Y705) to total STAT3, the ratio of diphosphorylated ERK1 to total ERK1 and the ratio of monophosphorylated ERK1 to total ERK1 in lung extracts from MCT+PN animals. In short, PK10453, when delivered by inhalation, significantly decreased the progression of PAH in the rat MCT and MCT+PN models. Non-selective inhibition of both PDGFα and PDGFβ receptors therefore has a therapeutic advantage over the selective inhibition of PDGFRα at least in PAH and related diseases.

Accordingly, and for the first time, it has been shown that a novel, non-selective PDGF receptor inhibitor, PK10453 (Structure 2), when administered by inhalation, decreased the severity of PAH in two animal models of the disease: the rat MCT, and the rat MCT+PN model. As such, because PK10453 is highly potent against both the PDGFRα and PDGFRβ receptors, while imatinib is selective for the PDGFRα receptor, PK10453 possesses surprisingly superior efficacy. Both PK10453 and imatinib were effective in the rat MCT model, but only PK10453 decreased pulmonary hypertension in the rat MCT+PN model when administered by inhalation. One reason for this differential effect may be due to hyper-activation of signaling through the PDGFRβ receptor in precapillary pulmonary arteriole neointimal lesions compared to the PDGFRα receptor in the rat MCT+PN model.

Accordingly, the present data demonstrates that a novel, non-selective, PDGF receptor inhibitor PK10453 (Structure 2) when delivered by inhalation prevented the progression of PAH in both the rat MCT and the rat MCT+PN models. Of note, this is the first study to report efficacy of PDGF receptor inhibition in the rat MCT+PN model. A sustained reduction in PA pressure was also found in ambulatory PAH (MCT+PN) animals treated with PK10453. Concomitant with a significant reduction of PA and RV systolic pressure in these models, a reduction in RV hypertrophy and an improvement in the lumen to media ratio of pulmonary arterioles were demonstrated. Pressure volume loops displayed an improvement in RV ejection fraction, a higher cardiac output, and a trend towards lower stroke work in PK10453 treated animals compared to control animals. In lung extracts of PK 10453 treated animals, there was a significant reduction in the pAKT(Ser473)/AKT, pSTAT3/STAT3, ppERK1/ERK1 and pERK1/ERK1 ratios.

Because PAH is a disease substantially localized to the lung, the hypothesis was tested that direct administration of the drug to the target site via inhalation would offer the advantage of higher local concentrations (greater efficacy) and lower systemic concentrations of drug (lower side effects). Pharmacokinetic studies demonstrated a 45 fold advantage of inhalation delivery compared to intravenous administration of PK10453 (Structure 2). While PK10453 decreased RV systolic pressure by 50% in the rat MCT model, it did not have an adverse effect on systemic BP. Additionally, inhaled PK10453 did not adversely affect lung function over a 2-wk course.

In the rat MCT model the present inventor compared inhaled PK10453 to inhaled imatinib and found both to be equally effective. These results are consistent with prior reports that the PDGF receptor inhibitor imatinib, when delivered systemically, decreased pulmonary hypertension in the rat MCT model See Schermuly et al., "Reversal of experimental pulmonary hypertension by PDGF inhibition." *J Clin Invest;* 115:281 1-21 (2005). However, in the rat MCT+PN model while inhaled PK10453 was effective in lowering pulmonary pressures, inhaled imatinib was not. The rat MCT+PN model is a more aggressive model of PAH compared to the MCT only model, and may more accurately reflect the pathology of the human disease. White et al., "Plexiform-like lesions and increased tissue factor expression in a rat model of severe pulmonary arterial hypertension." *Am J Physiol Lung Cell Mol Physiol;* 293:L583-90 (2007). In vitro measurement of $IC_{50}$ for inhibition of PDGF-α and -β receptors showed that PK10453 was more potent than imatinib against both isoforms, and that imatinib is only a modest inhibitor of the PDGFRβ isoform. Immunohistochemistry demonstrated that the neointimal lesions in the rat MCT+PN model have high levels of phospho PDGFRβ, with less pPDGFRα. These findings explain why non-selective inhibition of both PDGFRβ and PDGFRα provided a therapeutic advantage over the selective inhibition of PDGFRα.

The present data are consistent with Panzhinskiy et al., "Hypoxia induces unique proliferative response in adventitial fibroblasts by activating PDGFbeta receptor-JNK1 signaling." *Cardiovasc Res;* 95:356-65 (2012), for the neonatal calve model of high altitude induced pulmonary hypertension. In that model extensive perivascular proliferation of adventitial fibroblasts was demonstrated along with activation of pPDGFRβ. These lesions are similar to the pattern observed in the rat MCT+PN model for the present studies. These findings are also consistent with those reported for human PAH. Perros et al., "Platelet-derived growth factor expression and function in idiopathic pulmonary arterial hypertension." *Am J Respir Crit Care Med;* 178:81-8 (2008), describing the distribution of PDGFA, PDGFB, PDGFRα, PDGFRβ and pPDGFRβ in pulmonary arterial lesions of patients with PAH. PDGFRα expression was found mainly within the muscular medial layer of hypertrophied pulmonary arterioles, whereas PDGFRβ and pPDGFRβ were dominant in endothelial cells of plexiform lesions.

The selectivity of imatinib for PDGFRα has not been previously emphasized in studies of PAH. Inhibition by imatinib of PDGFAA stimulated PDGFRα phosphorylation was reported to be 0.1 µM; whereas inhibition of PDGFBB stimulated PDGFRβ phosphorylation at 0.38 µM. See, e.g., Deininger et al., "The development of imatinib as a therapeutic agent for chronic myeloid leukemia." *Blood;* 105: 2640-53 (2005). Here, however, it was determined that, at [ATP]Km(app), imatinib was 10 fold more selective for PDGFRa compared to the—beta receptor ($IC_{50}$ against PDGFRα 71 nM vs. 607 nM for PDGFRβ). Most PAH related cell based studies interrogating the PDGFR pathway employed high doses of imatinib (5-10 µM) and thus preclude distinction between PDGFRα and β receptor inhibition.

Wu et al., "Comprehensive dissection of PDGF-PDGFR signaling pathways in PDGFR genetically defined cells." *PLoS One;* 3:e3794 (2008), examined PDGFR signaling in genetically defined mouse embryonic fibroblasts (MEFs). The MEFs were engineered to express only the PDGFRa, PDGFRβ, both or neither receptor. Signaling through the PDGFRα receptor and the PDGFRβ receptor were found to have both shared and distinct pathways. Thirty-three gene sets were distinctly activated by PDGFRα and 15 by PDGFRβ. PDGFRα/β heterodimers activated components of NFκB and IL-6 signaling. Calcium flux pathways were regulated by both PDGFRα and PDGFRβ. Signaling involved with angiogenesis was solely regulated via the PDGFRβ pathway. This finding comports with the selective increase in phosphoPDGFRβ found with neointimal lesions of precapillary pulmonary arterioles using the MCT+PN model.

PDGFBB has been found to induce phosphorylation of AKT at Ser473 in pulmonary artery smooth muscle cells and fibroblasts, but not pulmonary arterial endothelial cells. See Ogawa et al., "PDGF enhances store-operated $Ca^{2+}$ entry by upregulating STIMI/Orail via activation of Akt/mTOR in human pulmonary arterial smooth muscle cells." *Am J Physiol Cell Physiol;* 302:C405-11 (2012). Increased phosphorylation of AKT (Ser473) was also found in cells with a smooth muscle phenotype from endarterectomies of patients with chronic thromboembolic pulmonary arterial hypertension. See Ogawa et al., "Inhibition of mTOR attenuates store-operated $Ca^{2+}$ entry in cells from endarterectomized tissues of patients with chronic thromboembolic pulmonary hypertension." *Am J Physiol Lung Cell Mol Physiol;* 297: L666-76 (2009). PDGFBB stimulation increased store operated calcium entry via the AKT/mTOR pathway in these cells. See id.

In pulmonary artery smooth muscle cells from control and monocrotaline treated rats, however, imatinib (0.1 μM) decreased fetal calf serum stimulated Ser473 AKT phosphorylation, but had no effect on phosphorylation of AKT at Thr30825. At this concentration it is likely that imatinib was acting via the PDGFα receptor. Wu et al. (2008) found that STI-571 (imatinib) at 5 μM blocked PDGFBB stimulated AKT phosphorylation (SER473) in both PDGFRβ null and PDGFRα null cell lines. The present invention included an ICW to examine PDGFAA and PDGFBB stimulation of AKT (Ser473) and AKT (Thr308) phosphorylation in fetal human lung fibroblasts. Inhibition by imatinib was compared to PK10453 inhibition of PDGFAA or PDGFBB stimulated AKT phosphorylation, and found that PK10453 was more potent.

Nano-fluidic proteomic immunoassays, moreover, were employed to quantify phosphorylated species of AKT, STAT3 and ERK1/2 in lung extracts of MCT+PN animals. A significant reduction of phospho-AKT (Ser473), phospho-STAT3 and ppERK1/ERK and pERK1/ERK1 in the PK10453 treated groups was found as compared to vehicle. Schermuly et al. (2008) demonstrated a reduction in pERK1/2 by imatinib in the rat MCT model of PAH. Jasmin et al., "Short-term administration of a cell-permeable caveolin-1 peptide prevents the development of monocrotaline-induced pulmonary hypertension and right ventricular hypertrophy." *Circulation;* 114:912-20 (2006), have shown activation of STAT3 in the rat MCT model, and Masri et al., "Hyperproliferative apoptosis-resistant endothelial cells in idiopathic pulmonary arterial hypertension." *Am J Physiol Lung Cell Mol Physiol;* 293:L548-54 (2007), found that STAT3 was activated in human idiopathic PAH. The nano-fluidic proteomic immunoassays of the present invention were previously used to examine the effects of imatinib on pSTAT3, and pERK1/2 in chronic myelogenous leukemia (CML). See Fan et al., "Nanofluidic proteomic assay for serial analysis of oncoprotein activation in clinical specimens." *Nature medicine;* 15:566-71 (2009). This assay has utility in distinguishing monophosphorylated isoforms and diphosphorylated isoforms of proteins. For example, patients with CML who responded to imatinib had a distinct reduction in levels of monophosphorylated ERK214. Here, the ERK1 isoform and both the diphosphorylated form of ERK1 and the monophosphorylated form of ERK1 predominated in lungs of MCT pneumonectomized rats. Treatment with PK10453 significantly decreased ppERK1/ERK and pERK1/ERK1.

Occlusion analyses were performed in accordance with the method of Homma et al., "Involvement of RhoA/Rho kinase signaling in protection against monocrotaline-induced pulmonary hypertension in pneumonectomized rats by dehydroepiandrosterone." *Am J Physiol Lung Cell Mol Physiol;* 295:L71-8 (2008). In the rat MCT+PN model, the higher dose of inhaled PK10453 was associated with fewer Grade 2 occlusive lesions. These lesions were then characterized by immunohistochemistry with markers for vascular smooth muscle cells, and endothelial cells, and performed trichrome stains to differentiate muscular from fibrotic lesions. It was determined that the neointimal proliferative grade 1-2 lesions contained myofibroblasts and endothelial cells. In advanced grade 2 lesions there was fibrotic replacement of the vessel media. The origin of myofibroblasts in these lesions is not entirely clear. They could originate from infiltration of peri-vascular fibroblasts or pericytes, from circulating stem cells, resident progenitor cells, or as a consequence of endothelial-mesenchymal transition. See Yeager et al., "Progenitor cells in pulmonary vascular remodeling." *Pulm Circ;* 1:3-16 (2011). While these lesions were detected, it is reasonable to propose that the type 1 lesion is an earlier stage lesion that can progress to type 2 and type 3. In this model, intraluminal endothelial cells proliferate, transition to a myofibroblast phenotype (and/or the lumen is infiltrated by perivascular cells/myofibroblasts) and progressively occlude the vessel lumen.

Sakao et al., "Reversible or irreversible remodeling in pulmonary arterial hypertension." *Am J Respir Cell Mol Biol;* 43:629-34 (2010), have highlighted the importance of distinguishing regression of vascular muscularization (reverse remodeling) from potentially irreversible endothelial cell proliferation in PAH. The data presented here shows that signaling through the PDGFRα pathway plays an important role in vascular remodeling of larger pulmonary arterioles in PAH, whereas the PDGFRβ pathway is more important in the proliferative neointimal lesions of precapillary pulmonary arterioles. Targeting the PDGFRβ pathway with a PDGFR inhibitor that potently blocks this isoform (more potently than imatinib) may influence progression of these lesions. If such lesions are therefore treated before full fibrotic replacement and vessel regression reversibility of these lesions may exist.

In conclusion, an inhaled, non-selective PDGF receptor inhibitor, PK10453 (Structure 2), was effective in both the MCT, and MCT+PN rat models of PAH. Treatment with PK10453 was associated with a significant reduction in pulmonary arterial pressures in ambulatory animals, an improvement in right ventricular function, and a reduction in RV hypertrophy. Histologic analysis demonstrated an improvement in the pulmonary arteriole lumen to media ratio in animals treated with PK10453 and a decrease in the phosphorylation state of AKT (Ser473), STAT3 and ERK1. There was no significant effect of PK10453 (Structure 2) on systemic blood pressure, and no adverse effect of PK10453 on lung function. In contrast to imatinib, PK10453 is not selective for the PDGFRα receptor, but rather is highly potent against both the PDGFRα and β isoforms. Because the PDGFRβ pathway is more highly activated than the PDGFRα receptor in plexiform lesions of PAH, a non-selective PDGFR inhibitor, e.g., PK10453, thus possesses efficacy against PAH and related diseases and disease pathways.

Examples Continued

Example A: PK10571 with Leucine as Excipient

PK10571 solubility is 50 mg/ml In EtOH (and up to 1:1 EtOH:H$_2$O mixture) but insoluble in water at neutral pH. L-Leucine, typically soluble up to 25-30 mg/ml in water and insoluble in EtOH; A series of solubility experiments with L-Leucine in ethanol/water mixtures found that L-Leucine precipitated between 5-10 mg/ml (solution) for a 1:1 v:v EtOH:H$_2$O solution at room temperature. Higher Leucine concentrations were obtained, up to 13 mg/ml with a 2:1 EtOH:H$_2$O mixture. Given PK10571 solubility of 50 mg/ml at 1:1 v:v EtOH:H$_2$O, the ratio of Leucine excipient to API will be between 20-60% or greater in the final powder. To maximize the amount of hydrophobic shell former (Leucine) on the surface, a higher ratio is desired.

Various methods are available to those skilled in the art to manufacture a spray dry powder containing the desired ratio of leucine to PK10571. One method utilizes an internal mixing approach in which the API and excipient is provided to the nozzle in separate feed streams, one ETOH and the second aqueous. By varying either the relative feed rate and/or feed concentrations the mass ratio of excipient to API is modulated. Another method utilizes heating and a "hot-start" such that the solution to be spray dried is heated to keep the drug and excipient in solution. Table 5, shows the results of the internal mixing approach.

Spray Drying

The spray dryer is operated with a target chamber outlet temperature of 60-70° C. and a calculated outlet relative saturation level below 10% to produce powder with low residual solvent levels. The atomizer design and operation is based upon methods known to those skilled in the art to target particle sizes for pulmonary delivery. As shown below, Table 5 reveals shows various ratios of PK10571 and leucine used to generate a spray dry powder with inhalable characteristics such that an effective dose can be delivered to a human or animal to treat a disease affecting the lung and/or pulmonary vasculature.

TABLE 5

Examples of Parameters used to spray dry API (PK10571) with Leucine.

| ID | EtOH ml/min | EtOH g/min | Water ml/min | Water g/min | EtOH/water v/v | EtOH/water mass/mass | Leu mg/ml | Leu % TS | Leu Mass g/min |
|---|---|---|---|---|---|---|---|---|---|
| PK01 | 1 | 0.79 | 5 | 5 | 0.2 | 0.158 | 10 | 1 | 0.05 |
| PK02 | 1.26 | 0.995 | 4 | 4 | 0.315 | 0.24875 | 10 | 1 | 0.04 |
| PK03 | 2.5 | 1.975 | 4 | 4 | 0.625 | 0.49375 | 10 | 1 | 0.04 |
| PK04 | 5 | 3.95 | 4 | 4 | 1.25 | 0.9875 | 10 | 1 | 0.04 |
| PK05 | 1.26 | 0.995 | 4 | 4 | 0.315 | 0.24875 | 20 | 2 | 0.08 |
| PK06 | 2.5 | 1.975 | 4 | 4 | 0.625 | 0.49375 | 20 | 2 | 0.08 |
| PK07 | 5 | 3.95 | 4 | 4 | 1.25 | 0.9875 | 20 | 2 | 0.08 |

| ID | API mg/ml | API conc % TS | API mass g/min | Leu/API mass ratio | ETOH + water g/min | Solution g/min | Solids g/min | Soln | Target powder out g | Btach Powder g | API g |
|---|---|---|---|---|---|---|---|---|---|---|---|
| PK01 | 20 | 2 | 0.016 | 3.165 | 5.79 | 5.86 | 0.066 | 1.1 | 0.4 | 0.667 | 0.16 |
| PK02 | 20 | 2 | 0.02 | 2.009 | 4.995 | 5.055 | 0.06 | 1.2 | 0.4 | 0.667 | 0.22 |
| PK03 | 20 | 2 | 0.04 | 1.013 | 5.975 | 6.055 | 0.08 | 1.3 | 0.4 | 0.667 | 0.331 |
| PK04 | 20 | 2 | 0.079 | 0.506 | 7.95 | 8.069 | 0.119 | 1.5 | 0.4 | 0.667 | 0.443 |
| PK05 | 20 | 2 | 0.02 | 4.018 | 4.995 | 5.095 | 0.1 | 2 | 0.4 | 0.667 | 0.133 |
| PK06 | 20 | 2 | 0.04 | 2.025 | 5.975 | 6.095 | 0.12 | 2 | 0.4 | 0.667 | 0.22 |
| PK07 | 20 | 2 | 0.079 | 1.013 | 7.95 | 8.109 | 0.159 | 2 | 0.4 | 0.667 | 0.331 |

To determine the characteristics of the spray dry powder various assays are used. On such assay is cascade impaction which determines the mass median aerodynamic diameter of the spray dry powder particles. The particle size distribution of PK01-PK07 was measured with the Next Generation Impactor (NGI) cascade impactor. Table 6 below shows results of NGI cascade impaction for spray dry powders containing PK10571 and Leucine.

TABLE 6

| Sample ID | T | PS | 1 | 2 | 3 | 4 | 5 | 6 | 7 | 8 | MMAD* | GSD |
|---|---|---|---|---|---|---|---|---|---|---|---|---|
| PK01 | 3.35 | 0 | 3.299 | 20.42 | 12.39 | 8.37 | 2.74 | 2.67 | 20.57 | 90.21 | NA | |
| PK02 | 14.4 | 5.2 | 11.88 | 29.35 | 70.17 | 70.45 | 22.2 | 41.2 | 21.54 | 8.8 | 2.32 | 2.25 |
| PK03 | 11.83 | 13.73 | 13.87 | 15.06 | 64.56 | 195.81 | 114.82 | 16.77 | 14.88 | 15.04 | 1.95 | 1.57 |
| PK04 | 12.22 | 7.59 | 11.7 | 16.67 | 55.65 | 147.69 | 78.49 | 10.3 | 9.66 | 7.75 | 2.07 | 1.58 |
| PK05 | 5.99 | 1.6 | 2.01 | 8.67 | 21.8 | 50.9 | 18.96 | 7.85 | 7.7 | 12.8 | 1.99 | 1.67 |
| PK06 | 5.17 | 5.33 | 5.36 | 13.99 | 63.79 | 32.739 | 37.7 | 9.75 | 21.7 | 9.6 | 2.24 | 3.48 |
| PK07 | 14.22 | 12.27 | 12.09 | 28.54 | 90.35 | 128.21 | 40.052 | 23.7 | 19.37 | 16.14 | 2.32 | 1.76 |

Abbreviations: T=throat; PS=Pre-separator; Stages 1-8 results are shown in micrograms PK10571/ml of solvent used to dissolve the particles deposited in each stage of the NGI. MMAD=mass median aerodynamic diameter and is shown in microns. GSD=geometric standard deviation. The fine particle fraction for PK02-PK07 ranged from 81-90% where the cutoff value was <3 µM.

Example B. PK10571 Spray Dried with Both Trehalose and Leucine Excipients

In this example PK10571 is dissolved at 50 mg/ml in 50% ethanol along with trehalose 20 mg/ml and L-leucine 10 mg/ml. The solution is heated to 40-45° C., filtered through a 0.2 micron filter and spray dried while still heated at 40-45° C. PK61014 and PK61914 are designations for Spray Dry Powders, spray dried from a solution of PK10571, trehalose, and Leucine in 50% ethanol. Spray Drying was performed with a Yamato ADL311S spray dryer. The solution flow rate was 0.5 ml/min, inlet T=110° C.; outlet T=60° C.; nitrogen gas was used for the spray drying gas at a pressure of 0.3 mPA. This technique would work with many different types and models of spray dryers including, but not necessarily limited to a Buchi Spray dryer, a NIRO spray dryer, or an Anhydrol spray dryer.

NGI cascade impaction was performed at 60 L/min vacuum for 4 seconds; a Monodose dry powder inhaler with a number 3 HPMC capsule loaded with 10-20 mg of SDD was used. By NGI cascade impaction the MMAD and GSD for PK61914 was 3.3±1.9. The emitted dose was greater than 90%. The fine particle fraction with a cut-off of 3 microns was 63%. The concentration of PK 10571 in the Spray dry powders was measured by HPLC MS/MS. The following SDDs were analyzed: PK61014, PK61914, PK62514, PK03, PK04, PK05. See below.

Materials and Methods:

SDDs were provided by Pulmokine, the acetonitrile was obtained from Sigma-Aldrich (Cat #: 34851-4L, Lot #: SHBD7868V) as was the water: Sigma-Aldrich (Cat #: 270733-4L, Lot #: SHBD7051V). Methanol (Cat #: 34860-4L-R, Lot #: SHBD4483V) and Formic Acid were also purchased from Sigma-Aldrich (Cat #: 56302-10X1ML-F, Lot #: BCBM 1129V).

Analytical Methods:

The ionization settings are as follows: instrument: AB Sciex 3000 API MS with HSID upgrade; ionization: Electrospray ionization (ESI); Polarity: Positive; Source voltage: 5000 V; temperature: 375° C.; Curtain gas: 10 AU; Collision gas: 4 AU; Nebulizer gas (GS1): 10 AU; and Heater gas (GS2): 70 psi.

The Single-reaction-monitoring conditions included: transitions: PK10571 470.0-239.2 m/z Declustering Potential (DP): 16 V; Focusing Potential (FP): 60 V; Entrance Potential (EP): 7.5V; Collision Energy (CE): 30 V; Collision Cell Exit Potential (CXP): 22 V; and Dwell time: 100 msec. With respect to the HPLC conditions, an Agilent 1100 Series Stack Configuration was employed with an injection volume of 10 µL. The autosampler tray temperature was set at 20° C., with a flow rate of 0.3 mL/min. The column was a 100×2.1 mm Agilent Poroshell 120 SB-C18 (2.7 µM, 120 Å) with guard column and in-line filter, where the column oven was 40° C. The mobile phase was A—0.1% formic acid in water, B—0.1% formic acid in acetonitrile, where the gradient was set at 0-3 min, 35% B, 3-4 min, 65% B, 4-4.5 min, 65% B, 4.5-4.7 min, 35% B, and 4.7-6 min, 35% B.

Sample Preparation:

Standards (100, 50, 10, 5, 1, 0.5, 0.1, 0.05, and 0.01 µg/mL) and quality control samples (17, 7, and 0.7 µg/ml) were prepared in methanol from a 1 mg/mL stock solution of PK10571. For the analysis of the SDDs, an appropriate amount of powder was weighed out and diluted in methanol in order to obtain a measurable concentration within the linear range of the standard curve. See FIG. 21.

Data Analysis:

External standardization was performed by plotting the peak area of the PK10571 transition (470.0-239.2 m/z) as a function of the concentration µg/mL). A weighted $1/x^2$ regression prepared using the method of least squares was applied to the standards. Inclusion criteria for the generation of the standard curve were defined as a coefficient of variation (% CV) less than 15% and a percent accuracy within ±15%, except at the lower limit of quantification, where % CV less than 20% and percent accuracy within ±20% was acceptable. API content was determined as a weight percent of the total SDD analyzed. As Shown below in Table 7, linearity, precision, and accuracy data for the PK10571 calibrators (in methanol) was demonstrated, where "*" represents the lower limit of quantification was determined to be 0.01 µg/mL. As shown in Table 8, below, the API content analysis for PK10571 was determined for various SDDs that were generated.

TABLE 7

| Nominal Concentration (µg/mL) | Calculated Concentration (µg/mL) | % CV | % Accuracy |
|---|---|---|---|
| 0.01* | 0.010 | 3.01 | 100 |
| 0.05 | 0.046 | 6.54 | 92 |
| 0.1 | 0.115 | 2.33 | 115 |
| 0.5 | 0.477 | 1.80 | 95 |
| 1 | 1.01 | 1.21 | 101 |
| 5 | 4.62 | 2.74 | 92 |
| 10 | 11.0 | 0.96 | 110 |
| 50 | 51.9 | 0.76 | 104 |
| 100 | 90.4 | 0.93 | 90 |

TABLE 8

| Sample | API Content (% w/w) ± SD |
|---|---|
| PK61014 | 55.45 ± 0.84 |
| PK61914 | 56.43 ± 0.29 |

TABLE 8-continued

| Sample | API Content (% w/w) ± SD |
| --- | --- |
| PK62514 | 61.73 ± 0.32 |
| PK03 | 45.27 ± 0.48 |
| PK04 | 52.31 ± 1.20 |
| PK05 | 33.36 ± 0.30 |
| PK011 | 12.94 ± 0.25 |
| PK012 | 33.88 ± 0.45 |

Modulated differential scanning calorimetric analysis was used to measure the glass transition temperature of SDDs containing PK10571 and leucine, and SDDs containing PK10571/trehalose/leucine.

Modulated DSC (MDSC) was performed using a TA Instruments Q 100 differential scanning calorimeter equipped with a refrigerated cooling system (RCS). The purge gas was 50 mL/min nitrogen. Approximately 3-5 mg of material was weighed into an aluminum hermetic pan and the lid hermetically sealed. Samples were cooled to −90° C. then heated to 300° C. The samples were run using conventional MDSC with a period of 60 seconds, amplitude of ±1.5° C., and a heating rate of 2° C./min. Data were analyzed using TA Instruments Universal Analysis software. As shown below in Table 9, glass transition temperatures of SDDs containing PK10571/Leucine or PK10571/Leucine/trehalose were analyzed, where the single transition temperature indicates a homogenous and stable SDD. See FIG. 22 for an example of MDSC for PK04 showing glass transition temperature (Tg) at 101° C. FIGS. 23 and 24 respectively show: scanning electron micrographs (SEMs) of PK004 SDD containing PK10571 and L-leucine, where the morphology is that of dimpled spheres (FIG. 23); and a SEM of PK61914 SDD containing PK10571/Trehalose/Leucine, where the morphology is that of rippled/ridged spheres (FIG. 24).

TABLE 9

| Sample | $T_g$ (° C.) |
| --- | --- |
| PK03 Leu/API | 103 |
| PK04 Leu/API | 101 |
| PK05 Leu/API | 105 |
| PK61914 API/TRE:LEU | 110 |

FIG. 25 shows examples of use of a spray dry powder consisting of PK10571 and excipient leucine with or without trehalose for the treatment of Pulmonary Arterial Hypertension, where the IC50 against PDGFR alpha vs. beta kinase domains, as further discussed herein. As shown in FIG. 25, moreover, PK10453 and 10571 are more potent than imatinib against the beta isoform, where PK10571 is potent against both the PDGFR alpha and PDGFR beta isoforms. FIG. 26 shows PDGF BB stimulated pAKT in human lung fibroblasts. Each assay each concentration is done in duplicate. PK10453 IC50 0.15 µM. PK10571 IC50 0.05 µM. As we showed in our recent publication in Pulmonary Circulation, the IC50 for inhibition of PDGFBB stimulated AKT phosphorylation by imatinib was 1.8 µM.[16]

Preclinical Efficacy.

We performed a pre-clinical efficacy study of inhaled PK10571 in the rat MCT+PN model. We used the MCT+PN model, because in this model, neointimal pulmonary arteriole proliferative lesions occur in a manner similar to what is observed in the human disease. In this experiment, drug treatment was started later than in prior studies of PK10453.

In prior studies, PK10453 was started 2 weeks after MCT injection (3 weeks after pneumonectomy). In the PK10571 SDD study, treatment was started 3 weeks after MCT injection (4 weeks after pneumonectomy). It should be noted that pneumonectomized rats given MCT develop severe PAH starting two weeks after the MCT injection. (In MCT only rats, it takes longer for PAH to develop (i.e., 3 weeks)). The time course over which pulmonary hypertension develops in the MCT+PN model is compared to the MCT only model in FIG. 27, which shows a time course over which pulmonary hypertension develops in the MCT+PN model compared to MCT only model. A. PK10453 study time drug treatment started (See Pulm Circ 2014 8(1):82-102). B. PK10571 SDD study time treatment started in MCT+PN model. C. Start time typical for MCT only model. Data acquired via telemetry monitoring of PA pressures in ambulatory rats. (Note: Day 11 in MCT+PN model data not shown). See FIG. 27.

PK10571 MCT+PN Model Study Design and Performance.

PK10571 dry powder with leucine and trehalose excipient was administered by nose only inhalation 30 minutes (on average) twice a day to the rats, via a Vilnius Dry Powder Generator connected to a CH Technologies Exposure tower. Estimated average API dose deposited in lung 0.25 mg/kg (calculated from measurement of aerosol concentration and minute ventilation of pneumonectomized rat) with estimated human dose equivalent (HED) 0.04 mg/kg. The rat MCT+PN model is a very aggressive model of PAH and vehicle treated animals showed high mortality. The mode of death of these animals has not been fully characterized but may be related to RV failure. We have noted that although pulmonary pressures rise gradually and progressively over a period of two weeks after MCT injection, in the third week, animals may enter a "crisis" phase and die suddenly. There was a significant decrease over time of PA pressures in the group treated with inhaled PK10571 (22% reduction day 8 compared to day 1; 35% reduction day 8 vs. day 3 within the treatment group). This finding confirms the disease modifying potential of PK10571. One animal in the drug treatment group was euthanized for weight loss on day 5 as per our preset criteria. See FIG. 28.

These data show that PK10571 formulated as a dry powder containing leucine and trehalose was effective in lowering pulmonary artery pressures in animals with very severe PAH in an aggressive animal model of the disease, and suggests a survival benefit in this model. See FIG. 28. PK10571 can also be formulated as a dry powder containing leucine without trehalose. In short, FIG. 28 shows a reduction of PA pressure over time in MCT+PN rats treated with Inhaled PK10571 (n=5) treated group. Pressure data from PAC40 telemetry implants in PA. Vehicle group was n=7 but 4 vehicle animals died between days 2 and 4 of treatment. See text for details. Data shown are mean±SE.*p<0.05 Repeated measures ANOVA (note: day 1 PK10571 vs. Vehicle p=NS); Some Day 6 data files were lost for Drug group except for 1 animal, so this data point could not be used for analysis. (Day 1 of treatment=Day 21 post MCT; Day 31 post pneumonectomy). See FIG. 28.

Example C Showing PK10571 Spray Dried with 1,2-Distearoyl-sn-glycero-3-phosphocholine (DSPC)

Here, PK011 consisted of PK10571:DSPC in a 1:5 ratio with 1.5% total solids in ethanol, while PK012 consisted of PK10571:DSPC: Calcium chloride. Table 10 below shows the API content of PK10571 spray dried with DSPC excipient, which was measured by HPLC MS/MS and performed in triplicate (PK011 S7=PK011; PK012S8=PK012). Table 11 outlines the MMAD of PK10571 spray dried with DSPC as excipient. MMAD was determined by measuring concentration of API by UV spectroscopy in each stage of an NGI cascade impactor, where air flow was 60 L/min for 4 seconds. Highlighted section for emphasis only.

TABLE 10

| ID | Measured | Dilution | Conc. (ug/mL) | Solvent D | Starting A | Starting A | Starting B | % PK10571 | SD | % CV |
|---|---|---|---|---|---|---|---|---|---|---|
| PK011S7 | | | | | | | | | | |
| T1 | 13.9 | 10 | 139 | 3 | 417 | 0.417 | 3.2 | 13.03125 | | |
| T2 | 14 | 10 | 140 | 3 | 420 | 0.42 | 3.2 | 13.125 | | |
| T3 | 13.5 | 10 | 135 | 3 | 405 | 0.405 | 3.2 | 12.65625 | | |
| Mean | 13.8 | | | | | | | 12.9375 | 0.248039 | 1.917211 |
| PK012S8 | | | | | | | | | | |
| T1 | 37.6 | 10 | 376 | 3 | 1128 | 1.128 | 3.3 | 34.18182 | | |
| T2 | 37.5 | 10 | 375 | 3 | 1125 | 1.125 | 3.3 | 34.09091 | | |
| T3 | 36.7 | 10 | 367 | 3 | 1101 | 1.101 | 3.3 | 33.36364 | | |
| Mean | 37.27 | | | | | | | 33.87879 | 0.448444 | 1.323672 |

TABLE 11

| ID | T | PS | 1 | 2 | 3 | 4 | 5 | 6 | 7 | 8 | MMAD | GSD |
|---|---|---|---|---|---|---|---|---|---|---|---|---|
| PK011 | 24.859 | 30.548 | 10.617 | 57.727 | 134.412 | 197.596 | 76.294 | 11.727 | 0 | 0 | 2.55 | 1.6 |
| PK012 | 48.511 | 503.247 | 32.087 | 16.325 | 22.949 | 41.634 | 30.119 | 8.999 | 0 | 0 | 2.66 | 2.06 |

In PK10571 animals we also compared PA systolic pressure pre-dose and post-dose (approximately 1 hour post dose) (FIG. 29.). As shown in FIG. 29, PK10571 in MCT+PN model: pre and post dose (approximately 1 hour). Data shown for day 1-6 treatment. There was a transient decrease in pulmonary artery systolic pressure seen post dosing in the early stage of treatment (i.e., up to day 4), though this transient dose effect appeared to decrease later in treatment while the overall PA systolic pressure fell. These data suggest both vasodilatory and anti-proliferative effects of PK10571, with the later probably being more important.

Example D—PK10571 Efficacy in the SU5416/Hypoxia/Normoxia Model of PAH

The SU5416/hypoxia/normoxia model of PAH is well described in the field, is considered to accurately reflect the human disease of PAH and to predict drug response in humans[25]. Study animals were administered SU5416 20 mg/kg SQ and placed in a COY Hypoxia chamber at FiO2=10%. Animals studied after 1 week hypoxia; 2 weeks hypoxia/12 days normoxia; 3 weeks hypoxia/12 days normoxia; and 3 weeks hypoxia/5 weeks normoxia. End of study procedures included acquisition of right ventricular pressure volume loops with a Scisense Admittance system. The RV PV loops were acquired on ventilated open chest animals with isoflurane anesthesia and 100% $F10_2$. In addition a subset of animals had implantation of DSI PAC40 telemetry catheters in the PA. In this subset, PA pressures were monitored continuously in ambulatory animals, and analysis of PA pressures before and after dosing was performed for 7 days of dosing. See FIGS. 30-31.

Treatment Regimen.

PK10571/trehalose/leucine dry powder or Vehicle was administered twice a day via the CH Technologies Exposure System, in the SUGEN5416/2 week hypoxia/normoxia 2 week subgroups. The results show that there was a significant reduction in RV end systolic pressure after treatment with the in the PK10571 treated group (FIG. 30). There was also a pulsatile effect of PK10571 on PA pressure in that on some days there was a significant decrease in PA systolic pressure after dosing compared to before dosing. However, as the PA pressure came down over time, this acute effect decreased (FIG. 31). These results indicate that PK10571 had both acute vasodilatory effects, but more importantly, a sustained, anti-proliferative/reverse remodeling effect.

As shown in FIG. 30, efficacy of inhaled PK10571 in the SU5416/hypoxia/normoxia model of PAH. NL=normal control; H1=SU5416+1 week hypoxia; H2/N2=SU5416+2 weeks of hypoxia and 12 days of normoxia with inhaled vehicle twice daily during 11 days of normoxia (Vehicle was started on day 2 of normoxia); H3/N2=SU5416+3 weeks hypoxia and 2 weeks normoxia; H2/N2+D=SU5416+2 weeks hypoxia and 12 days of normoxia and treatment with inhaled PK10571 twice daily during 11 days of normoxia. (Drug treatment was started on Day 2 of normoxia). Inhaled PK10571 resulted in a significant decrease in RV end systolic pressure compared to vehicle treated animals (H2/N2). There was no significant difference between H2/N2 and H3/N2 groups. Statistical analysis: ANOVA with Bonferroni correction for multiple comparisons.

As shown in FIG. 31, SU5416/hypoxia(2 weeks)/normoxia(12 days); PA pressures monitored continuously in n=3 animals treated with PK10571 twice daily. Treatment was started the day after removal from the hypoxia chamber (day 2). In our experience there is an initial drop in PA pressure in the first 24 hours after removal from the hypoxia chamber and introduction to normal atmosphere. Therefore we started the drug treatment on day 2 after removal from the hypoxia chamber and continued treatment for 10 days. On day 12, the animals underwent euthanasia and tissue harvest. PA systolic pressure prior to daily dosing (blue) and PA systolic pressure approximately 1 hour after dosing (orange) are shown. Statistical analysis was performed with repeated measures ANOVA and the Bonferroni correction for multiple comparisons. *$p<0.0001$ day 6, 7, 9-12 vs day 2 and 4. Other significant comparisons: Day 1 vs 2,4,5-12 $p<0.0001$; Day 5 vs. Day 11 $p=0.002$.

In the SU5416 model we also examined microfil radiopaque casts of the pulmonary arterial circulation with microCT and 3D reconstruction. The casts were made after flushing the pulmonary circulation of the rats with heparinized saline followed by sodium nitroprusside to maximally vasodilate the pulmonary arterial vessels. Microfil was then injected with a syringe pump at 0.2 ml/min until the proximal PA was engorged and a lattice of microfil was visible in the peripheral lung. The chest was filled with ice saline until the microfil was cured. Preliminary results are shown in FIG. 32, which shows 3D microCT of Pulmonary Arterial Vasculature after treatment with sodium nitroprusside in SU5416/hypoxia/normoxia model of PAH. Vehicle treated animal on left. PK10571 treated animal on right. Resolution: 20 microns. It appears that there are more third and fourth generation branches in the PK10571 treated animal.

Example E analytics for SEM and MDSC data: shown in Table 12 below, are the spray dry conditions performed with a Buchi Bench top spray drier.

TABLE 12

| Batch # | % TS | % API Wt % | Drying gas flow kg/hr | Dryer Inlet Temp C. | Dryer Outlet Temp C. | Feed Solution flow g/min | Atomizer GLR wt/wt | Collector Yield % |
|---|---|---|---|---|---|---|---|---|
| PK-003 | 1.2% | 46 | 23.7 | 124.0 | 70.1 | 5.55 | 5.3 | 57.0% |
| PK-004 | 1.3% | 56 | 23.7 | 124.0 | 70.1 | 6.50 | 4.5 | 63.4% |
| PK-005 | 2.3% | 37 | 23.7 | 116.0 | 70.1 | 4.06 | 7.9 | 73.2% |

A specimen was prepared by distributing the dry powder over the surface of an ultra-smooth conductive carbon adhesive tab (EMS Cat #77827-12) covered specimen stub. The coated stub was then sputter coated with gold/palladium. Imaging was done using a 20 kV beam. See FIGS. 33 and 35.

Modulated DSC (MDSC) was performed using a TA Instruments Q 100 differential scanning calorimeter equipped with a refrigerated cooling system (RCS) and carried out according to Impact Analytical standard operating procedure SOP-THR-011. The purge gas was 50 mL/min nitrogen. Approximately 2 mg of material was weighed into an aluminum hermetic pan and the lid hermetically sealed. Samples were cooled to −90° C. then heated to 300° C. The samples were run using conventional MDSC with a period of 60 seconds, amplitude of ±1.5° C., and a heating rate of 2° C./min. Data were analyzed using TA Instruments Universal Analysis software. See Table 13 below and FIG. 34.

In brief, FIG. 33 is a scanning electron micrograph of PK10571 spray dried with leucine excipient, while FIG. 34 shows the Mass Median Aerodynamic Diameter was determined with an NGI cascade Impactor: T="throat"; PS=preseparator. 1-8=Stages of the NGI cascade impactor. MMAD=Mass median aerodynamic diameter; GSD=geometric standard deviation. Here, PK10571 spray dried with DSPC, where the observed glass transition temperature for PK013 PK10571-DPSC (S142533) was 67° C.

FIG. 35, moreover, shows a scanning electron micrograph of PK10571 with DSPC excipient, while FIG. 36 is a graph showing particle size distribution of PK10571/DSPC spray dry powder. NGI Cascade impactor used at 60 L/min for 4 sec. HPMC capsule loaded in Monodose inhaler. MMAD=2.5 micron GSD 1.6.

FIG. 37 is a chart "CHART A" identifying compound nomenclature, structure and molecular weight (MW), and FIG. 38 is a graph showing compound IC50 data for PDGFRα. Finally, FIG. 39 is a graph showing compound IC50 data for PDGFRβ, where: PK105R=PK10571 racemic mixture; PK105=PK10571; PK19=PK1019; PK23=PK1023; and PK24=PK1024.

TABLE 13

Observed Glass Transition Temperatures

| Sample | $T_g$ (° C.) |
|---|---|
| PK003 Leu/API 1.2 (S141397) | 103 |
| PK004 Leu/API 0.8 (S141398) | 101 |
| PK005 Leu/API 1.7 (S141399) | 105 |

Example F PK10571 Decreases Phosphorylation of PDGF Receptor Beta in Human Lung Fibroblasts PK10571 decreases phosphorylation of PDGF receptor beta in human lung fibroblasts, as shown in FIG. 40. Here, phosphorylated PDGF receptor beta (pPDGFrBeta) and total PDGF receptor beta (PDGFrBeta) data are illustrated via western blot with treated adult human lung fibroblasts (HLFa) at different concentrations of PK10571.

FIG. 40(A) illustrates pPDGFrBeta (Y751), Beta-Actin, Stripped and reprobed with Total PDGFrBeta, note that 25 ug/lane was loaded, with a 1:500 dilution of pPDGFrBeta (Y751) antibody during incubation. The lane key is as follows: Std=Protein Standard Ladder; +Ctrl=Lysate of HLFa treated with 10 ng/mL PDGF BB for 7.5 minutes; −Ctrl=Lysate of HLFa in Serum-free media; SF=Lysate of HLFa in Serum-free media; BB=Lysate of HLFa stimulated with 10 ng/mL PDGF BB for 7.5 minutes in either GM or SF; 10=Lysate of HLFa pre-treated with 10 uM PK10571 for 30 minutes, then stimulated with 20 ng/mL PDGF BB+10 uM PK10571 (Final Concentration of 10 ng/mL PDGF BB) for 7.5 minutes; 1=Lysate of HLFa pre-treated with 1 uM PK10571 for 30 minutes, then stimulated with 20 ng/mL PDGF BB+1 uM PK10571 (Final Concentration of 10 ng/mL PDGF BB) for 7.5 minutes; 0.1=Lysate of HLFa pre-treated with 0.1 1 uM PK10571 for 30 minutes, then stimulated with 20 ng/mL PDGF BB+0.1 uM PK10571 (Final Concentration of 10 ng/mL PDGF BB) for 7.5 minutes; and 0.01=Lysate of HLFa pre-treated with 0.01 uM PK10571 for 30 minutes, then stimulated with 20 ng/mL PDGF BB+0.01 uM PK10571 (Final Concentration of 10 ng/mL PDGF BB) for 7.5 minutes.

FIG. 40(B) illustrates pPDGFrBeta (Y1021), Beta-Actin, Stripped and reprobed with Total PDGFrBeta, note that 25 ug/lane was loaded, with a 1:500 dilution of pPDGFrBeta (Y1021) antibody during incubation. The lane key is as follows: Std=Protein Standard Ladder; +Ctrl=Lysate of HLFa treated with 10 ng/mL PDGF BB for 7.5 minutes; −Ctrl=Lysate of HLFa in Serum-free media; SF=Lysate of HLFa in Serum-free media; BB=Lysate of HLFa stimulated with 10 ng/mL PDGF BB for 7.5 minutes in either GM or SF; 10=Lysate of HLFa pre-treated with 10 uM PK10571 for 30 minutes, then stimulated with 20 ng/mL PDGF BB+10 uM PK10571 (Final Concentration of 10 ng/mL PDGF BB) for 7.5 minutes; 1=Lysate of HLFa pre-treated with 1 uM PK10571 for 30 minutes, then stimulated with 20 ng/mL PDGF BB+1 uM PK10571 (Final Concentration of 10 ng/mL PDGF BB) for 7.5 minutes; 0.1=Lysate of HLFa pre-treated with 0.1 uM PK10571 for 30 minutes, then stimulated with 20 ng/mL PDGF BB+0.1 uM PK10571 (Final Concentration of 10 ng/mL PDGF BB) for 7.5 minutes; and 0.01=Lysate of HLFa pre-treated with 0.01 uM PK10571 for 30 minutes, then stimulated with 20 ng/mL PDGF BB+0.01 uM PK10571 (Final Concentration of 10 ng/mL PDGF BB) for 7.5 minutes.

Example G PK10571 Delivered by Inhalation as a Dry Powder Improved Lung Function in the Rat Monocrotaline Plus Pneumonectomy Model The rat monocrotaline pneumonectomy model is a model of pulmonary hypertension associated with pulmonary fibrosis. Study protocol: male Sprague Dawley rats underwent left pneumonectomy and 10 days later were given monocrotaline 50 mg/kg IP. Twenty one days later inhaled PK10571 was administered twice daily for ten days via a CH technologies inhalation exposure tower with dry powder aerosol generated by a Vilnius Dry Powder Generator.

As shown in FIG. 41, PK10571 significantly improved tidal volume compared to vehicle. Respiratory rate was higher in the vehicle treated animals which compensated for the decreased tidal volume, and thus there was no significant difference in minute ventilation between the groups. There was no significant difference in airway resistance between the PK10571 and vehicle treated animals (Figure). Plethysmography was performed with an EMKA 2 chamber body plethysmograph and data acquired with IOX software. Statistical analysis was performed with XLSTAT. FIG. 41 shows PK10571 dry powder was delivered by inhalation to Sprague Dawley rats with monocrotaline pneumonectomy induced pulmonary hypertension associated with pulmonary fibrosis. PK10571 significantly improved tidal volume (n=12) vs. Vehicle treated animals (n=12); *p=0.006. Respiratory rate was also lower in the PK10571 treated animals (*p=0.005).

As shown in FIG. 42, trichrome stain of lung sections from Vehicle treated animal compared to PK10453 treated animal in rat monocrotaline plus pneumonectomy model. Blue color indicates collagen. There is less collagen deposition evident in the PK10453 treated animal and alveolar architecture appears normal. FIG. 42 shows trichrome stain of lung sections from vehicle treated rat with monocrotaline+pneumonectomy induced pulmonary fibrosis and pulmonary hypertension (left) vs. inhaled PK10453 treated rat monocrotaline+pneumonectomized rat (right). Trichrome stains collagen blue (collagen is increased in the setting of fibrosis). The PK10453 treated animal has less collagen deposition and the alveolar architecture appears normal using an objective 10× microscopic lens.

REFERENCES

1. McLaughlin V V. Classification and epidemiology of pulmonary hypertension. Cardiol Clin 2004; 22:327-41, v.
2. Fisher M R, Mathai S C, Champion H C, et al. Clinical differences between idiopathic and scleroderma-related pulmonary hypertension. Arthritis Rheum 2006; 54:3043-50.
3. McLaughlin V V, Davis M, Cornwell W. Pulmonary arterial hypertension. Curr Probl Cardiol 2011; 36:461-517.
4. Kusano K F. Treatment for pulmonary hypertension including lung transplantation. Gen Thorac Cardiovasc Surg 2011; 59:538-46.
5. Sitbon O, Jays X, Savale L, et al. Upfront triple combination therapy in pulmonary arterial hypertension: a pilot study. Eur Respir J 2014.
6. Pulido T, Rubin L J, Simonneau G. Macitentan and pulmonary arterial hypertension. N Engl J Med 2014; 370:82-3.
7. Montani D, Chaumais M C, Guignabert C, et al. Targeted therapies in pulmonary arterial hypertension. Pharmacology & therapeutics 2014; 141: 172-91.
8. Yang X, Mardekian J, Sanders K N, Mychaskiw M A, Thomas J, 3rd. Prevalence of pulmonary arterial hypertension in patients with connective tissue diseases: a systematic review of the literature. Clin Rheumatol 2013; 32: 1519-31.
9. Simonneau G, Gatzoulis M A, Adatia I, et al. Updated clinical classification of pulmonary hypertension. J Am Coll Cardiol 2013; 62:D34-41.
10. Seferian A, Simonneau G. Therapies for pulmonary arterial hypertension: where are we today, where do we go tomorrow? Eur Respir Rev 2013; 22:217-26.
11. Rubin L J, Galie N, Simonneau G, McLaughlin V. A paradigm shift in pulmonary arterial hypertension management. Eur Respir Rev 2013; 22:423-6.
12. Pulido T, Adzerikho I, Channick R N, et al. Macitentan and morbidity and mortality in pulmonary arterial hypertension. N Engl J Med 2013; 369:809-18.
13. Montani D, Gunther S, Dorfmuller P, et al. Pulmonary arterial hypertension. Orphanet journal of rare diseases 2013; 8:97.
14. Launay D, Sitbon O, Hachulla E, et al. Survival in systemic sclerosis-associated pulmonary arterial hypertension in the modern management era. Ann Rheum Dis 2013; 72: 1940-6.
15. Ghofrani H A, Simonneau G, Rubin L J, Authors of C, Patent. Riociguat for pulmonary hypertension. N Engl J Med 2013; 369:2268.
16. Medarametla V, Festin S, Sugarragchaa C, et al. PK10453, a nonselective platelet-derived growth factor receptor inhibitor, prevents the progression of pulmonary arterial hypertension. Pulm Circ 2014; 4:82-102.
17. Perros F, Montani D, Dorfmuller P, et al. Platelet-derived growth factor expression and function in idiopathic pulmonary arterial hypertension. Am J Res Crit Care Med 2008; 178:81-8.
18. Dahal B K, Heuchel R, Pullamsetti S S, et al. Hypoxic pulmonary hypertension in mice with constitutively active platelet-derived growth factor receptor-beta. Pulm Circ 2011; 1:259-68.
19. Schermuly R T, Dony E, Ghofrani H A, et al. Reversal of experimental pulmonary hypertension by PDGF inhibition. J Clin Invest 2005; 115:2811-21.
20. Grimminger F, Schermuly R T. PDGF receptor and its antagonists: role in treatment of PAH. Adv Exp Med Biol 2010; 661:435-46.
21. Ghofrani H A, Morrell N W, Hoeper M M, et al. Imatinib in pulmonary arterial hypertension patients with inadequate response to established therapy. Am J Respir Crit Care Med 2010; 182: 1171-7.
22. Ciuclan L, Hussey M J, Burton V, et al. Imatinib attenuates hypoxia-induced pulmonary arterial hypertension pathology via reduction in 5-hydroxytryptamine through inhibition of tryptophan hydroxylase 1 expression. Am J Respir Crit Care Med 2013; 187:78-89.
23. Hoeper M M, Barst R J, Bourge R C, et al. Imatinib mesylate as add-on therapy for pulmonary arterial hypertension: results of the randomized IMPRES study. Circulation 2013; 127: 1128-38.
24. Kanno S, Wu Y J, Lee P C, Billiar T R, Ho C. Angiotensin-converting enzyme inhibitor preserves p21 and endothelial nitric oxide synthase expression in monocrotaline-induced pulmonary arterial hypertension in rats. Circulation 2001; 104:945-50.
25. Abe K, Toba M, Alzoubi A, et al. Formation of plexiform lesions in experimental severe pulmonary arterial hypertension. Circulation 2010; 121:2747-54.

What is claimed is:
1. A formulation comprising:
a) a compound of the formula:

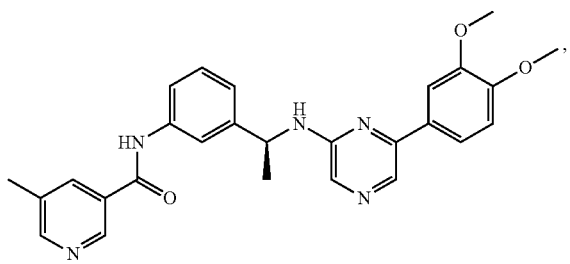

or a pharmaceutically-acceptable salt thereof; and
b) at least one excipient, wherein the excipient comprises a hydrophobic amino acid, wherein the formulation is a powder.
2. The formulation of claim 1, wherein the powder has a moisture content below about 5% by water weight.
3. The formulation of claim 1, wherein the hydrophobic amino acid is leucine.
4. The formulation of claim 1, wherein the formulation further comprises a carbohydrate bulking agent.
5. The formulation of claim 4, wherein the carbohydrate bulking agent is trehalose.
6. The formulation of claim 1, wherein the formulation comprises two excipients.
7. The formulation of claim 6, wherein the excipients are leucine and trehalose.
8. The formulation of claim 1, wherein the powder has an average particle size of about 0.5 to 10 microns.
9. The formulation of claim 1, wherein the compound is present in an amount from 12.67% to 61.73%.

10. A method of treating pulmonary arterial hypertension in a subject in need thereof, the method comprising administering to the subject a formulation comprising:
a) a therapeutically-effective amount of a compound of the formula:

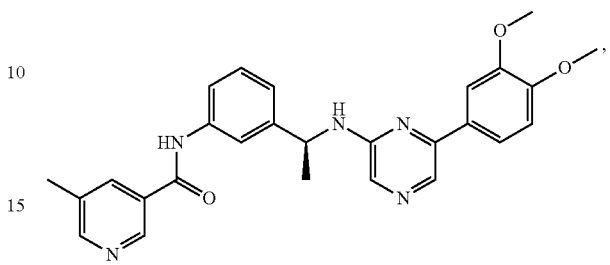

or a pharmaceutically-acceptable salt thereof; and
b) at least one excipient, wherein the excipient comprises a hydrophobic amino acid, wherein the formulation is a powder.
11. The method of claim 10, wherein the administration is by inhalation.
12. The method of claim 10, wherein the administration is intranasal.
13. The method of claim 10, wherein the administration is by an inhaler.
14. The method of claim 10, wherein the administration is by a nebulizer.
15. The method of claim 10, wherein the administration is by an atomizer.
16. The method of claim 10, wherein the therapeutically-effective amount of the compound is from about 0.01 mg/kg to about 100 mg/kg per day.
17. The method of claim 10, wherein the formulation provides a $C_{max}$ of about 1 to 5000 ng/mL of the compound in the subject's plasma after administration to the subject.
18. The method of claim 10, wherein the formulation provides a $C_{max}$ of about 1 to 5000 ng/mL of the compound in the subject's plasma 24 h after administration to the subject.
19. The method of claim 10, wherein the hydrophobic amino acid is leucine.
20. The method of claim 10, wherein the formulation further comprises a carbohydrate bulking agent.
21. The method of claim 20, wherein the carbohydrate bulking agent is trehalose.

* * * * *

UNITED STATES PATENT AND TRADEMARK OFFICE
CERTIFICATE OF CORRECTION

PATENT NO. : 9,925,184 B2  
APPLICATION NO. : 15/028347  
DATED : March 27, 2018  
INVENTOR(S) : Lawrence S. Zisman It is certified that error appears in the above-identified patent and that said Letters Patent is hereby corrected as shown below:

In the Specification

Column 8, Group C structures, Structure 2a:

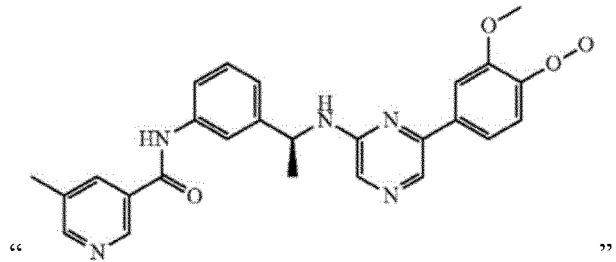

"

Should read:

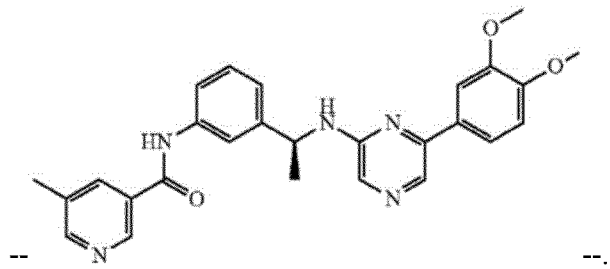

--.

Signed and Sealed this  
Seventeenth Day of September, 2019

Andrei Iancu  
*Director of the United States Patent and Trademark Office*